(12) United States Patent
Moussa et al.

(10) Patent No.: US 12,006,340 B2
(45) Date of Patent: Jun. 11, 2024

(54) NUCLEOTIDE HEMI-SULFATE SALT FOR THE TREATMENT OF HEPATITIS C VIRUS

(71) Applicant: Atea Pharmaceuticals, Inc., Boston, MA (US)

(72) Inventors: Adel Moussa, Burlington, MA (US); Jean-Pierre Sommadossi, Boston, MA (US)

(73) Assignee: Atea Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 18/100,448

(22) Filed: Jan. 23, 2023

(65) Prior Publication Data

US 2024/0018179 A1    Jan. 18, 2024

Related U.S. Application Data

(63) Continuation of application No. 17/306,659, filed on May 3, 2021, now abandoned, which is a continuation of application No. 16/918,918, filed on Jul. 1, 2020, now Pat. No. 10,894,804, which is a continuation of application No. 16/687,136, filed on Nov. 18, 2019, now Pat. No. 10,906,928, which is a continuation of application No. 15/885,630, filed on Jan. 31, 2018, now Pat. No. 10,519,186.

(60) Provisional application No. 62/575,248, filed on Oct. 20, 2017, provisional application No. 62/488,366, filed on Apr. 21, 2017, provisional application No. 62/469,912, filed on Mar. 10, 2017, provisional application No. 62/453,437, filed on Feb. 1, 2017.

(51) Int. Cl.
| | | |
|---|---|---|
| C07H 19/207 | (2006.01) | |
| A61K 9/20 | (2006.01) | |
| A61K 31/7076 | (2006.01) | |
| A61K 31/708 | (2006.01) | |
| A61K 45/06 | (2006.01) | |
| A61P 31/14 | (2006.01) | |
| C07H 19/20 | (2006.01) | |

(52) U.S. Cl.
CPC .............. *C07H 19/20* (2013.01); *A61K 9/20* (2013.01); *A61K 9/2054* (2013.01); *A61K 31/7076* (2013.01); *A61K 31/708* (2013.01); *A61K 45/06* (2013.01); *A61P 31/14* (2018.01); *C07B 2200/13* (2013.01)

(58) Field of Classification Search
None
See application file for complete search history.

(56) References Cited

U.S. PATENT DOCUMENTS

| | | |
|---|---|---|
| 5,977,061 A | 11/1999 | Holy et al. |
| 6,348,587 B1 | 2/2002 | Schinazi et al. |
| 6,602,999 B1 | 8/2003 | Kumar et al. |
| 6,660,721 B2 | 12/2003 | Devos et al. |
| 6,777,395 B2 | 8/2004 | Bhat et al. |
| 6,784,166 B2 | 8/2004 | Devos et al. |
| 6,812,219 B2 | 11/2004 | LaColla et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 6,949,522 B2 | 9/2005 | Otto et al. |
| 7,094,770 B2 | 8/2006 | Watanabe et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,138,376 B2 | 11/2006 | Gosselin et al. |
| 7,148,206 B2 | 12/2006 | Sommadossi et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldrup et al. |
| 7,211,570 B2 | 5/2007 | Schinazi et al. |
| 7,268,119 B2 | 9/2007 | Cook et al. |
| 7,285,658 B2 | 10/2007 | Cook et al. |
| 7,307,065 B2 | 12/2007 | Schinazi et al. |

(Continued)

FOREIGN PATENT DOCUMENTS

| | | |
|---|---|---|
| CN | 103435672 A | 12/2013 |
| CN | 103980332 A | 8/2014 |

(Continued)

OTHER PUBLICATIONS

Petition for Post Grant Review of U.S. Pat. No. 11,642,361; Filed Aug. 7, 2023 (PGR2023-00046—Paper No. 1).

(Continued)

*Primary Examiner* — Traviss C McIntosh, III

(74) *Attorney, Agent, or Firm* — Knowles Intellectual Property Strategies, LLC

(57) ABSTRACT

A hemi-sulfate salt of the structure:

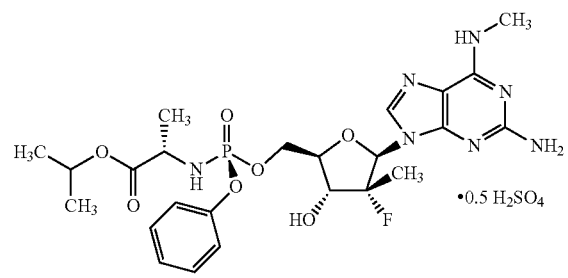

to treat a host infected with hepatitis C, as well as pharmaceutical compositions and dosage forms, including solid dosage forms, thereof.

15 Claims, 28 Drawing Sheets

(56) References Cited

U.S. PATENT DOCUMENTS

| | | |
|---|---|---|
| 7,323,449 B2 | 1/2008 | Olsen et al. |
| 7,339,054 B2 | 3/2008 | Xu et al. |
| 7,365,057 B2 | 4/2008 | LaColla et al. |
| 7,384,924 B2 | 6/2008 | LaColla et al. |
| 7,388,002 B2 | 6/2008 | Babu et al. |
| 7,429,571 B2 | 9/2008 | Chand et al. |
| 7,429,572 B2 | 9/2008 | Clark |
| 7,456,155 B2 | 11/2008 | Sommadossi et al. |
| 7,495,006 B2 | 2/2009 | Liotta et al. |
| 7,514,410 B2 | 4/2009 | Babu et al. |
| 7,534,767 B2 | 5/2009 | Butora et al. |
| 7,547,704 B2 | 6/2009 | LaColla et al. |
| 7,560,434 B2 | 7/2009 | Babu et al. |
| 7,560,550 B2 | 7/2009 | Doring et al. |
| 7,582,618 B2 | 9/2009 | Sommadossi et al. |
| 7,601,820 B2 | 10/2009 | Wang et al. |
| 7,608,597 B2 | 10/2009 | Sommadossi et al. |
| 7,608,599 B2 | 10/2009 | Klumpp et al. |
| 7,608,600 B2 | 10/2009 | Storer et al. |
| 7,608,601 B2 | 10/2009 | Devos et al. |
| 7,625,875 B2 | 12/2009 | Gosselin et al. |
| 7,632,821 B2 | 12/2009 | Butora et al. |
| 7,635,689 B2 | 12/2009 | LaColla et al. |
| 7,638,502 B2 | 12/2009 | Schinazi et al. |
| 7,652,001 B2 | 1/2010 | Hostetler et al. |
| 7,662,798 B2 | 2/2010 | LaColla et al. |
| 7,662,938 B2 | 2/2010 | Schinazi et al. |
| 7,691,603 B2 | 4/2010 | DeFrees |
| 7,713,941 B2 | 5/2010 | Cook et al. |
| 7,718,790 B2 | 5/2010 | Stuyver et al. |
| 7,749,983 B2 | 7/2010 | Hostetler et al. |
| 7,772,208 B2 | 8/2010 | Schinazi et al. |
| 7,824,851 B2 | 11/2010 | Sommadossi et al. |
| 7,842,672 B2 | 11/2010 | Boojamra et al. |
| RE42,015 E | 12/2010 | Watanabe et al. |
| 7,879,815 B2 | 2/2011 | MacCoss et al. |
| 7,902,202 B2 | 3/2011 | Sommadossi et al. |
| 7,919,247 B2 | 4/2011 | Stuyver et al. |
| 7,932,240 B2 | 4/2011 | Dousson et al. |
| 7,951,789 B2 | 5/2011 | Sommadossi et al. |
| 7,964,580 B2 | 6/2011 | Sofia et al. |
| 7,973,013 B2 | 7/2011 | Cho et al. |
| 7,994,139 B2 | 8/2011 | Babu et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,071,567 B2 | 12/2011 | Devos et al. |
| 8,071,568 B2 | 12/2011 | Narjes et al. |
| 8,093,380 B2 | 1/2012 | Wang et al. |
| 8,114,994 B2 | 2/2012 | Liotta et al. |
| 8,114,997 B2 | 2/2012 | Otto et al. |
| 8,119,607 B2 | 2/2012 | Francom et al. |
| 8,133,870 B2 | 3/2012 | Babu et al. |
| 8,148,349 B2 | 4/2012 | Meppen et al. |
| 8,163,703 B2 | 4/2012 | Babu et al. |
| 8,168,583 B2 | 5/2012 | Schinazi et al. |
| 8,173,621 B2 | 5/2012 | Du et al. |
| 8,193,372 B2 | 6/2012 | Dousson et al. |
| 8,242,085 B2 | 8/2012 | Babu et al. |
| 8,299,038 B2 | 10/2012 | Sommadossi et al. |
| 8,318,682 B2 | 11/2012 | Butler et al. |
| 8,324,179 B2 | 12/2012 | Chen et al. |
| 8,334,270 B2 | 12/2012 | Sofia et al. |
| 8,343,937 B2 | 1/2013 | Sommadossi et al. |
| 8,362,068 B2 | 1/2013 | Dousson et al. |
| 8,399,428 B2 | 3/2013 | Wagner |
| 8,399,429 B2 | 3/2013 | Jonckers et al. |
| 8,415,308 B2 | 4/2013 | Cho et al. |
| 8,415,309 B2 | 4/2013 | Francom et al. |
| 8,415,321 B2 | 4/2013 | Schinazi et al. |
| 8,415,322 B2 | 4/2013 | Clark |
| 8,431,588 B2 | 4/2013 | Jonckers et al. |
| 8,440,813 B2 | 5/2013 | Babu et al. |
| 8,455,451 B2 | 6/2013 | Cho et al. |
| 8,470,834 B2 | 6/2013 | Kwong et al. |
| 8,481,510 B2 | 7/2013 | Jonckers et al. |
| 8,481,712 B2 | 7/2013 | Bhat et al. |
| 8,481,713 B2 | 7/2013 | Wang et al. |
| 8,492,539 B2 | 7/2013 | Chun et al. |
| 8,501,699 B2 | 8/2013 | Francom et al. |
| 8,507,460 B2 | 8/2013 | Surleraux et al. |
| 8,541,434 B2 | 9/2013 | Kwong et al. |
| 8,551,973 B2 | 10/2013 | Bao et al. |
| 8,552,021 B2 | 10/2013 | Jonckers et al. |
| 8,563,530 B2 | 10/2013 | Chang et al. |
| 8,575,119 B2 | 11/2013 | Wang et al. |
| 8,580,765 B2 | 11/2013 | Sofia et al. |
| 8,609,627 B2 | 12/2013 | Cho et al. |
| 8,618,076 B2 | 12/2013 | Ross et al. |
| 8,629,263 B2 | 1/2014 | Ross et al. |
| 8,633,309 B2 | 1/2014 | Ross et al. |
| 8,637,475 B1 | 1/2014 | Storer et al. |
| 8,642,756 B2 | 2/2014 | Ross et al. |
| 8,658,616 B2 | 2/2014 | McGuigan et al. |
| 8,673,926 B2 | 3/2014 | Chu |
| 8,674,085 B2 | 3/2014 | Sommadossi et al. |
| 8,680,071 B2 | 3/2014 | Surleraux et al. |
| 8,691,788 B2 | 4/2014 | Sommadossi et al. |
| 8,697,694 B2 | 4/2014 | Arasappan et al. |
| 8,715,638 B2 | 5/2014 | Kwong et al. |
| 8,716,262 B2 | 5/2014 | Sofia et al. |
| 8,716,263 B2 | 5/2014 | Chun et al. |
| 8,735,345 B2 | 5/2014 | Porter et al. |
| 8,735,372 B2 | 5/2014 | Du et al. |
| 8,735,569 B2 | 5/2014 | Ross et al. |
| 8,742,101 B2 | 6/2014 | Storer et al. |
| 8,759,318 B2 | 6/2014 | Chamberlain et al. |
| 8,759,372 B2 | 6/2014 | Roberts et al. |
| 8,759,510 B2 | 6/2014 | Du et al. |
| 8,765,710 B2 | 7/2014 | Sofia et al. |
| 8,772,474 B2 | 7/2014 | Beigelman et al. |
| 8,802,840 B2 | 8/2014 | Francom et al. |
| 8,815,829 B2 | 8/2014 | Schinazi et al. |
| 8,816,074 B2 | 8/2014 | Chu et al. |
| 8,841,275 B2 | 9/2014 | Du et al. |
| 8,846,638 B2 | 9/2014 | Or et al. |
| 8,846,896 B2 | 9/2014 | Serebryany et al. |
| 8,853,171 B2 | 10/2014 | Butler et al. |
| 8,859,595 B2 | 10/2014 | Coats et al. |
| 8,859,756 B2 | 10/2014 | Ross et al. |
| 8,871,737 B2 | 10/2014 | Smith et al. |
| 8,871,785 B2 | 10/2014 | Boojamra et al. |
| 8,877,731 B2 | 11/2014 | Beigelman et al. |
| 8,877,733 B2 | 11/2014 | Cho et al. |
| 8,889,159 B2 | 11/2014 | Cleary et al. |
| 8,889,701 B1 | 11/2014 | Ivachtchenko et al. |
| 8,895,531 B2 | 11/2014 | Shi |
| 8,895,723 B2 | 11/2014 | Serebryany et al. |
| 8,906,880 B2 | 12/2014 | Du et al. |
| 8,912,321 B2 | 12/2014 | Axt et al. |
| 8,921,384 B2 | 12/2014 | Chu |
| 8,927,513 B2 | 1/2015 | Manoharan et al. |
| 8,933,052 B2 | 1/2015 | Jonckers et al. |
| 8,946,244 B2 | 2/2015 | Chu et al. |
| 8,951,985 B2 | 2/2015 | Surleraux et al. |
| 8,957,045 B2 | 2/2015 | Sofia et al. |
| 8,957,046 B2 | 2/2015 | Du et al. |
| 8,980,865 B2 | 3/2015 | Wang et al. |
| 9,012,427 B2 | 4/2015 | Blatt et al. |
| 9,012,428 B2 | 4/2015 | Jonckers et al. |
| 9,045,520 B2 | 6/2015 | Chun et al. |
| 9,061,041 B2 | 6/2015 | Girijavallabhan et al. |
| 9,085,573 B2 | 7/2015 | Du et al. |
| 9,085,599 B2 | 7/2015 | Or et al. |
| 9,090,642 B2 | 7/2015 | Cho et al. |
| 9,109,001 B2 | 8/2015 | Parsy et al. |
| 9,139,604 B2 | 9/2015 | Boojamra et al. |
| 9,156,872 B2 | 10/2015 | Girijavallabhan et al. |
| 9,173,893 B2 | 11/2015 | Cho et al. |
| 9,187,515 B2 | 11/2015 | Mayes et al. |
| 9,192,621 B2 | 11/2015 | Mayes et al. |
| 9,211,300 B2 | 12/2015 | Mayes et al. |
| 9,243,025 B2 | 1/2016 | Surleraux et al. |
| 9,249,174 B2 | 2/2016 | Beigelman et al. |

(56) References Cited

U.S. PATENT DOCUMENTS

| | | | |
|---|---|---|---|
| 9,339,541 B2 | 5/2016 | Dousson et al. |
| 9,351,989 B2 | 5/2016 | McGuigan et al. |
| 9,403,863 B2 | 8/2016 | Surleraux et al. |
| 9,408,863 B2 | 8/2016 | Verma et al. |
| 9,447,132 B2 | 9/2016 | Deshpande et al. |
| 9,598,457 B2 | 3/2017 | Smith et al. |
| 9,603,863 B2 | 3/2017 | Blatt et al. |
| 9,603,864 B2 | 3/2017 | Blatt et al. |
| 9,758,544 B2 | 9/2017 | Beigelman et al. |
| 9,815,864 B2 | 11/2017 | Beigelman et al. |
| 9,822,137 B2 | 11/2017 | Dehaen et al. |
| 9,828,410 B2 | 11/2017 | Sommadossi et al. |
| 9,890,188 B2 | 2/2018 | Wang et al. |
| 10,000,523 B2 | 6/2018 | Sommadossi et al. |
| 10,005,810 B2 | 6/2018 | McGuigan et al. |
| 10,005,811 B2 | 6/2018 | Sommadossi et al. |
| 10,202,412 B2 | 2/2019 | Sommadossi et al. |
| 10,239,911 B2 | 3/2019 | Sommadossi et al. |
| 10,519,186 B2 | 12/2019 | Moussa et al. |
| 10,815,266 B2 | 10/2020 | Sommadossi et al. |
| 10,870,672 B2 | 12/2020 | Sommadossi et al. |
| 10,870,673 B2 | 12/2020 | Sommadossi et al. |
| 10,874,687 B1 | 12/2020 | Sommadossi et al. |
| 10,875,885 B2 | 12/2020 | Sommadossi et al. |
| 10,894,804 B2 | 1/2021 | Moussa et al. |
| 10,906,928 B2 | 2/2021 | Moussa et al. |
| 10,946,033 B2 | 3/2021 | Sommadossi et al. |
| 11,642,361 B2 | 5/2023 | Sofia et al. |
| 11,690,860 B2 | 7/2023 | Sommadossi et al. |
| 11,707,480 B2 | 7/2023 | Sommadossi et al. |
| 11,738,038 B2 | 8/2023 | Sommadossi et al. |
| 11,813,278 B2 | 11/2023 | Sommadossi et al. |
| 2002/0045599 A1 | 4/2002 | Arimilli et al. |
| 2002/0058635 A1 | 5/2002 | Averett |
| 2003/0087873 A1 | 5/2003 | Stuyver et al. |
| 2004/0063658 A1 | 4/2004 | Roberts et al. |
| 2004/0229839 A1 | 11/2004 | Babu et al. |
| 2004/0259934 A1 | 12/2004 | Olsen et al. |
| 2005/0038240 A1 | 2/2005 | Connolly et al. |
| 2005/0203044 A1 | 9/2005 | Zinnen |
| 2007/0265222 A1 | 11/2007 | MacCoss et al. |
| 2008/0207554 A1 | 8/2008 | Beigelman et al. |
| 2008/0286230 A1 | 11/2008 | Sommadossi et al. |
| 2009/0156545 A1 | 6/2009 | Hostetler et al. |
| 2009/0176732 A1 | 7/2009 | Beigelman et al. |
| 2009/0181921 A1 | 7/2009 | Blatt et al. |
| 2009/0318380 A1 | 12/2009 | Sofia et al. |
| 2010/0137576 A1 | 6/2010 | Stec et al. |
| 2010/0240604 A1 | 9/2010 | Beigelman et al. |
| 2010/0249068 A1 | 9/2010 | Beigelman et al. |
| 2010/0279969 A1 | 11/2010 | Schinazi et al. |
| 2010/0286083 A1 | 11/2010 | Bao et al. |
| 2010/0331397 A1 | 12/2010 | Beigelman et al. |
| 2011/0015146 A1 | 1/2011 | Sofia et al. |
| 2011/0091943 A1 | 4/2011 | Gallou et al. |
| 2011/0257121 A1 | 10/2011 | Chang et al. |
| 2012/0070411 A1 | 3/2012 | Beigelman et al. |
| 2012/0135951 A1 | 5/2012 | Schinazi et al. |
| 2012/0245335 A1 | 9/2012 | Clark |
| 2013/0064794 A1 | 3/2013 | Surleraux et al. |
| 2013/0225636 A1* | 8/2013 | Roberts .......... A61P 43/00 546/118 |
| 2013/0244966 A1 | 9/2013 | Milne et al. |
| 2013/0273005 A1 | 10/2013 | Delaney et al. |
| 2013/0315868 A1 | 11/2013 | Mayes et al. |
| 2014/0038916 A1 | 2/2014 | Wang et al. |
| 2014/0066395 A1 | 3/2014 | Cho et al. |
| 2014/0112886 A1 | 4/2014 | Moussa et al. |
| 2014/0187511 A1 | 7/2014 | Du et al. |
| 2014/0212382 A1 | 7/2014 | Schinazi et al. |
| 2014/0235566 A1 | 8/2014 | Amblard et al. |
| 2015/0011481 A1 | 1/2015 | Vilchez et al. |
| 2015/0011497 A1 | 1/2015 | Beigelman et al. |
| 2015/0057243 A1 | 2/2015 | Zhou et al. |
| 2015/0105341 A1 | 4/2015 | Beigelman et al. |
| 2015/0150897 A1 | 6/2015 | Denning et al. |
| 2015/0183818 A1 | 7/2015 | Tran et al. |
| 2016/0002281 A1 | 1/2016 | Mayes et al. |
| 2016/0220595 A1 | 8/2016 | Liotta et al. |
| 2016/0257706 A1* | 9/2016 | Sommadossi ...... A61K 31/7076 |
| 2016/0271162 A1 | 9/2016 | Moussa et al. |
| 2017/0022242 A1 | 1/2017 | Herdewyn et al. |
| 2017/0029456 A1 | 2/2017 | Dousson et al. |
| 2017/0275322 A1 | 9/2017 | Oinho et al. |
| 2018/0009836 A1 | 1/2018 | Sommadossi et al. |
| 2019/0153017 A1 | 5/2019 | Sommadossi et al. |
| 2019/0201433 A1 | 7/2019 | Sommadossi et al. |
| 2020/0087339 A1 | 3/2020 | Moussa et al. |
| 2023/0017958 A1 | 1/2023 | Sommadossi et al. |
| 2023/0049294 A1 | 2/2023 | Moussa |
| 2023/0331751 A1 | 10/2023 | Moussa et al. |
| 2023/0364121 A1 | 11/2023 | Sommadossi et al. |
| 2023/0365611 A1 | 11/2023 | Moussa |

FOREIGN PATENT DOCUMENTS

| | | |
|---|---|---|
| CN | 105646629 A | 6/2016 |
| CN | 106188192 A | 12/2016 |
| EP | 547008 A1 | 6/1993 |
| EP | 398231 B1 | 7/1997 |
| WO | WO 1998/16184 | 4/1998 |
| WO | WO 2001/009143 A1 | 2/2001 |
| WO | WO 2001/90121 A2 | 11/2001 |
| WO | WO 2001/92282 A2 | 12/2001 |
| WO | WO 2002/32920 A2 | 4/2002 |
| WO | WO 2003/033508 A1 | 4/2003 |
| WO | WO 2003/039523 A2 | 5/2003 |
| WO | WO 2003/062256 A1 | 7/2003 |
| WO | WO 2003/093290 A2 | 11/2003 |
| WO | WO 2004/002999 A2 | 1/2004 |
| WO | WO 2004/003000 A2 | 1/2004 |
| WO | WO 2004/014312 A2 | 2/2004 |
| WO | WO 2004/052906 A2 | 6/2004 |
| WO | WO 2004/074350 A2 | 9/2004 |
| WO | WO 2004/091499 A2 | 10/2004 |
| WO | WO 2004/106356 A1 | 12/2004 |
| WO | WO 2005/000864 A1 | 1/2005 |
| WO | WO 2005/003147 A2 | 1/2005 |
| WO | WO 2005/020884 A2 | 3/2005 |
| WO | WO 2005/021568 A2 | 3/2005 |
| WO | WO 2005/084192 A2 | 9/2005 |
| WO | WO 2005/090370 A1 | 9/2005 |
| WO | WO 2006/012078 A2 | 2/2006 |
| WO | WO 2006/063149 A1 | 6/2006 |
| WO | WO 2006/063717 A2 | 7/2006 |
| WO | WO 2006/094347 A1 | 9/2006 |
| WO | WO 2006/102533 A2 | 9/2006 |
| WO | WO 2006/121820 A1 | 11/2006 |
| WO | WO 2006/130217 A2 | 12/2006 |
| WO | WO 2007/022073 A2 | 2/2007 |
| WO | WO 2007/112028 A2 | 10/2007 |
| WO | WO 2007/130783 A1 | 11/2007 |
| WO | WO 2008/012555 A2 | 1/2008 |
| WO | WO 2008/048128 A1 | 4/2008 |
| WO | WO 2008/062206 A2 | 5/2008 |
| WO | WO 2008/095040 A2 | 10/2008 |
| WO | WO 2009/001097 A2 | 12/2008 |
| WO | WO 2009/003042 A1 | 12/2008 |
| WO | WO 2009/067409 A1 | 5/2009 |
| WO | WO 2009/086192 A1 | 7/2009 |
| WO | WO 2009/086201 A1 | 7/2009 |
| WO | WO 2009/129120 A2 | 10/2009 |
| WO | WO 2010/081082 A2 | 7/2010 |
| WO | WO 2010/091386 A2 | 8/2010 |
| WO | WO 2010/108135 A1 | 9/2010 |
| WO | WO 2010/145778 | 12/2010 |
| WO | WO 2011/005595 A1 | 1/2011 |
| WO | WO 2011/005860 A2 | 1/2011 |
| WO | WO 2012/041965 A1 | 4/2012 |
| WO | WO 2012/048013 A2 | 4/2012 |
| WO | WO 2012/092484 A2 | 7/2012 |
| WO | WO 2012/125900 A1 | 9/2012 |
| WO | WO 2012/154321 A1 | 11/2012 |
| WO | WO 2012/158811 A2 | 11/2012 |

(56) References Cited

FOREIGN PATENT DOCUMENTS

| | | |
|---|---|---|
| WO | WO 2013/009737 A1 | 1/2013 |
| WO | WO 2013/019874 A1 | 2/2013 |
| WO | WO 2013/039855 A1 | 3/2013 |
| WO | WO 2013/039920 A1 | 3/2013 |
| WO | WO 2013/044030 A1 | 3/2013 |
| WO | WO 2013/059735 A1 | 4/2013 |
| WO | WO 2013/090420 A2 | 6/2013 |
| WO | WO 2013/096680 A1 | 6/2013 |
| WO | WO 2013/142125 A1 | 9/2013 |
| WO | WO 2013/142157 A1 | 9/2013 |
| WO | WO 2013/142159 A1 | 9/2013 |
| WO | WO 2013/151975 A1 | 10/2013 |
| WO | WO 2013/177219 A1 | 11/2013 |
| WO | WO 2013/187978 A1 | 12/2013 |
| WO | WO 2014/008236 A1 | 1/2014 |
| WO | WO 2014/047117 A1 | 3/2014 |
| WO | WO 2014/052638 A1 | 4/2014 |
| WO | WO 2014/063019 A1 | 4/2014 |
| WO | WO 2014/076490 A1 | 5/2014 |
| WO | WO 2014/082935 A1 | 6/2014 |
| WO | WO 2014/100498 A1 | 6/2014 |
| WO | WO 2014/100505 A1 | 6/2014 |
| WO | WO 2014/120981 A1 | 8/2014 |
| WO | WO 2014/124430 A1 | 8/2014 |
| WO | WO 2014/137930 A1 | 9/2014 |
| WO | WO 2014/169278 A1 | 10/2014 |
| WO | WO 2014/169280 A2 | 10/2014 |
| WO | WO 2014/209979 A1 | 12/2014 |
| WO | WO 2015/038596 A1 | 3/2015 |
| WO | WO 2015/053662 A1 | 4/2015 |
| WO | WO 2015/081133 A2 | 6/2015 |
| WO | WO 2015/095305 A1 | 6/2015 |
| WO | WO 2015/158913 A1 | 10/2015 |
| WO | WO 2016/041877 A1 | 3/2016 |
| WO | WO 2016/100441 A1 | 6/2016 |
| WO | WO 2016/100569 A1 | 6/2016 |
| WO | WO 2016/144918 A1 | 9/2016 |
| WO | WO 2016/145142 A1 | 9/2016 |
| WO | WO 2018/013937 A1 | 1/2018 |
| WO | WO 2018/048937 A1 | 3/2018 |
| WO | WO 2019/200005 A1 | 10/2019 |

OTHER PUBLICATIONS

Declaration of Alexander M. Klibanov, Ph.D.; Filed Aug. 6, 2023 (PGR2023-00046—Exhibit No. 15).
Bukrinskaya A.G., Virology—M.: Medicine, 1986, p. 152, lines 12-15 from the top.
Mashkovsky, M.D. "Medicines, a guide for doctors", 1993, part. 1, Moscow, "Medicine", p. 8.
Wu, Jim Zhen et al. "Ribavirin, viramidine and adenosine-deaminase-catalysed drug activation: implication for nucleoside prodrugs design," Journal of Antimicrobial Chemotherapy (2003) 52, 543-546.
Yoon et al. "Design, Synthesis, and Anti-RNA Virus of 6'-Fluorinated-Aristeromycin Analogues," Journal of Medicine Chemistry, Jun. 7, 2019, vol. 62, p. 6346-6362.
Ahmad, T. et al. "Cardiac dysfunction associated with a nucleotide polymerase inhibitor for treatment of hepatitis C" Hepatology 2015, 62, 409.
Ahn et al., "Biochemical characterization of a recombinant SARS coronavirus nsp12 RNA-dependent RNA polymerase capable of copying viral RNA templates", Arch Virol. 2012, 157, 2095-2104.
Berge, M.S. et al. "Pharmaceutical Salts" Journal of Pharmaceutical Sciences, 1977, 66, 1.
Berliba, et al., "Safety, Pharmacokinetics, and Antiviral Activity of AT-527, a Novel Purine Nucleotide Prodrug, in Hepatitis C Virus-Infected Subjects with or without Cirrhosis," Antimicrobial Agents and Chemotherapy, Dec. 2019, vol. 63, Issue 12.
Chang, W. et al. "Discovery of PSI-353661, a Novel Purine Nucleotide Prodrug for the Treatment of HCV Infection" ACS Med Chem Lett. 2011, 2, 130.

Cretton-Scott, E. et al. "In vitro antiviral activity and pharmacology of idx184, a novel and potent inhibitor of HCV replication" (Abstract 588) J. Hepatol. 2008, 48, Supplement 2, S220.
Freeman et al. 2-amino-9(3-azido-2,3-dideoxy-β-D-erythro-pentofuranosyl)-6-Substituted-9H-Purines: Synthesis and Anti-HIV Activity. Bioorganic and Medicinal Chemistry, 1995; 3(4): 447-448.
Gao et al., "Structure of the RNA-dependent RNA polymerase from COVID-19 virus", Science, 2020, 368(6492), 779-782.
Good, et al., "AT-527, a Double Prodrug of a Guanosine Nucleotide Analog, Is a Potent Inhibitor of SARS-CoV-2 In Vitro and a Promising Oral Antiviral for Treatment of COVID19" Antimicrobial Agents and Chemotherapy, Apr. 2021, vol. 65, Issue 4.
Good, et al., "Preclinical evaluation of AT-527, a novel guanosine nucleotide prodrug with potent, pan-genotypic activity against hepatitis C virus, " Plos One, https://doi.org/10.1371/journal.pone.0227104, Jan. 8, 2020.
Good, S et al. "AT-337, AT-511, and its Salt Form, AT-527: Novel Potent and Selective Pan-genotypic Purine Nucleotide Prodrug Inhibitors of HCV Polymerase" presented at the AASLD 2017 Liver Meeting; Oct. 20, 2017-Oct. 24, 2017; Washington, D.C.
Herman, B. et al. "Substrate mimicry: HIV-1 reverse transcriptase recognizes 6-modified-30-azido-20,30-dideoxyguanosine-50-triphosphates as adenosine analogs" Nucleic Acids Research 2012, 40, 381.
Hoffman, M. et al., "SARS-CoV-2 Cell Entry Depends on ACE2 and TMPRSS2 and Is Blocked by a Clinically Proven Protease Inhibitor", Cell, 2020, 181(2), 271-280.
Huang et al. "Impact of solid state properties on developability assessment of drug candidates" Advanced Drug Delivery Reviews. 2004, 56, 321.
Huang et al., "Clinical features of patients infected with 2019 novel coronavirus in Wuhan, China", Lancet, 2020, 395(10223), 497-506.
Lau et al., "Severe acute respiratory syndrome coronavirus-like virus in Chinese horseshoe bats", PNAS, 2005, 102(39), 14040-14045.
Luan et al., "Spike protein recognition of mammalian ACE2 predicts the host range and an optimized ACE2 for SARS-CoV-2 infection", Biochem. Biophys. Res. Commun., 2020, 526(1), 165-169.
McGuigan, C. et al. "Design, synthesis and evaluation of a novel double pro-drug: INX-08189. A new clinical candidate for hepatitis C virus" Bioorganic & Medicinal Chemistry Letters 2010, 20, 4850.
McGuigan, C. et al. "Dual pro-drugs of 2'-C-methyl guanosine monophosphate as potent and selective inhibitors of hepatitis C virus" Bioorganic & Medicinal Chemistry Letters 2011, 21, 6007.
Murakami, E. et al. "Adenosine Deaminase-like Protein 1 (ADAL1): Characterization and Substrate Specificity in the Hydrolysis of N6- or O6-Substituted Purine or 2-Aminopurine Nucleoside Monophosphates" J Med Chem 2011, 54, 5902.
Musso, Didier, et al. Zika Virus Clinical Microbiology Reviews, American Society for Microbiology, Jul. 2016, vol. 29, No. 3, 489-524.
Noriaki Hirayama, Handbook for Producing Organic Compound Crystals, 2008, pp. 17-23, 37-40, 45-51, and 57-65 (reference showing a well-known technique) and English partial translation.
Nguyen, Lien et al., International Journal of Biomedical Science: Chiral Drugs: An Overview; Jun. 2, 2006(20; 85-100).
Poorad et al. "Daclatasvir with Sofosbuvir and Ribavirin for Hepatitis C Virus Infection with Advanced Cirrhosis or Post-Liver Transplantation Recurrence" Hepatology, 2016, 63, 1493.
Pradere, U. et al. "Synthesis of 5'-Methylene-Phosphonate Furanonucleoside Prodrugs: Application to D-2'-Deoxy-2'-α-fluoro-2'-β-C-methyl Nucleosides" Organic Letters 2012, 14, 4426.
Reddy, P. et al. "2'-Deoxy-2'-α-fluoro-2'-β-C-methyl 3',5'-cyclic phosphate nucleotide prodrug analogs as inhibitors of HCV NS5B polymerase: Discovery of PSI-352938" Bioorganic & Medicinal Chemistry Letters 2010, 20, 7376.
Rest et al., "SARS associated coronavirus has a recombinant polymerase and coronaviruses have a history of host-shifting", Infect Genet Evol., 2003, 3(3), 219-225.
Schoeman and Fielding, "Coronavirus envelope protein: current knowledge", Virology 2019, 16(69), 1-22.

(56) References Cited

OTHER PUBLICATIONS

Serajuddin, A.T.M "Salt formation to improve drug solubility" Advanced Drug Delivery Reviews, 2007, 59, 603.

Sofia, M.J. "Nucleotide Prodrugs for HCV Therapy," Antiviral Chemistry & Chemotherapy, 2011; 22, 23.

Stahl et al., "Handbook of Pharmaceutical Salts Properties, Selection, and Use", International Union of Pure and Applied Chemistry (IUPAC), 2002 (Chapters 6 and 7).

Subissi et al., "One severe acute respiratory syndrome coronavirus protein complex integrates processive RNA polymerase and exonuclease activities", Proc. Natl. Acad. Sci., 2014, 111(37), E3900-E3909.

Tao, S., Zhou, L., Zhang, H., Zhou, S., Amiralaei, S., Shelton, J.R., Coats, S.J., Schinazi, R.F.: Comparison of Three 2'-C-Methyl Guanosine Prodrugs for Hepatitis C including a Novel $^2$-D-2'-C-Me-2,6-Diaminopurine Ribonucleoside Phosphoramidate (RS-1389): Interspecies Hepatocyte and Human Cardiomyocyte Metabolism Profiles. The Liver Meeting 2014. Boston, MA, USA. Nov. 6-11, 2014.

Yang et al., "Targeting the Endocytic Pathway and Autophagy Process as a Novel Therapeutic Strategy in COVID-19", Int. J. Biol. Sci. 2020, 16(10), 1724-1731.

VG Belikov Pharmaceutical Chemistry, Fourth Edition, revised textbook, 2007, Moscow 30 "MEDpress-inform" pp. 27-29.

Zhang et al. "Synthesis and evaluation of 30-azido-20,30-dideoxypurine nucleosides as inhibitors of human immunodeficiency virus" Bioorganic and Medicinal Chemistry Letters 2010, 20, 60.

Zhou et al., "A pneumonia outbreak associated with a new coronavirus of probable bat origin", Nature, 2020, 579, 270.

Zhou, L. et al. "β-D-2'-C-Methyl-2,6-diaminopurine Ribonucleoside Phosphoramidates are Potent and Selective Inhibitors of Hepatitis C Virus (HCV) and Are Bioconverted Intracellularly to Bioactive 2,6-Diaminopurine and Guanosine 5'-Triphosphate Forms" J Med Chem 2015, 58, 3445.

Zhou, X. et al. "A Phase la Study of AT-527, a Novel Pan-Genotypic Purine Nucleotide Prodrug Inhibitor of Hepatitis C Virus (HCV)" presented at The Liver Meeting 2017; Oct. 23, 2017; Washington, D.C.

Zhou, X. et al. "AT-527, a pan-genotypic purine nucleotide prodrug, exhibits potent antiviral activity in subjects with chronic hepatitis C" presented at The International Liver Congress 2018; Apr. 13, 2018; Paris, France.

U.S. Appl. No. 18/540,608, Sommadossi et al., filed Dec. 14, 2023.
U.S. Appl. No. 18/368,959, Sommadossi et al., filed Sep. 15, 2023.
U.S. Appl. No. 18/225,452, Sommadossi et al., filed Jul. 24, 2023.

\* cited by examiner

NUCLEOTIDE HEMI-SULFATE SALT FOR THE TREATMENT OF HEPATITIS C VIRUS

CROSS-REFERENCE TO RELATED APPLICATIONS

This application is a continuation of U.S. application Ser. No. 17/306,659, filed May 3, 2021, which is a continuation of Ser. No. 16/918,918, filed Jul. 1, 2020, now U.S. Pat. No. 10,894,804, which is a continuation of U.S. application Ser. No. 16/687,136, filed Nov. 18, 2019, now U.S. Pat. No. 10,906,928, which is a continuation of U.S. application Ser. No. 15/885,630, filed Jan. 31, 2018, now U.S. Pat. No. 10,519,186, issued Dec. 21, 2019, which claims the benefit of provisional U.S. Application Nos. 62/453,437 filed Feb. 1, 2017; 62/469,912 filed Mar. 10, 2017; 62/488,366 filed Apr. 21, 2017; and, 62/575,248 filed Oct. 20, 2017. The entirety of these applications are incorporated by reference herein for all purposes.

FIELD OF THE INVENTION

The present invention is the hemi-sulfate salt of a selected nucleotide compound that has unexpected therapeutic properties to treat a host infected with hepatitis C, as well as pharmaceutical compositions and dosage forms thereof.

BACKGROUND OF THE INVENTION

Hepatitis C (HCV) is an RNA single-stranded virus and member of the Hepacivirus genus. It is estimated that 75% of all cases of liver disease are caused by HCV. HCV infection can lead to cirrhosis and liver cancer, and if left to progress, liver failure that may require a liver transplant. Approximately 71 million people worldwide are living with chronic HCV infections and approximately 399,000 people die each year from HCV, mostly from cirrhosis and hepatocellular carcinoma.

RNA polymerase is a key target for drug development against RNA single stranded viruses. The HCV non-structural protein NS5B RNA-dependent RNA polymerase is a key enzyme responsible for initiating and catalyzing viral RNA synthesis. There are two major subclasses of NS5B inhibitors: nucleoside analogs and non-nucleoside inhibitors (NNIs). Nucleoside analogs are anabolized to active triphosphates that act as alternative substrates for the polymerase and non-nucleoside inhibitors (NNIs) bind to allosteric regions on the protein. Nucleoside or nucleotide inhibitors mimic natural polymerase substrates and act as chain terminators. They inhibit the initiation of RNA transcription and elongation of a nascent RNA chain.

In addition to targeting RNA polymerase, other RNA viral proteins may also be targeted in combination therapies. For example, HCV proteins that are additional targets for therapeutic approaches are NS3/4A (a serine protease) and NS5A (a non-structural protein that is an essential component of HCV replicase and exerts a range of effects on cellular pathways).

In December 2013, the first nucleoside NS5B polymerase inhibitor sofosbuvir (Sovaldi®, Gilead Sciences) was approved. Sovaldi® is a uridine phosphoramidate prodrug that is taken up by hepatocytes and undergoes intracellular activation to afford the active metabolite, 2'-deoxy-2'-α-fluoro-β-C-methyluridine-5'-triphosphate.

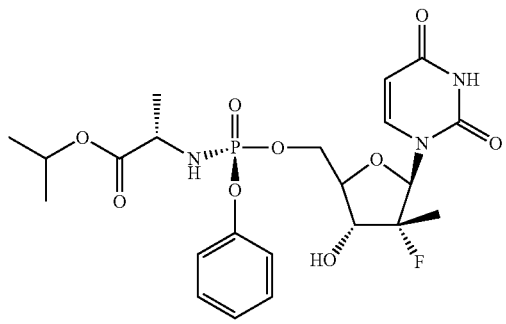

Sovaldi®

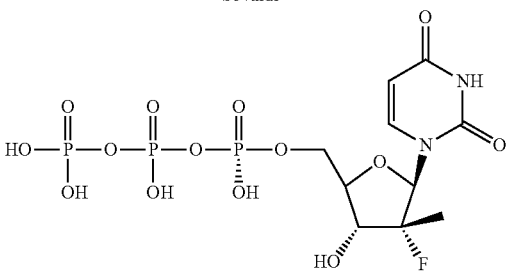

2'-Deoxy-2'-α-fluoro-β-C-methyluridine-5'-triphosphate

Sovaldi® is the first drug that has demonstrated safety and efficacy to treat certain types of HCV infection without the need for co-administration of interferon. Sovaldi® is the third drug with breakthrough therapy designation to receive FDA approval.

In 2014, the U.S. FDA approved Harvoni® (ledispasvir, a NS5A inhibitor, and sofosbuvir) to treat chronic hepatitis C virus Genotype 1 infection. Harvoni® is the first combination pill approved to treat chronic HCV Genotype 1 infection. It is also the first approved regimen that does not require administration with interferon or ribavirin. In addition, the FDA approved simeprevir (Olysio™) in combination with sofosbuvir (Sovaldi®) as a once-daily, all oral, interferon and ribavirin-free treatment for adults with Genotype 1 HCV infection.

The U.S. FDA also approved AbbVie's VIEKIRA Pak™ in 2014, a multi-pill pack containing dasabuvir (a non-nucleoside NS5B polymerase inhibitor), ombitasvir (a NS5A inhibitor), paritaprevir (a NS3/4A inhibitor), and ritonavir. The VIEKIRA Pak™ can be used with or without the ribavirin to treat Genotype 1 HCV infected patients including patients with compensated cirrhosis. VIEKIRA Pak™ does not require interferon co-therapy.

In July 2015, the U.S. FDA approved Technivie™ and Daklinza™ for the treatment of HCV genotype 4 and HCV Genotype 3, respectively. Technivie™ (Ombitasvir/paritaprevir/ritonavir) was approved for use in combination with ribavirin for the treatment of HCV genotype 4 in patients without scarring and cirrhosis and is the first option for HCV-4 infected patients who do not require co-administration with interferon. Daklinza™ was approved for use with Sovaldi® to treat HCV genotype 3 infections. Daklinza™ is the first drug that has demonstrated safety and efficacy in treating HCV Genotype 3 without the need for co-administration of interferon or ribavirin.

In October 2015, the U.S. FDA warned that HCV treatments Viekira Pak and Technivie can cause serious liver injury primarily in patients with underlying advanced liver disease and required that additional information about safety be added to the label.

Other current approved therapies for HCV include interferon alpha-2b or pegylated interferon alpha-2b (Pegintron®), which can be administered with ribavirin (Rebetol®), NS3/4A telaprevir (Incivek®, Vertex and Johnson & Johnson), boceprevir (Victrelis™, Merck), simeprevir (Olysio™, Johnson & Johnson), paritaprevir (AbbVie), Ombitasvir (AbbVie), the NNI Dasabuvir (ABT-333) and Merck's Zepatier™ (a single-tablet combination of the two drugs grazoprevir and elbasvir).

Additional NS5B polymerase inhibitors are currently under development. Merck is developing the uridine nucleotide prodrug MK-3682 (formerly Idenix IDX21437) and the drug is currently in Phase II combination trials.

United States patents and WO applications that describe nucleoside polymerase inhibitors for the treatment of Flaviviridae, including HCV, include those filed by Idenix Pharmaceuticals (U.S. Pat. Nos. 6,812,219; 6,914,054; 7,105,493; 7,138,376; 7,148,206; 7,157,441; 7,163,929; 7,169,766; 7,192,936; 7,365,057; 7,384,924; 7,456,155; 7,547,704; 7,582,618; 7,608,597; 7,608,600; 7,625,875; 7,635,689; 7,662,798; 7,824,851; 7,902,202; 7,932,240; 7,951,789; 8,193,372; 8,299,038; 8,343,937; 8,362,068; 8,507,460; 8,637,475; 8,674,085; 8,680,071; 8,691,788; 8,742,101; 8,951,985; 9,109,001; 9,243,025; US2016/0002281; US2013/0064794; WO/2015/095305; WO/2015/081133; WO/2015/061683; WO/2013/177219; WO/2013/039920; WO/2014/137930; WO/2014/052638; WO/2012/154321); Merck (U.S. Pat. Nos. 6,777,395; 7,105,499; 7,125,855; 7,202,224; 7,323,449; 7,339,054; 7,534,767; 7,632,821; 7,879,815; 8,071,568; 8,148,349; 8,470,834; 8,481,712; 8,541,434; 8,697,694; 8,715,638, 9,061,041; 9,156,872 and WO/2013/009737); Emory University (U.S. Pat. Nos. 6,348,587; 6,911,424; 7,307,065; 7,495,006; 7,662,938; 7,772,208; 8,114,994; 8,168,583; 8,609,627; US 2014/0212382; and WO2014/1244430); Gilead Sciences/Pharmasset Inc. (7,842,672; 7,973,013; 8,008,264; 8,012,941; 8,012,942; 8,318,682; 8,324,179; 8,415,308; 8,455,451; 8,563,530; 8,841,275; 8,853,171; 8,871,785; 8,877,733; 8,889,159; 8,906,880; 8,912,321; 8,957,045; 8,957,046; 9,045,520; 9,085,573; 9,090,642; and 9,139,604) and (U.S. Pat. Nos. 6,908,924; 6,949,522; 7,094,770; 7,211,570; 7,429,572; 7,601,820; 7,638,502; 7,718,790; 7,772,208; RE42,015; 7,919,247; 7,964,580; 8,093,380; 8,114,997; 8,173,621; 8,334,270; 8,415,322; 8,481,713; 8,492,539; 8,551,973; 8,580,765; 8,618,076; 8,629,263; 8,633,309; 8,642,756; 8,716,262; 8,716,263; 8,735,345; 8,735,372; 8,735,569; 8,759,510 and 8,765,710); Hoffman La-Roche (U.S. Pat. No. 6,660,721), Roche (U.S. Pat. Nos. 6,784,166; 7,608,599, 7,608,601 and 8,071,567); Alios BioPharma Inc. (U.S. Pat. Nos. 8,895,723; 8,877,731; 8,871,737, 8,846,896, 8,772,474; 8,980,865; 9,012,427; US 2015/0105341; US 2015/0011497; US 2010/0249068; US2012/0070411; WO 2015/054465; WO 2014/209979; WO 2014/100505; WO 2014/100498; WO 2013/142159; WO 2013/142157; WO 2013/096680; WO 2013/088155; WO 2010/108135), Enanta Pharmaceuticals (U.S. Pat. Nos. 8,575,119; 8,846,638; 9,085,599; WO 2013/044030; WO 2012/125900), Biota (U.S. Pat. Nos. 7,268,119; 7,285,658; 7,713,941; 8,119,607; 8,415,309; 8,501,699 and 8,802,840), Biocryst Pharmaceuticals (U.S. Pat. Nos. 7,388,002; 7,429,571; 7,514,410; 7,560,434; 7,994,139; 8,133,870; 8,163,703; 8,242,085 and 8,440,813), Alla Chem, LLC (8,889,701 and WO 2015/053662), Inhibitex (8,759,318 and WO/2012/092484), Janssen Products (U.S. Pat. Nos. 8,399,429; 8,431,588, 8,481,510, 8,552,021, 8,933,052; 9,006,29 and 9,012,428) the University of Georgia Foundation (U.S. Pat. Nos. 6,348,587; 7,307,065; 7,662,938; 8,168,583; 8,673,926, 8,816,074; 8,921,384 and 8,946,244), RFS Pharma, LLC (U.S. Pat. Nos. 8,895,531; 8,859,595; 8,815,829; 8,609,627; 7,560,550; US 2014/0066395; US 2014/0235566; US 2010/0279969; WO/2010/091386 and WO 2012/158811) University College Cardiff Consultants Limited (WO/2014/076490, WO 2010/081082; WO/2008/062206), Achillion Pharmaceuticals, Inc. (WO/2014/169278 and WO 2014/169280), Cocrystal Pharma, Inc. (U.S. Pat. No. 9,173,893), Katholieke Universiteit Leuven (WO 2015/158913), Catabasis (WO 2013/090420) and the Regents of the University of Minnesota (WO 2006/004637).

Atea Pharmaceuticals, Inc. has disclosed β-D-2'-deoxy-2'-α-fluoro-2'-β-C-substituted-2-modified-$N^6$-(mono- and di-methyl) purine nucleotides for the treatment of HCV in U.S. Pat. No. 9,828,410 and PCT Application No. WO 2016/144918. Atea has also disclosed β-D-2'-deoxy-2'-substituted-4'-substituted-2-$N^6$-substituted-6-aminopurine nucleotides for the treatment of paramyxovirus and orthomyxovirus infections in US 2018/0009836 and WO 2018/009623.

There remains a strong medical need to develop anti-HCV therapies that are safe, effective and well-tolerated. The need is accentuated by the expectation of drug resistance. More potent direct-acting antivirals could significantly shorten treatment duration and improve compliance and SVR (sustained viral response) rates for patients infected with all HCV genotypes.

It is therefore an object of the present invention to provide compounds, pharmaceutical compositions, methods, and dosage forms to treat and/or prevent infections of HCV.

SUMMARY OF THE INVENTION

It has been surprisingly discovered that the hemisulfate salt of Compound 1, which is provided below as Compound 2, exhibits unexpected advantageous therapeutic properties, including enhanced bioavailability and target organ selectivity, over its free base (Compound 1). These unexpected advantages could not have been predicted in advance. Compound 2 is thus a therapeutically superior composition of matter to administer in an effective amount to a host in need thereof, typically a human, for the treatment of hepatitis C. Compound 2 is referred to as the hemi-sulfate salt of isopropyl((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate. Compound 1 is disclosed in U.S. Pat. No. 9,828,410.

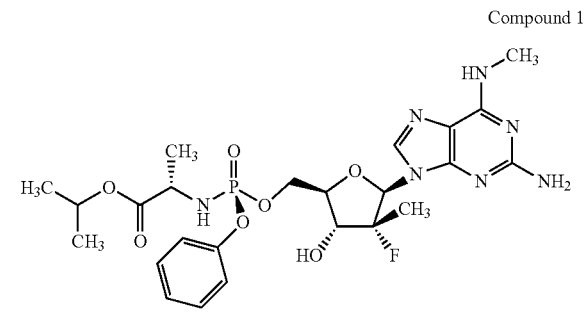 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

Compound 1

Compound 2

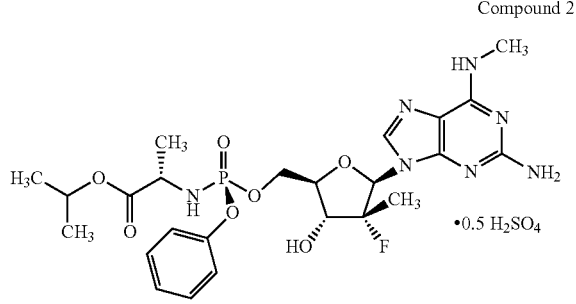 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

•0.5 H$_2$SO$_4$

Compound 2, as Compound 1, is converted to its corresponding triphosphate nucleotide (Compound 1-6) in the cell, which is the active metabolite and inhibitor of RNA polymerase (see Scheme 1 below). Since Compound 1-6 is produced in the cell and does not leave the cell, it is not measurable in the plasma. However, the 5'-OH metabolite Compound 1-7 (see Scheme 1) is exported from the cell, and therefore is measurable in plasma and acts as a surrogate of the concentration of intracellular active metabolite Compound 1-6.

It has been discovered that the plasma concentration in vivo of surrogate Compound 1-7, and thus intracellular Compound 1-6, is substantially higher when Compound 2 is administered in vivo than when Compound 1 is administered in vivo. In a head-to-head comparison of dogs dosed with Compound 1 and Compound 2 (Example 19, Table 28), dosing with Compound 2 achieved an AUC$_{(0-4hrs)}$ of the ultimate guanine 5'-OH nucleoside metabolite (1-7) that is twice as high as the AUC following Compound 1 dosing. It is unexpected that a non-covalent salt has such an effect on plasma concentration of the parent drug (Compound 1).

Additionally, Compound 2 selectively partitions in vivo to the liver over the heart (Example 19, Table 29), which is beneficial since the liver is the diseased organ in hosts infected with HCV. Dogs were dosed with Compound 1 or Compound 2 and the concentration of the active triphosphate (1-6) in the liver and heart was measured. The liver to heart ratio of the active triphosphate concentration was higher after dosing with Compound 2 compared to Compound 1 as shown in Table 29. Specifically, the liver/heart partitioning ratio for Compound 2 is 20 compared to a liver/heart partitioning ratio of 3.1 for Compound 1. This data indicates, unexpectedly, that the administration of Compound 2 results in the preferential distribution of the active guanine triphosphate (Compound 1-6) in the liver over the heart when compared to Compound 1, which reduces potential off-target effects. It was unexpected that administration of Compound 2 would significantly reduce undesired off-target partitioning. This allows for the administration of Compound 2 at a higher dose than Compound 1, if desired by the healthcare practitioner.

In addition, liver and heart tissue levels of the active guanine triphosphate derivative of Compound 2 (metabolite 1-6) were measured after oral doses of Compound 2 in rats and monkeys (Example 20). High levels of the active guanine triphosphate (1-6) were measured in the liver of all species tested. Importantly, unquantifiable levels of the guanine triphosphate (1-6) were measured in monkey hearts, and this is indicative of liver-specific formation of the active triphosphate. It was thus discovered that compared to Compound 1 dosing, Compound 2 dosing improves guanine triphosphate (1-6) distribution.

When administered to healthy and hepatitis C infected patients, Compound 2 was well tolerated after a single oral dose and C$_{max}$, T$_{max}$ and AUC$_{tot}$ pharmacokinetic parameters were comparable in both groups (Tables 34 and 35). As described in Example 24, a single dose of Compound 2 in HCV-infected patients resulted in a significant antiviral activity. Plasma exposure of metabolite 1-7 was mostly dose-proportional over the studied range.

Individual pharmacokinetic/pharmacodynamic analyses of patients dosed with Compound 2 showed that the viral response correlated with plasma exposure of metabolite 1-7 of Compound 2 (Example 24, FIGS. 23A-23F), indicating that profound vial responses are achievable with robust doses of Compound 2.

Example 24 confirms that, as non-limiting embodiments, single oral doses of 300 mg, 400 mg, and 600 mg result in significant antiviral activity in humans. The C$_{24}$ trough plasma concentration of metabolite 1-7 following a 600 mg dose of Compound 2 doubled from the C$_{24}$ trough plasma concentration of metabolite 1-7 following a 300 mg dose of Compound 2.

FIG. 24 and Example 25 highlight the striking invention provided by Compound 2 for the treatment of hepatitis C. As shown in FIG. 24, the steady-state trough plasma levels (C$_{24,ss}$) of metabolite 1-7 following Compound 2 dosing in humans (600 mg QD (550 mg free base equivalent) and 450 mg QD (400 mg free base equivalent)) was predicted and compared to the EC$_{95}$ of Compound 1 in vitro across a range of HCV clinical isolates to determine if the steady state plasma concentration is consistently higher than the EC$_{95}$, which would result in high efficacy against multiple clinical isolates in vivo. The EC$_{95}$ for Compound 1 is the same as the EC$_{95}$ of Compound 2. For Compound 2 to be effective, the steady-state trough plasma level of metabolite 1-7 should exceed the EC$_{95}$.

As shown in FIG. 24, the EC$_{95}$ of Compound 2 against all tested clinical isolates ranged from approximately 18 nM to 24 nM.

As shown in FIG. 24, Compound 2 at a dose of 450 mg QD (400 mg free base equivalent) in humans provides a predicted steady state trough plasma concentration (C$_{24,ss}$) of approximately 40 ng/mL. Compound 2 at a dose of 600 mg QD (550 mg free base equivalent) in humans provides a predicted steady state trough plasma concentration (C$_{24,ss}$) of approximately 50 ng/mL.

Therefore, the predicted steady state plasma concentration of surrogate metabolite 1-7 is almost double the EC$_{95}$ against all tested clinical isolates (even the hard to treat GT3a), which indicates superior performance.

In contrast, the EC$_{95}$ of the standard of care nucleotide sofosbuvir (Sovaldi) ranges from 50 nM to 265 nM across all tested HCV clinical isolates, with an EC$_{95}$ less than the predicted steady state concentration at the commercial dosage of 400 mg for only two isolates, GT2a and GT2b. The EC$_{95}$ for the commercial dosage of 400 mg of sofosbuvir is greater than the predicted steady state concentration for other clinical isolates, GT1a, GT1b, GT3a, GT4a, and GT4d.

The data comparing the efficacy and pharmacokinetic steady state parameters in FIG. 24 clearly demonstrates the unexpected therapeutic importance of Compound 2 for the treatment of hepatitis C. In fact, the predicted steady-state (C$_{24,ss}$) plasma level after administration of Compound 2 is predicted to be at least 2-fold higher than the EC$_{95}$ for all genotypes tested, and is 3- to 5-fold more potent against GT2. This data indicates that Compound 2 has potent pan-genotypic antiviral activity in humans. As shown in FIG. 24, the $EC_{95}$ of sofosbuvir against GT1, GT3, and GT4 is greater than 100 ng/mL. Thus surprisingly, Compound 2 is active against HCV at a dosage form that delivers a lower steady-state trough concentration (40-50 ng/mL) than the steady-state tough concentration (approximately 100 ng/mL) achieved by the equivalent dosage form of sofosbuvir.

In one embodiment, therefore, the invention includes a dosage form of Compound 2 that provides a metabolite 1-7 steady-state plasma trough concentration ($C_{24,ss}$) between approximately ng/mL, for example, 20-60 ng/mL, 25-50 ng/mL, 40-60 ng/mL, or even 40-50 ng/mL. This is unexpected in light of the fact that the steady state concentration of the equivalent metabolite of sofosbuvir is approximately 100 ng/mL.

Additionally, it has been discovered that Compound 2 is an unusually stable, highly soluble, non-hygroscopic salt with activity against HCV. This is surprising because a number of salts of Compound 1 other than the hemi-sulfate salt (Compound 2), including the mono-sulfate salt (Compound 3), are not physically stable, but instead deliquesce or become gummy solids (Example 4), and thus are not suitable for stable solid pharmaceutical dosage forms. Surprisingly, while Compound 2 does not become gummy, it is up to 43 times more soluble in water compared to Compound 1 and is over 6 times more soluble than Compound 1 under simulated gastric fluid (SGF) conditions (Example 15).

As discussed in Example 16, Compound 2 remains a white solid with an IR that corresponds to the reference standard for 6 months under accelerated stability conditions (40° C./75% RH). Compound 2 is stable for 9 months at ambient conditions (25° C./60% RH) and refrigerator conditions (5° C.).

Solid dosage forms (50 mg and 100 mg tablets) of Compound 2 are also chemically stable under accelerated (40° C./75% RH) and refrigeration conditions (5° C.) for 6 months (Example 26). Compound 2 is stable under ambient conditions (25° C./60% RH) in a solid dosage form for at least 9 months.

Scheme 1 provides the metabolic pathway of Compound 1 and Compound 2, which involves the initial de-esterification of the phosphoramidate (metabolite 1-1) to form metabolite 1-2. Metabolite 1-2 is then converted to the $N^6$-methyl-2,6-diaminopurine-5'-monophosphate derivative (metabolite 1-3), which is in turn metabolized to the free 5'-hydroxyl-$N^6$-methyl-2,6-diaminopurine nucleoside (metabolite 1-8) and ((2R,3R,4R,5R)-5-(2-amino-6-oxo-1,6-dihydro-9H-purin-9-yl)-4-fluoro-3-hydroxy-4-methyltetrahydrofuran-2-yl)methyl dihydrogen phosphate as the 5'-monophosphate (metabolite 1-4). Metabolite 1-4 is anabolized to the corresponding diphosphate (metabolite 1-5) and then the active triphosphate derivative (metabolite 1-6). The 5'-triphosphate can be further metabolized to generate 2-amino-9-((2R,3R,4R,5R)-3-fluoro-4-hydroxy-5-(hydroxymethyl)-3-methyltetrahydrofuran-2-yl)-1,9-dihydro-6H-purin-6-one (1-7). Metabolite 1-7 is measurable in plasma and is therefore a surrogate for the active triphosphate (1-6), which is not measurable in plasma.

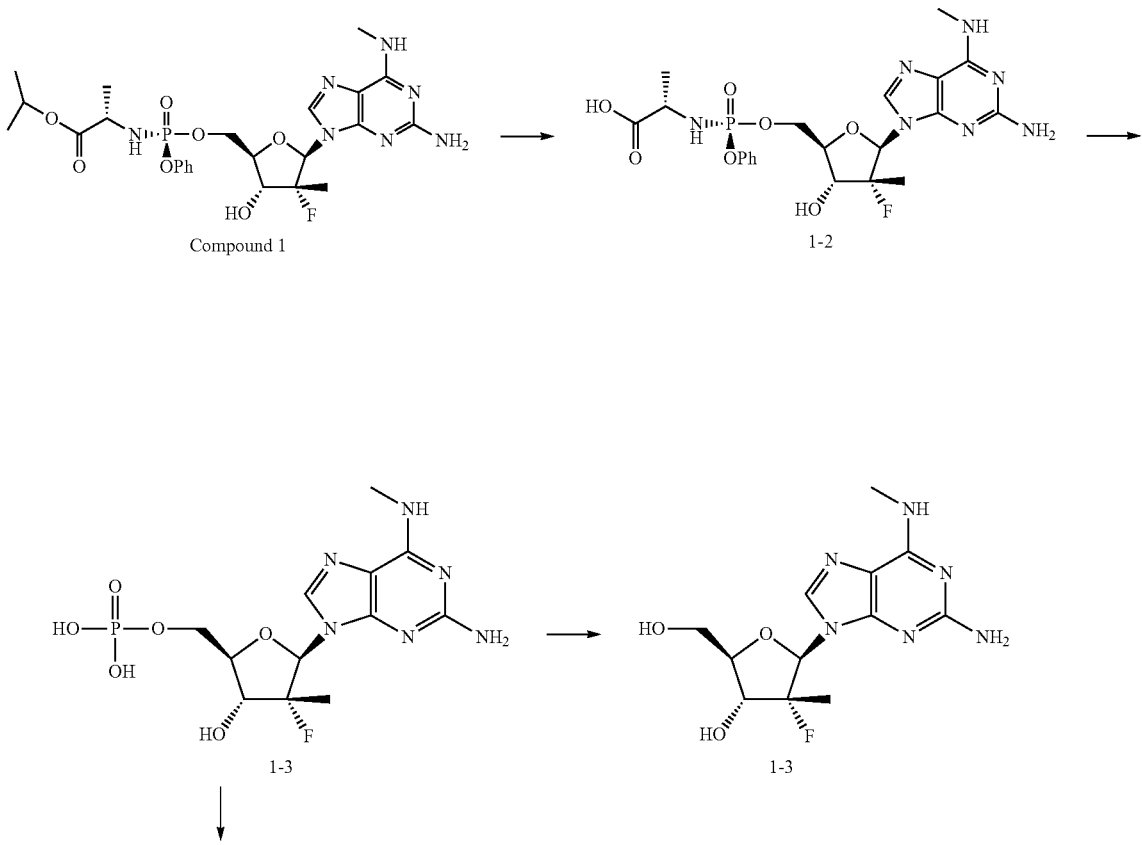

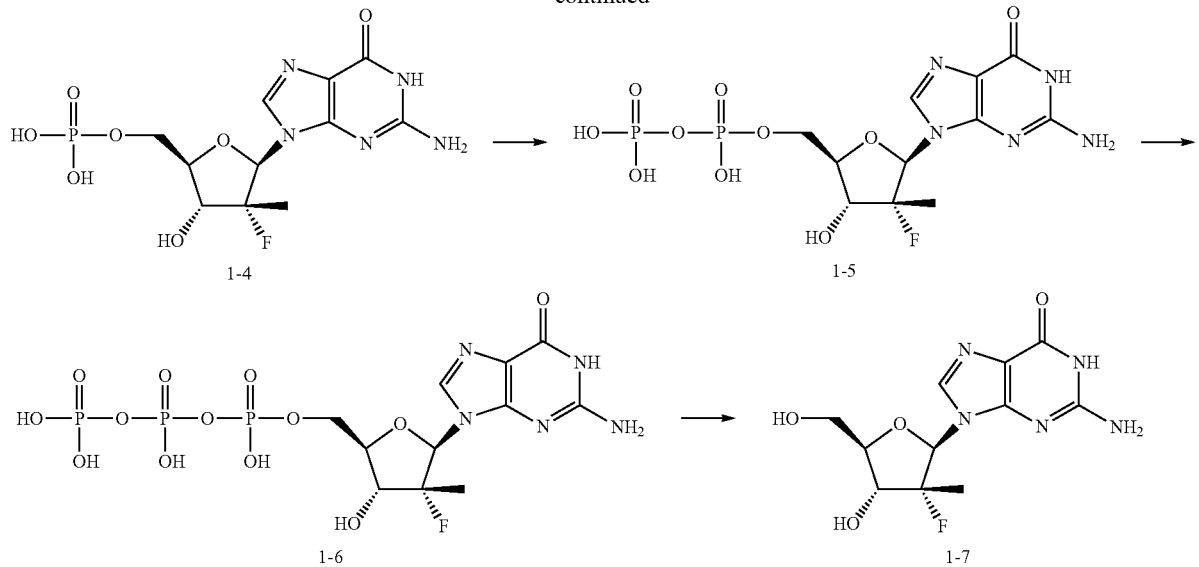

In one embodiment, the invention is Compound 2 and its use to treat hepatitis C (HCV) in a host in need thereof, optionally in a pharmaceutically acceptable carrier. In one aspect, Compound 2 is used as an amorphous solid. In another aspect, Compound 2 is used as a crystalline solid.

The present invention further includes an exemplary on-limiting process for the preparation of Compound 2 that includes
  (i) a first step of dissolving Compound 1 in an organic solvent, for example, acetone, ethyl acetate, methanol, acetonitrile, or ether, or the like, in a flask or container;
  (ii) charging a second flask or container with a second organic solvent, which may be the same as or different from the organic solvent in step (i), optionally cooling the second solvent to 0-10 degrees C., and adding dropwise $H_2SO_4$ to the second organic solvent to create a $H_2SO_4$/organic solvent mixture; and wherein the solvent for example may be methanol;
  (iii) adding dropwise the $H_2SO_4$/solvent mixture at a molar ratio of 0.5/1.0 from step (ii) to the solution of Compound 1 of step (i) at ambient or slightly increased or decreased temperature (for example 23-35 degrees C.);
  (iv) stirring the reaction of step (iii) until precipitate of Compound 2 is formed, for example at ambient or slightly increased or decreased temperature;
  (v) optionally filtering the resulting precipitate from step (iv) and washing with an organic solvent; and
  (vi) optionally drying the resulting Compound 2 in a vacuum, optionally at elevated a temperature, for example, 55, 56, 57, 58, 59, or 60° C.

In one embodiment, the organic solvent in step (i) is 3-methyl-2-pentanone. In one embodiment, the organic solvent in step (i) is ethyl isopropyl ketone. In one embodiment, the organic solvent in step (i) is methyl propionate. In one embodiment, the organic solvent in step (i) is ethyl butyrate.

Despite the volume of antiviral nucleoside literature and patent filings, Compound 2 has not been specifically disclosed. Accordingly, the present invention includes Compound 2, or a pharmaceutically acceptable composition or dosage form thereof, as described herein.

Compounds, methods, dosage forms, and compositions are provided for the treatment of a host infected with a HCV virus via administration of an effective amount of Compound 2. In certain embodiments, Compound 2 is administered at a dose of at least about 100, 200, 250, 300, 350, 400, 450, 500, 550, 600, 650, 700,750, 800, 850, 900, 950, or 1000 mg. In certain embodiments, Compound 2 is administered for up to 12 weeks, for up to 10 weeks, for up to 8 weeks, for up to 6 weeks, or for up to 4 weeks. In alternative embodiments, Compound 2 is administered for at least 4 weeks, for at least 6 weeks, for at least 8 weeks, for at least 10 weeks, or for at least 12 weeks. In certain embodiments, Compound 2 is administered at least once a day or every other day. In certain embodiments, Compound 2 is administered in a dosage form that achieves a steady-state trough plasma level ($C_{24,ss}$) of metabolite 1-7 between approximately 15-ng/mL. In one embodiment, Compound 2 is administered in a dosage form that achieves a steady-state trough plasma level ($C_{24,ss}$) of metabolite 1-7 between approximately 20-60 ng/mL. In certain embodiments, Compound 2 is administered in a dosage form that achieves an AUC of metabolite 1-7 between approximately 1,200 ng*h/mL and 3,000 ng*h/mL. In one embodiment, Compound 2 is administered in a dosage form that achieves an AUC of metabolite 1-7 between approximately 1,500 and 2,100 ng*h/mL.

The compounds, compositions, and dosage forms can also be used to treat related conditions such as anti-HCV antibody positive and antigen positive conditions, viral-based chronic liver inflammation, liver cancer resulting from advanced hepatitis C (hepatocellular carcinoma (HCC)), cirrhosis, chronic or acute hepatitis C, fulminant hepatitis C, chronic persistent hepatitis C and anti-HCV-based fatigue. The compound or formulations that include the compounds can also be used prophylactically to prevent or restrict the progression of clinical illness in individuals who are anti-HCV antibody- or antigen-positive or who have been exposed to hepatitis C.

The present invention thus includes the following features:
  (a) Compound 2 as described herein;
  (b) Prodrugs of Compound 2

(c) Use of Compound 2 in the manufacture of a medicament for treatment of a hepatitis C virus infection;

(d) Compound 2 for use to treat hepatitis C, optionally in a pharmaceutically acceptable carrier;

(e) A method for manufacturing a medicament intended for the therapeutic use for treating a hepatitis C virus infection, characterized in that Compound 2, or a pharmaceutically acceptable salt, as described herein is used in the manufacture;

(e) A pharmaceutical formulation comprising an effective host-treating amount of Compound 2 with a pharmaceutically acceptable carrier or diluent;

(f) Processes for the preparation of therapeutic products that contain an effective amount of Compound 2;

(g) Solid dosage forms, including those that provide an advantageous pharmacokinetic profile; and (h) Processes for the manufacture of Compound 2, as described herein.

DETAILED DESCRIPTION OF THE INVENTION

Figure 1A:
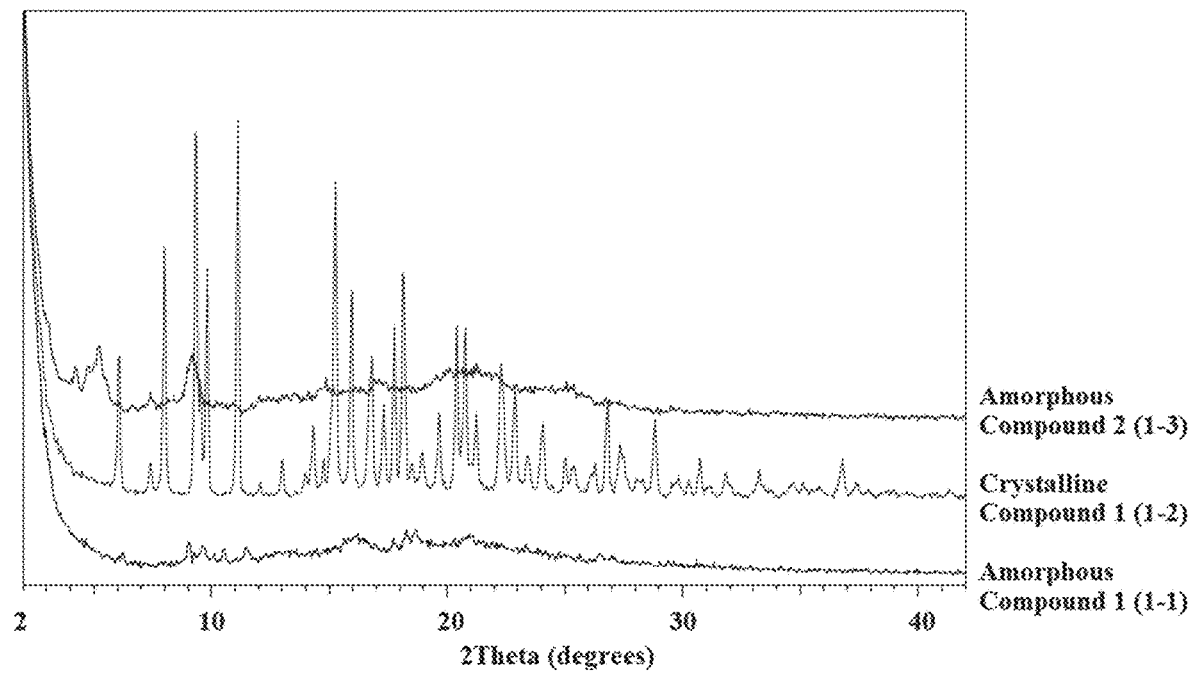
FIG. 1A is an overlay of XRPD diffractograms of samples 1-1 (amorphous Compound 1), 1-2 (crystalline Compound 1), and 1-3 (amorphous Compound 2) prior to stability studies for characterization purposes as described in Example 2 and Example 5. The x-axis is 2Theta measured in degrees and the y-axis is intensity measured in counts.

The invention disclosed herein is a compound, method, composition, and solid dosage form for the treatment of infections in or exposure to humans and other host animals of the HCV virus that includes the administration of an effective amount of the hemi-sulfate salt of isopropyl((S)-(((2R,3R,4R,5R)-5-(2-amino-6-(methylamino)-9H-purin-9-yl)-4-fluoro-3-hydroxy-4-methyltetrahydrofuran-2-yl) methoxy)(phenoxy)phosphoryl)-L-alaninate (Compound 2) as described herein, optionally in a pharmaceutically acceptable carrier. In one embodiment, Compound 2 is an amorphous solid. In yet another embodiment, Compound 2 is a crystalline solid.

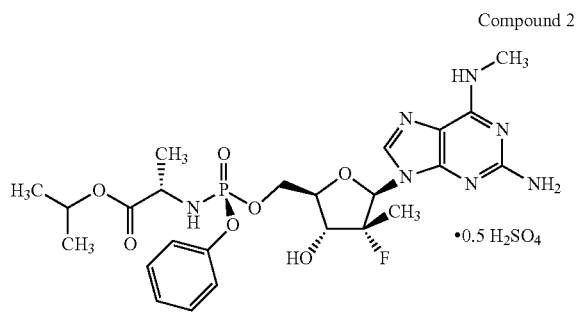 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

Compound 2

The compound, compositions, and dosage forms can also be used to treat conditions related to or occurring as a result of an HCV viral exposure. For example, the active compound can be used to treat HCV antibody positive- and HCV antigen-positive conditions, viral-based chronic liver inflammation, liver cancer resulting from advanced hepatitis C (e.g., hepatocellular carcinoma), cirrhosis, acute hepatitis C, fulminant hepatitis C, chronic persistent hepatitis C, and anti-HCV-based fatigue.

The active compounds and compositions can also be used to treat the range of HCV genotypes. At least six distinct genotypes of HCV, each of which have multiple subtypes, have been identified globally. Genotypes 1-3 are prevalent worldwide, and Genotypes 4, 5, and 6 are more limited geographically. Genotype 4 is common in the Middle East and Africa. Genotype 5 is mostly found in South Africa. Genotype 6 predominately exists in Southeast Asia. Although the most common genotype in the United States is Genotype 1, defining the genotype and subtype can assist in treatment type and duration. For example, different genotypes respond differently to different medications and optimal treatment times vary depending on the genotype infection. Within genotypes, subtypes, such as Genotype 1a and Genotype 1b, respond differently to treatment as well. Infection with one type of genotype does not preclude a later infection with a different genotype.

As described in Example 22, Compound 2 is active against the range of HCV genotypes, including Genotypes 1-5. In one embodiment, Compound 2 is used to treat HCV Genotype 1, HCV Genotype 2, HCV Genotype 3, HCV Genotype 4, HCV Genotype 5, or HCV Genotype 6. In one embodiment, Compound 2 is used to treat HCV Genotype 1a. In one embodiment, Compound 2 is used to treat HCV Genotype 1b. In one embodiment, Compound 2 is used to treat HCV Genotype 2a. In one embodiment, Compound 2 is used to treat HCV Genotype 2b. In one embodiment, Compound 2 is used to treat HCV Genotype 3a. In one embodiment, Compound 2 is used to treat HCV Genotype 4a. In one embodiment, Compound 2 is used to treat HCV Genotype 4d.

In one embodiment, Compound 1 or Compound 2 is used to treat HCV Genotype 5a. In one embodiment, Compound 1 or Compound 2 is used to treat HCV Genotype 6a. In one embodiment, Compound 1 or Compound 2 is used to treat HCV Genotype 6b, 6c, 6d, 6e, 6f, 6g, 6h, 6i, 6j, 6k, 6l, 6 m, 6n, 6o, 6p, 6q, 6r, 6s, 6t, or 6u.

Figure 24:
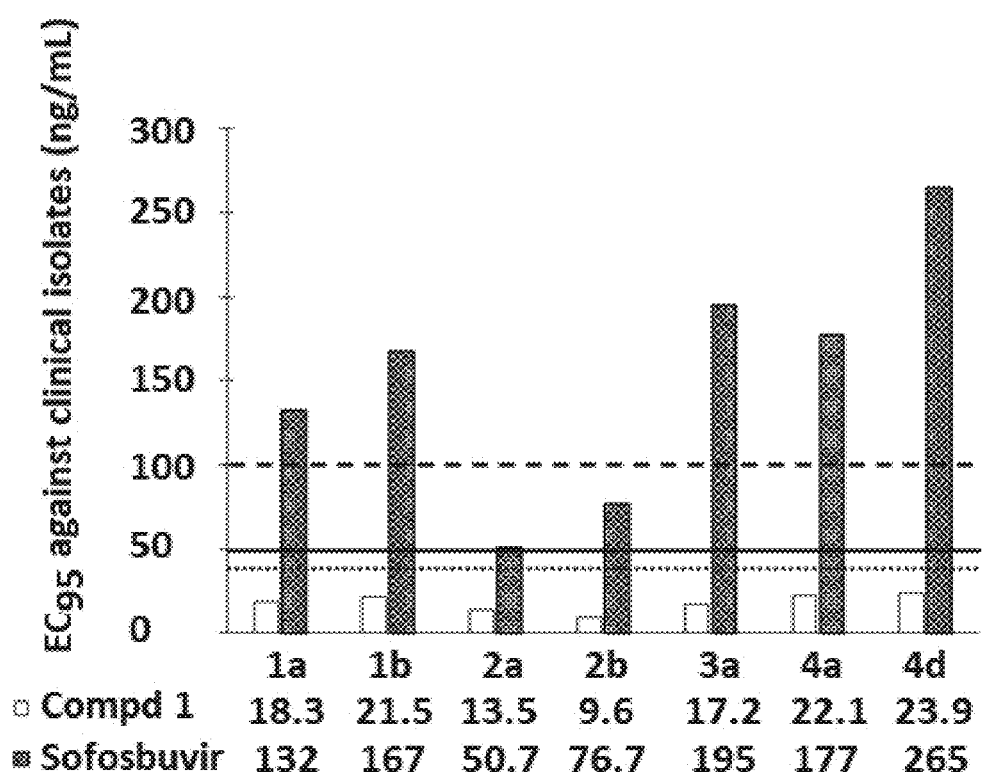
FIG. 24 is a graph of the $EC_{95}$ values of Compound 1 and sofosbuvir against clinical isolates of GT1, GT2, GT3, and GT4 HCV-infected patients. The dashed horizontal line (- - - - -) represents the steady-state trough concentration ($C_{24,ss}$) of sofosbuvir nucleoside following a dose of 400 mg QD of sofosbuvir. The full horizontal line (-) represents the steady-state trough concentration ($C_{24,ss}$) of metabolite 1-7 following 600 mg of Compound 2 (equivalent to 550 mg of Compound 1). The dotted horizontal line (---------) represents the steady-state trough concentration ($C_{24,ss}$) of metabolite 1-7 following 450 mg of Compound 2 (equivalent to 400 mg of Compound 1). As discussed in Example 25, the predicted steady-state trough plasma level ($C_{24,ss}$) of metabolite 1-7 following 600 mg and 450 mg of Compound 2 exceeds the in vitro $EC_{95}$ of Compound 1 against all tested clinical isolates. The steady state trough plasma level ($C_{24,ss}$) of sofosbuvir only exceeds the $EC_{95}$ at GT2 clinical isolates. The x-axis is labeled with the clinical isolates and the table under the x-axis lists the $EC_{95}$ values for Compound 1 and sofosbuvir. The y-axis is the $EC_{95}$ against the clinical isolates measured in ng/mL. $EC_{95}$ is expressed as nucleoside equivalent. Sofosbuvir and Compound 2 were administered daily (QD).

As discussed in Example 25 and shown in FIG. 24, the predicted steady-state trough concentration ($C_{24,ss}$) of metabolite 1-7 following a dose of 450 mg (400 mg free base) and a dose of 600 mg (550 mg free base) of Compound 2 is approximately 40 ng/mL to 50 ng/mL. This $C_{24,ss}$ level exceeded the $EC_{95}$ of Compound 1 at HCV Genotypes 1a, 1b, 2a, 2b, 3a, 4a, and 4d. This data confirms that Compound 2 has potent-pan genotypic activity. This is surprising because Compound 2 achieves a smaller steady-state trough concentration ($C_{24,ss}$) than the steady-state trough concentration ($C_{24,ss}$) of the nucleoside metabolite of sofosbuvir following equivalent sofosbuvir dosing. The steady-state trough concentration ($C_{24,ss}$) of the corresponding nucleoside metabolite of sofosbuvir is approximately 100 ng/mL, but this level only exceeds the $EC_{95}$ of sofosbuvir against GT2 clinical isolates (FIG. 24). Compound 2 is more potent than sofosbuvir against GT1, GT2, GT3, and GT4, and therefore allows a dosage form that delivers a smaller steady-state trough concentration of its metabolite which is nonetheless efficacious against all tested genotypes of HCV. In one embodiment, a dosage form of Compound 2 is delivered that achieves a metabolite 1-7 steady-state trough concentration ($C_{24,ss}$) between approximately 15-75 ng/mL. In one embodiment, a dosage form of Compound 2 is delivered that achieves a metabolite 1-7 steady-state trough concentration ($C_{24,ss}$) between approximately 20-60 ng/mL, 20-50 ng/mL, or 20-40 ng/mL.

In one embodiment, the compound, formulations, or solid dosage forms that include the compound can also be used prophylactically to prevent or retard the progression of clinical illness in individuals who are HCV antibody- or HCV antigen-positive or who have been exposed to hepatitis C.

In particular, it has been discovered that Compound 2 is active against HCV and exhibits superior drug-like and pharmacological properties compared to its free base (Compound 1). Surprisingly, Compound 2 is more bioavailable and achieves a higher AUC than Compound 1 (Example 19) and Compound 2 is more selective for the target organ, the liver, than Compound 1 (Example 19).

Compound 2 is also advantageous over Compound 1 in terms of solubility and chemical stability. This is surprising because the mono-sulfate salt of isopropyl((S)-(((2R,3R,4R,5R)-5-(2-amino-6-(methyl amino)-9H-purin-9-yl)-4-fluoro-3-hydroxy-4-methyltetrahydrofuran-2-yl)methoxy)(phenoxy)phosphoryl)-L-alaninate (Compound 3) is unstable and exhibits the appearance of a sticky gum, while Compound 2, the hemi-sulfate salt, is a stable white solid. The hemisulfate salt, both as a solid and in a solid dosage form, is very stable over 9 months and is not hydroscopic.

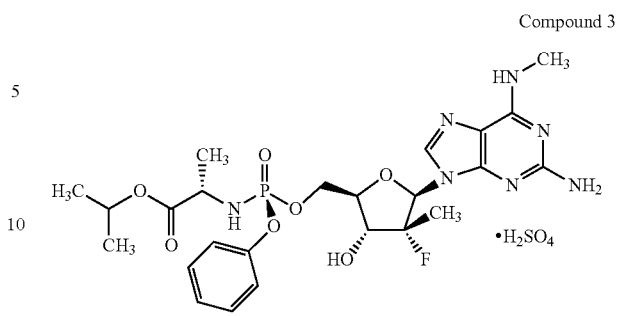

Compound 3

Despite the volume of antiviral nucleoside literature and patent filings, Compound 2 has not been specifically disclosed.

Figure 3:
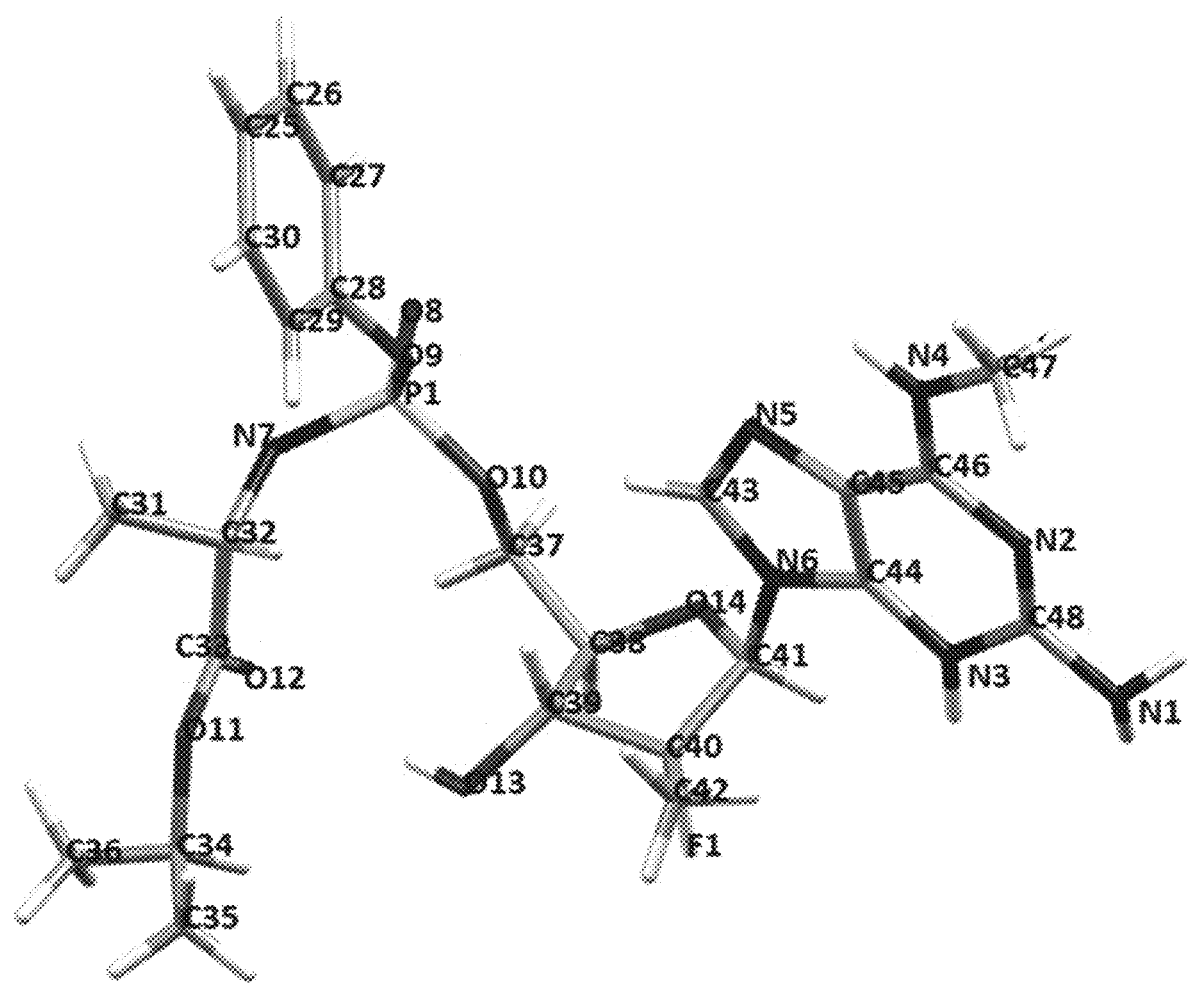
FIG. 3 is an X-ray crystallography image of Compound 1 showing the absolute stereochemistry as described in Example 2.

Compound 2 has S-stereochemistry at the phosphorus atom which has been confirmed with X-ray crystallography (FIG. 3, Example 2). In alternative embodiments, Compound 2 can be used in the form of any desired ratio of phosphorus R- and S-enantiomers, including up to pure enantiomers. In some embodiments, Compound 2 is used in a form that is at least 90% free of the opposite enantiomer, and can be at least 98%, 99%, or even 100% free of the opposite enantiomer. Unless described otherwise, an enantiomerically enriched Compound 2 is at least 90% free of the opposite enantiomer. In addition, in an alternative embodiment, the amino acid of the phosphoramidate can be in the D- or L-configuration, or a mixture thereof, including a racemic mixture.

Unless otherwise specified, the compounds described herein are provided in the β-D-configuration. In an alternative embodiment, the compounds can be provided in a β-L-configuration. Likewise, any substituent group that exhibits chirality can be provided in racemic, enantiomeric, diastereomeric form, or any mixture thereof. Where a phosphoramidate exhibits chirality, it can be provided as an R or S chiral phosphorus derivative or a mixture thereof, including a racemic mixture. All of the combinations of these stereo configurations are alternative embodiments in the invention described herein. In another embodiment, at least one of the hydrogens of Compound 2 (the nucleotide or the hemi-sulfate salt) can be replaced with deuterium.

These alternative configurations include, but are not limited to,

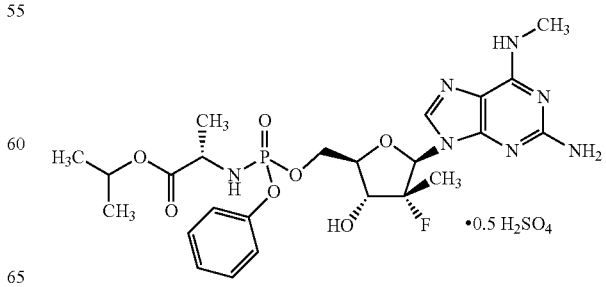

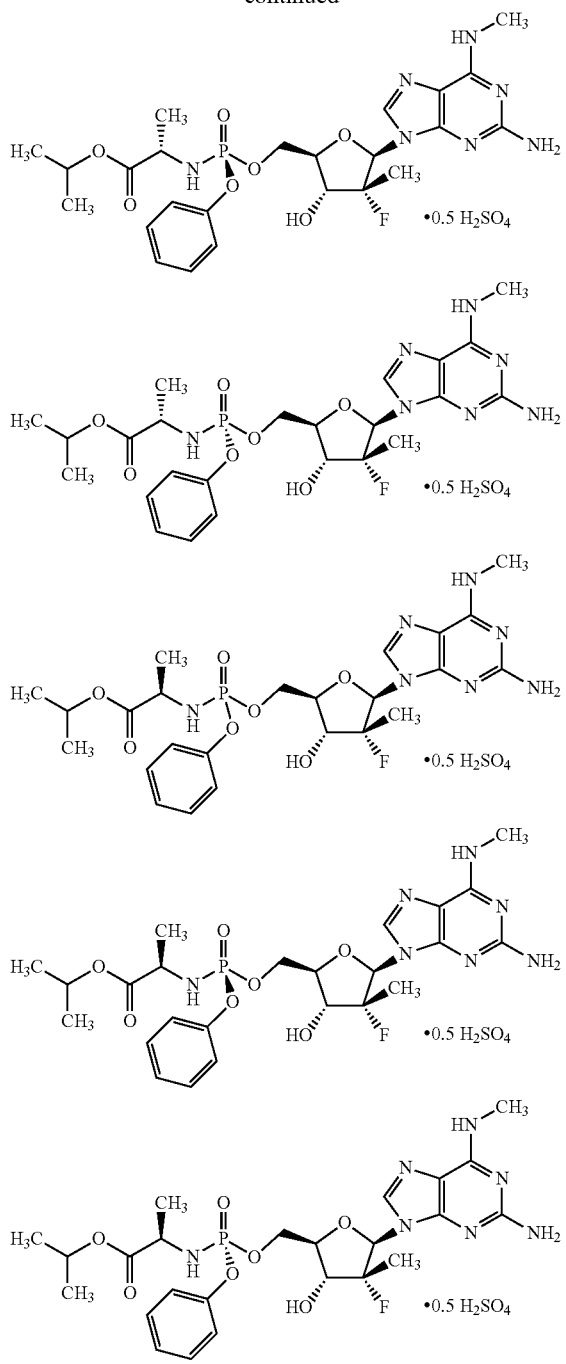

I. Hemi-sulfate salt of isopropyl((S)-(((2R,3R,4R, 5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate (Compound 2)

The active compound of the invention is Compound 2, which can be provided in a pharmaceutically acceptable composition or solid dosage form thereof. In one embodiment, Compound 2 is an amorphous solid. In yet a further embodiment, Compound 2 is a crystalline solid.

Synthesis of Compound 2

The present invention further includes a non-limiting illustrative process for the preparation of Compound 2 that includes
(i) a first step of dissolving Compound 1 in an organic solvent, for example, acetone, ethyl acetate, methanol, acetonitrile, or ether, or the like, in a flask or container;
(ii) charging a second flask or container with a second organic solvent, which may be the same as or different from the organic solvent in step (i), optionally cooling the second solvent to 0-10 degrees C., and adding dropwise $H_2SO_4$ to the second organic solvent to create a $H_2SO_4$/organic solvent mixture; and wherein the solvent for example may be methanol;
(iii) adding dropwise the $H_2SO_4$/solvent mixture at a molar ratio of 0.5/1.0 from step (ii) to the solution of Compound 1 of step (i) at ambient or slightly increased or decreased temperature (for example 23-35 degrees C.);
(iv) stirring the reaction of step (iii) until precipitate of Compound 2 is formed, for example at ambient or slightly increased or decreased temperature;
(v) optionally filtering the resulting precipitate from step (iv) and washing with an organic solvent; and
(vi) optionally drying the resulting Compound 2 in a vacuum, optionally at elevated a temperature, for example, 55, 56, 57, 58, 59, or 60° C.

In certain embodiments, step (i) above is carried out in acetone. Further, the second organic solvent in step (ii) may be for example methanol and the mixture of organic solvents in step (v) is methanol/acetone.

In one embodiment, Compound 1 is dissolved in ethyl acetate in step (i). In one embodiment, Compound 1 is dissolved in tetrahydrofuran in step (i). In one embodiment, Compound 1 is dissolved in acetonitrile in step (i). In an additional embodiment, Compound 1 is dissolved in dimethylformamide in step (i).

In one embodiment, the second organic solvent in step (ii) is ethanol. In one embodiment, the second organic solvent in step (ii) is isopropanol. In one embodiment, the second organic solvent in step (ii) is n-butanol.

In one embodiment, a mixture of solvents are used for washing in step (v), for example, ethanol/acetone. In one embodiment, the mixture of solvent for washing in step (v) is isopropanol/acetone. In one embodiment, the mixture of solvent for washing in step (v) is n-butanol/acetone. In one embodiment, the mixture of solvent for washing in step (v) is ethanol/ethyl acetate. In one embodiment, the mixture of solvent for washing in step (v) is isopropanol/ethyl acetate. In one embodiment, the mixture of solvent for washing in step (v) is n-butanol/ethyl acetate. In one embodiment, the mixture of solvent for washing in step (v) is ethanol/tetrahydrofuran. In one embodiment, the mixture of solvent for washing in step (v) is isopropanol/tetrahydrofuran. In one embodiment, the mixture of solvent for washing in step (v) is n-butanol/tetrahydrofuran. In one embodiment, the mixture of solvent for washing in step (v) is ethanol/acetonitrile. In one embodiment, the mixture of solvent for washing in step (v) is isopropanol/acetonitrile. In one embodiment, the mixture of solvent for washing in step (v) is n-butanol/acetonitrile. In one embodiment, the mixture of solvent for washing in step (v) is ethanol/dimethylformamide. In one embodiment, the mixture of solvent for washing in step (v) is isopropanol/dimethylformamide. In one embodiment, the mixture of solvent for washing in step (v) is n-butanol/dimethylformamide.

II. Metabolism of Isopropyl((S)-(42R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate (Compound 2)

The metabolism of Compound 1 and Compound 2 involves the production of a 5'-monophosphate and the subsequent anabolism of the $N^6$-methyl-2,6-diaminopurine base (1-3) to generate ((2R,3R,4R,5R)-5-(2-amino-6-oxo-1,6-dihydro-9H-purin-9-yl)-4-fluoro-3-hydroxy-4-methyltetrahydrofuran-2-yl)methyl dihydrogen phosphate (1-4) as the 5'-monophosphate. The monophosphate is then further anabolized to the active triphosphate species: the 5'-triphosphate (1-6). The 5'-triphosphate can be further metabolized to generate 2-amino-9-((2R,3R,4R,5R)-3-fluoro-4-hydroxy-5-(hydroxymethyl)-3-methyltetrahydrofuran-2-yl)-1,9-dihydro-6H-purin-6-one (1-7). Alternatively, 5'-monophophate 1-2 can be metabolized to generate the purine base 1-8. The metabolic pathway for isopropyl((S)-(((2R,3R,4R,5R)-5-(2-amino-6-(methyl amino)-9H-purin-9-yl)-4-fluoro-3-hydroxy-4-methyltetrahydrofuran-2-yl)methoxy)(phenoxy)phosphoryl)-L-alaninate is illustrated in Scheme 1 (shown above).

III. Additional Salts of Compound 1

In alternative embodiments, the present invention provides Compound 1 as an oxalate salt (Compound 4) or an HCl salt (Compound 5).

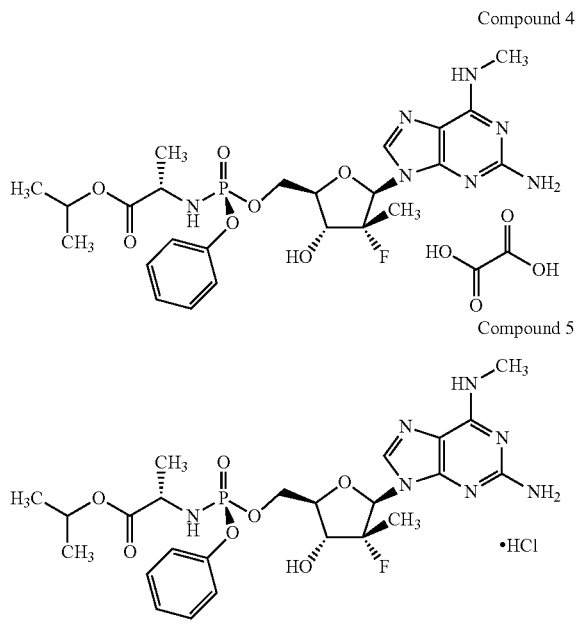

Compound 4

Compound 5

Both the 1:1 oxalate salt and the 1:1 HCl salt form solids with reasonable properties for solid dosage forms for the treatment of a host such as a human with hepatitis C. However, the oxalate salt may be less desired, and perhaps not suitable, if the patient is susceptible to kidney stones. The HCl salt is more hydroscopic than the hemisulfate salt. Thus, the hemisulfate salt remains the most desired salt form of Compound 1 with unexpected properties.

IV. Definitions

The term "D-configuration" as used in the context of the present invention refers to the principle configuration which mimics the natural configuration of sugar moieties as opposed to the unnatural occurring nucleosides or "L" configuration. The term "β" or "β anomer" is used with reference to nucleoside analogs in which the nucleoside base is configured (disposed) above the plane of the furanose moiety in the nucleoside analog.

The terms "coadminister" and "coadministration" or combination therapy are used to describe the administration of Compound 2 according to the present invention in combination with at least one other active agent, for example where appropriate at least one additional anti-HCV agent. The timing of the coadministration is best determined by the medical specialist treating the patient. It is sometimes preferred that the agents be administered at the same time. Alternatively, the drugs selected for combination therapy may be administered at different times to the patient. Of course, when more than one viral or other infection or other condition is present, the present compounds may be combined with other agents to treat that other infection or condition as required.

The term "host", as used herein, refers to a unicellular or multicellular organism in which a HCV virus can replicate, including cell lines and animals, and typically a human. The term host specifically refers to infected cells, cells transfected with all or part of a HCV genome, and animals, in particular, primates (including chimpanzees) and humans. In most animal applications of the present invention, the host is a human patient. Veterinary applications, in certain indications, however, are clearly anticipated by the present invention (such as chimpanzees). The host can be for example, bovine, equine, avian, canine, feline, etc.

Isotopic Substitution

The present invention includes compounds and the use of compound 2 with desired isotopic substitutions of atoms at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2H$) and tritium ($^3H$) may be used anywhere in described structures. Alternatively or in addition, isotopes of carbon, e.g., $^{13}C$ and $^{14}C$, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect). Achillion Pharmaceuticals, Inc. (WO/2014/169278 and WO/2014/169280) describes deuteration of nucleotides to improve their pharmacokinetic or pharmacodynamic, including at the 5-position of the molecule.

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break-down can reduce the rate of or eliminate the metabolism at that bond. At any position of the compound that a hydrogen atom may be present, the hydrogen atom can be any isotope of hydrogen, including protium ($^1H$), deuterium ($^2H$) and tritium ($^3H$). Thus, reference herein to a compound encompasses all potential isotopic forms unless the context clearly dictates otherwise.

The term "isotopically-labeled" analog refers to an analog that is a "deuterated analog", a "$^{13}C$-labeled analog," or a "deuterated/$^{13}C$-labeled analog." The term "deuterated analog" means a compound described herein, whereby a H-isotope, i.e., hydrogen/protium ($^1$H), is substituted by a H-isotope, i.e., deuterium ($^2$H). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location. Unless indicated to the contrary, the deuteration is at least 80% at the selected location. Deuteration of the nucleoside can occur at any replaceable hydrogen that provides the desired results.

V. Methods of Treatment or Prophylaxis

Treatment, as used herein, refers to the administration of Compound 2 to a host, for example a human that is or may become infected with a HCV virus.

The term "prophylactic" or preventative, when used, refers to the administration of Compound 2 to prevent or reduce the likelihood of an occurrence of the viral disorder. The present invention includes both treatment and prophylactic or preventative therapies. In one embodiment, Compound 2 is administered to a host who has been exposed to and thus is at risk of infection by a hepatitis C virus infection.

The invention is directed to a method of treatment or prophylaxis of a hepatitis C virus, including drug resistant and multidrug resistant forms of HCV and related disease states, conditions, or complications of an HCV infection, including cirrhosis and related hepatotoxicities, as well as other conditions that are secondary to a HCV infection, such as weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, jaundice, and hepatocellular cancer, among others. The method comprises administering to a host in need thereof, typically a human, with an effective amount of Compound 2 as described herein, optionally in combination with at least one additional bioactive agent, for example, an additional anti-HCV agent, further in combination with a pharmaceutically acceptable carrier additive and/or excipient.

In yet another aspect, the present invention is a method for prevention or prophylaxis of an HCV infection or a disease state or related or follow-on disease state, condition or complication of an HCV infection, including cirrhosis and related hepatotoxicities, weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, jaundice, and hepatocellular (liver) cancer, among others, said method comprising administering to a patient at risk with an effective amount Compound 2 as described above in combination with a pharmaceutically acceptable carrier, additive, or excipient, optionally in combination with another anti-HCV agent. In another embodiment, the active compounds of the invention can be administered to a patient after a hepatitis-related liver transplantation to protect the new organ.

In an alternative embodiment, Compound 2 is provided as the hemisulfate salt of a phosphoramidate of Compound 1 other than the specific phosphoramidate described in the compound illustration. A wide range of phosphoramidates are known to those skilled in the art that include various esters and phospho-esters, any combination of which can be used to provide an active compound as described herein in the form of a hemisulfate salt.

VI. Pharmaceutical Compositions and Dosage Forms

In an aspect of the invention, pharmaceutical compositions according to the present invention comprise an anti-HCV virus effective amount of Compound 2 as described herein, optionally in combination with a pharmaceutically acceptable carrier, additive, or excipient, further optionally in combination or alternation with at least one other active compound. In one embodiment, the invention includes a solid dosage form of Compound 2 in a pharmaceutically acceptable carrier.

In an aspect of the invention, pharmaceutical compositions according to the present invention comprise an anti-HCV effective amount of Compound 2 described herein, optionally in combination with a pharmaceutically acceptable carrier, additive, or excipient, further optionally in combination with at least one other antiviral agent, such as an anti-HCV agent.

The invention includes pharmaceutical compositions that include an effective amount to treat a hepatitis C virus infection of Compound 2 of the present invention or prodrug, in a pharmaceutically acceptable carrier or excipient. In an alternative embodiment, the invention includes pharmaceutical compositions that include an effective amount to prevent a hepatitis C virus infection of Compound 2 of the present invention or prodrug, in a pharmaceutically acceptable carrier or excipient.

One of ordinary skill in the art will recognize that a therapeutically effective amount will vary with the infection or condition to be treated, its severity, the treatment regimen to be employed, the pharmacokinetic of the agent used, as well as the patient or subject (animal or human) to be treated, and such therapeutic amount can be determined by the attending physician or specialist.

Compound 2 according to the present invention can be formulated in a mixture with a pharmaceutically acceptable carrier. In general, it is preferable to administer the pharmaceutical composition in orally-administrable form, an in particular, a solid dosage form such as a pill or tablet. Certain formulations may be administered via a parenteral, intravenous, intramuscular, topical, transdermal, buccal, subcutaneous, suppository, or other route, including intranasal spray. Intravenous and intramuscular formulations are often administered in sterile saline. One of ordinary skill in the art may modify the formulations to render them more soluble in water or another vehicle, for example, this can be easily accomplished by minor modifications (salt formulation, esterification, etc.) that are well within the ordinary skill in the art. It is also well within the routineers' skill to modify the route of administration and dosage regimen of Compound 2 in order to manage the pharmacokinetic of the present compounds for maximum beneficial effect in patients, as described in more detail herein.

In certain pharmaceutical dosage forms, the prodrug form of the compounds, especially including acylated (acetylated or other), and ether (alkyl and related) derivatives, phosphate esters, thiophosphoramidates, phosphoramidates, and various salt forms of the present compounds, may be used to achieve the desired effect. One of ordinary skill in the art will recognize how to readily modify the present compounds to prodrug forms to facilitate delivery of active compounds to a targeted site within the host organism or patient. The person of ordinary skill in the art also will take advantage of favorable pharmacokinetic parameters of the prodrug forms, where applicable, in delivering the present compounds to a targeted site within the host organism or patient to maximize the intended effect of the compound.

The amount of Compound 2 included within the therapeutically active formulation according to the present invention is an effective amount to achieve the desired outcome according to the present invention, for example, for treating the HCV infection, reducing the likelihood of a HCV infection or the inhibition, reduction, and/or abolition of HCV or its secondary effects, including disease states, conditions, and/or complications which occur secondary to HCV. In general, a therapeutically effective amount of the present compound in a pharmaceutical dosage form may range from about 0.001 mg/kg to about 100 mg/kg per day or more, more often, slightly less than about 0.1 mg/kg to more than about 25 mg/kg per day of the patient or considerably more, depending upon the compound used, the condition or infection treated and the route of administration. Compound 2 is often administered in amounts ranging from about 0.1 mg/kg to about 15 mg/kg per day of the patient, depending upon the pharmacokinetic of the agent in the patient. This dosage range generally produces effective blood level concentrations of active compound which may range from about 0.001 to about 100, about 0.05 to about 100 micrograms/cc of blood in the patient.

Often, to treat, prevent or delay the onset of these infections and/or to reduce the likelihood of an HCV virus infection, or a secondary disease state, condition or complication of HCV, Compound 2 will be administered in a solid dosage form in an amount ranging from about 250 micrograms up to about 800 milligrams or more at least once a day, for example, at least about 5, 20, 25, 50, 75, 100, 150, 200, 250, 300, 350, 400, 450, 500, 550, 600, 650, 700, 750, or 800 milligrams or more, once, twice, three, or up to four times a day according to the direction of the healthcare provider. Compound 2 often administered orally, but may be administered parenterally, topically, or in suppository form, as well as intranasally, as a nasal spray or as otherwise described herein. More generally, Compound 2 can be administered in a tablet, capsule, injection, intravenous formulation, suspension, liquid, emulsion, implant, particle, sphere, cream, ointment, suppository, inhalable form, transdermal form, buccal, sublingual, topical, gel, mucosal, and the like.

When a dosage form herein refers to a milligram weight dose, it refers to the amount of Compound 2 (i.e., the weight of the hemi-sulfate salt) unless otherwise specified to the contrary.

In certain embodiments, the pharmaceutical composition is in a dosage form that contains from about 1 mg to about 2000 mg, from about 10 mg to about 1000 mg, from about 100 mg to about 800 mg, from about 200 mg to about 600 mg, from about 300 mg to about 500 mg, or from about 400 mg to about 450 mg of Compound 2 in a unit dosage form. In certain embodiments, the pharmaceutical composition is in a dosage form, for example in a solid dosage form, that contains up to about 10, about 50, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, or about 1000 mg or more of Compound 2 in a unit dosage form. In one embodiment, Compound 2 is administered in a dosage form that delivers at least about 300 mg. In one embodiment, Compound 2 is administered in a dosage form that delivers at least about 400 mg. In one embodiment, Compound 2 is administered in a dosage form that delivers at least about 500 mg. In one embodiment, Compound 2 is administered in a dosage form that delivers at least about 600 mg. In one embodiment, Compound 2 is administered in a dosage form that delivers at least about 700 mg. In one embodiment, Compound 2 is administered in a dosage form that delivers at least about 800 mg. In certain embodiments, Compound 2 is administered at least once a day for up to 12 weeks. In certain embodiments, Compound 2 is administered at least once a day for up to 10 weeks. In certain embodiments, Compound 2 is administered at least once a day for up to 8 weeks. In certain embodiments, Compound 2 is administered at least once a day for up to 6 weeks. In certain embodiments, Compound 2 is administered at least once a day for up to 4 weeks. In certain embodiments, Compound 2 is administered at least once a day for at least 4 weeks. In certain embodiments, Compound 2 is administered at least once a day for at least 6 weeks. In certain embodiments, Compound 2 is administered at least once a day for at least 8 weeks. In certain embodiments, Compound 2 is administered at least once a day for at least 10 weeks. In certain embodiments, Compound 2 is administered at least once a day for at least 12 weeks. In certain embodiments, Compound 2 is administered at least every other day for up to 12 weeks, up to 10 weeks, up to 8 weeks, up to 6 weeks, or up to 4 weeks. In certain embodiments, Compound 2 is administered at least every other day for at least 4 weeks, at least 6 weeks, at least 8 weeks, at least 10 weeks, or at least 12 weeks. In one embodiment, at least about 600 mg of Compound 2 is administered at least once a day for up to 6 weeks. In one embodiment, at least about 500 mg of Compound 2 is administered at least once a day for up to 6 weeks. In one embodiment, at least about 400 mg of Compound 2 is administered at least once a day for up to 6 weeks. In one embodiment, at least 300 mg of Compound 2 is administered at least once a day for up to 6 weeks. In one embodiment, at least 200 mg of Compound 2 is administered at least once a day for up to 6 weeks. In one embodiment, at least 100 mg of Compound 2 is administered at least once a day for up to 6 weeks.

Metabolite 1-6 is the active triphosphate of Compound 2, but metabolite 1-6 is not measurable in plasma. A surrogate for metabolite 1-6 is metabolite 1-7. Metabolite 1-7 is a nucleoside metabolite measurable in plasma and is therefore an indication of the intracellular concentrations of metabolite 1-6. For maximum HCV antiviral activity, a dosage form of Compound 2 must achieve a metabolite 1-7 steady-state trough concentration ($C_{24,ss}$) that exceeds the $EC_{95}$ value of Compound 2. As shown in FIG. 24, the $EC_{95}$ of Compound 1 against clinical isolates of GT1, GT2, GT3, and GT4 is less than 25 ng/mL (Compound 1 $EC_{95}$ and Compound 2 $EC_{95}$ values are the same). In one embodiment, a dosage form of Compound 2 is delivered that achieves a steady-state trough concentration ($C_{24,ss}$) of metabolite 1-7 that is between approximately 15 to 75 ng/mL. In one embodiment, a dosage form of Compound 2 is delivered that achieves a steady-state trough concentration ($C_{24,ss}$) of metabolite 1-7 that is between approximately 20 to 60 ng/mL. In one embodiment, a dosage form of Compound 2 is delivered that achieves a steady-state trough concentration ($C_{24,ss}$) of metabolite 1-7 that is between approximately 30 to 60 ng/mL. In one embodiment, a dosage form of Compound 2 is delivered that achieves a steady-state trough concentration ($C_{24,ss}$) of metabolite 1-7 that is between approximately 20 to 50 ng/mL. In one embodiment, a dosage form of Compound 2 is delivered that achieves a steady-state trough concentration ($C_{24,ss}$) of metabolite 1-7 that is between approximately 30 to 50 ng/mL. In one embodiment, a dosage form of Compound 2 is delivered that achieves a steady-state trough concentration ($C_{24,ss}$) of metabolite 1-7 that is between approximately 20 to 45 ng/mL. In one embodiment, a dosage form of Compound 2 is delivered that achieves a steady-state trough concentration ($C_{24,ss}$) of metabolite 1-7 that is between approximately 20 to 30 ng/mL. In one embodiment, a dosage form of Compound 2 is delivered that achieves a steady-state trough concentration ($C_{24,ss}$) of metabolite 1-7 that is between approximately 20 to 35 ng/mL. In one embodiment, a dosage form of Compound 2 is delivered that achieves a steady-state trough concentration ($C_{24,ss}$) of metabolite 1-7 that is between approximately 20 to 25 ng/mL. Approximate dosage forms are ±10% of the steady-state trough concentration.

In one embodiment, Compound 2 is dosed at an amount that achieves a metabolite 1-7 AUC (area under the curve) of between approximately 1,200 and 3,000 ng/mL. In one embodiment, Compound 2 is dosed at an amount that achieves a metabolite 1-7 AUC of between approximately 1,500 and 3,000 ng/mL. In one embodiment, Compound 2 is dosed at an amount that achieves a metabolite 1-7 AUC of between approximately 1,800 and 3,000 ng/mL. In one embodiment, Compound 2 is dosed at an amount that achieves a metabolite 1-7 AUC of between approximately 2,100 and 3,000 ng/mL. In a preferred embodiment, Compound 2 is dosed at amount that achieves a metabolite 1-7 AUC of approximately 2,200 ng*h/mL. Approximate dosage forms are ±10% of the AUC.

In the case of the co-administration of Compound 2 in combination with another anti-HCV compound as otherwise described herein, the amount of Compound 2 according to the present invention to be administered in ranges from about 0.01 mg/kg of the patient to about 800 mg/kg or more of the patient or considerably more, depending upon the second agent to be co-administered and its potency against the virus, the condition of the patient and severity of the disease or infection to be treated and the route of administration. The other anti-HCV agent may for example be administered in amounts ranging from about 0.01 mg/kg to about 800 mg/kg. Examples of dosage amounts of the second active agent are amounts ranging from about 250 micrograms up to about 750 mg or more at least once a day, for example, at least about 5, 10, 20, 25, 50, 75, 100, 150, 200, 250, 300, 350, 400, 450, 500, 600, 700, or 800 milligrams or more, up to four times a day. In certain preferred embodiments, Compound 2 may be often administered in an amount ranging from about 0.5 mg/kg to about 50 mg/kg or more (usually up to about 100 mg/kg), generally depending upon the pharmacokinetic of the two agents in the patient. These dosage ranges generally produce effective blood level concentrations of active compound in the patient.

For purposes of the present invention, a prophylactically or preventive effective amount of the compositions according to the present invention falls within the same concentration range as set forth above for therapeutically effective amount and is usually the same as a therapeutically effective amount.

Administration of Compound 2 may range from continuous (intravenous drip) to several oral or intranasal administrations per day (for example, Q.I.D.) or transdermal administration and may include oral, topical, parenteral, intramuscular, intravenous, sub-cutaneous, transdermal (which may include a penetration enhancement agent), buccal, and suppository administration, among other routes of administration. Enteric coated oral tablets may also be used to enhance bioavailability of the compounds for an oral route of administration. The most effective dosage form will depend upon the bioavailability/pharmacokinetic of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of Compound 2 according to the present invention is often intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs, and solutions, suitable carriers and additives including water, glycols, oils, alcohols, flavoring agents, preservatives, coloring agents, and the like may be used. For solid oral preparations such as powders, tablets, capsules, and for solid preparations such as suppositories, suitable carriers and additives including starches, sugar carriers, such as dextrose, manifold, lactose, and related carriers, diluents, granulating agents, lubricants, binders, disintegrating agents, and the like may be used. If desired, the tablets or capsules may be enteric-coated or sustained release by standard techniques. The use of these dosage forms may significantly enhance the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents, and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In typical embodiments according to the present invention, Compound 2 and the compositions described are used to treat, prevent or delay a HCV infection or a secondary disease state, condition or complication of HCV.

VII. Combination and Alternation Therapy

It is well recognized that drug-resistant variants of viruses can emerge after prolonged treatment with an antiviral agent. Drug resistance sometimes occurs by mutation of a gene that encodes for an enzyme used in viral replication. The efficacy of a drug against an HCV infection, can be prolonged, augmented, or restored by administering the compound in combination or alternation with another, and perhaps even two or three other, antiviral compounds that induce a different mutation or act through a different pathway, from that of the principle drug. Alternatively, the pharmacokinetic, bio distribution, half-life, or other parameter of the drug can be altered by such combination therapy (which may include alternation therapy if considered concerted). Since the disclosed Compound 2 is an NSSB polymerase inhibitor, it may be useful to administer the compound to a host in combination with, for example a (1) Protease inhibitor, such as an NS3/4A protease inhibitor;

(2) NSSA inhibitor;
(3) Another NSSB polymerase inhibitor;
(4) NSSB non-substrate inhibitor;
(5) Interferon alfa-2a, which may be pegylated or otherwise modified, and/or ribavirin;
(6) Non-substrate-based inhibitor;
(7) Helicase inhibitor;
(8) Antisense oligodeoxynucleotide (S-ODN);
(9) Aptamer;
(10) Nuclease-resistant ribozyme;
(11) iRNA, including microRNA and SiRNA;
(12) Antibody, partial antibody or domain antibody to the virus, or
(13) Viral antigen or partial antigen that induces a host antibody response.

Non limiting examples of anti-HCV agents that can be administered in combination with Compound 2 of the invention, alone or with multiple drugs from this lists, are
(i) protease inhibitors such as telaprevir (Incivek®), boceprevir (Victrelis™), simeprevir (Olysio™), paritaprevir (ABT-450), glecaprevir (ABT-493), ritonavir (Norvir), ACH-2684, AZD-7295, BMS-791325, danoprevir, Filibuvir, GS-9256, GS-9451, MK-5172, Setrobuvir, Sovaprevir, Tegobuvir, VX-135, VX-222, and, ALS-220;
(ii) NSSA inhibitor such as ACH-2928, ACH-3102, IDX-719, daclatasvir, ledispasvir, velpatasvir (Epclusa), elbasvir (MK-8742), grazoprevir (MK-5172), and Ombitasvir (ABT-267);
(iii) NSSB inhibitors such as AZD-7295, Clemizole, dasabuvir (Exviera), ITX-5061, PPI-461, PPI-688, sofosbuvir (Sovaldi®), MK-3682, and mericitabine;
(iv) NSSB inhibitors such as ABT-333, and MBX-700;
(v) Antibody such as GS-6624;
(vi) Combination drugs such as Harvoni (ledipasvir/sofosbuvir); Viekira Pak (ombitasvir/paritaprevir/ritonavir/dasabuvir); Viekirax (ombitasvir/paritaprevir/ritonavir); G/P (paritaprevir and glecaprevir); Technivie (ombitasvir/paritaprevir/ritonavir) and Epclusa (sofosbuvir/velpatasvir) and Zepatier (elbasvir and grazoprevir).

If Compound 2 is administered to treat advanced hepatitis C virus leading to liver cancer or cirrhosis, in one embodiment, the compound can be administered in combination or alternation with another drug that is typically used to treat hepatocellular carcinoma (HCC), for example, as described by Andrew Zhu in "New Agents on the Horizon in Hepatocellular Carcinoma" Therapeutic Advances in Medical Oncology, V 5(1), January 2013, 41-50. Examples of suitable compounds for combination therapy where the host has or is at risk of HCC include anti-angiogenic agents, sunitinib, brivanib, linifanib, ramucirumab, bevacizumab, cediranib, pazopanib, TSU-68, lenvatinib, antibodies against EGFR, mTor inhibitors, MEK inhibitors, and histone decetylace inhibitors.

EXAMPLES

General Methods $^{1}$H, $^{19}$F and $^{31}$P NMR spectra were recorded on a 400 MHz Fourier transform Brucker spectrometer. Spectra were obtained DMSO-$d_{6}$ unless stated otherwise. The spin multiplicities are indicated by the symbols s (singlet), d (doublet), t (triplet), m (multiplet) and, br (broad). Coupling constants (J) are reported in Hz. The reactions were generally carried out under a dry nitrogen atmosphere using Sigma-Aldrich anhydrous solvents. All common chemicals were purchased from commercial sources.

The following abbreviations are used in the Examples:
AUC: Area under the Curve
$C_{24}$: Concentration of the drug in plasma at 24 hours
$C_{24,ss}$: Concentration at 24 hours after dosing at steady state
$C_{max}$: Maximum concentration of the drug achieved in plasma
DCM: Dichloromethane
EtOAc: Ethyl acetate
EtOH: Ethanol
HPLC: High pressure liquid chromatography
NaOH: Sodium hydroxide
$Na_{2}SO_{4}$: Sodium sulphate (anhydrous)
MeCN: Acetonitrile
MeNH$_{2}$: Methylamine
MeOH: Methanol
$Na_{2}SO_{4}$: Sodium sulfate
NaHCO$_{3}$: Sodium bicarbonate
NH$_{4}$Cl: Ammonium chloride
NH$_{4}$OH: Ammonium hydroxide
PE: Petroleum ether
Ph$_{3}$P: Triphenylphosphine
RH: relative humidity
Silica gel (230 to 400 mesh, Sorbent)
t-BuMgCl: t-Butyl magnesium chloride
$T_{max}$: Time at which $C_{max}$ is achieved
THF: Tetrahydrofuran (THF), anhydrous
TP: Triphosphate Example 1. Synthesis of Compound 1

Scheme 2

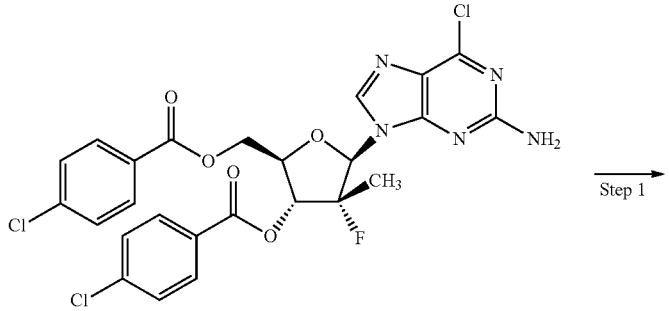

Step 1

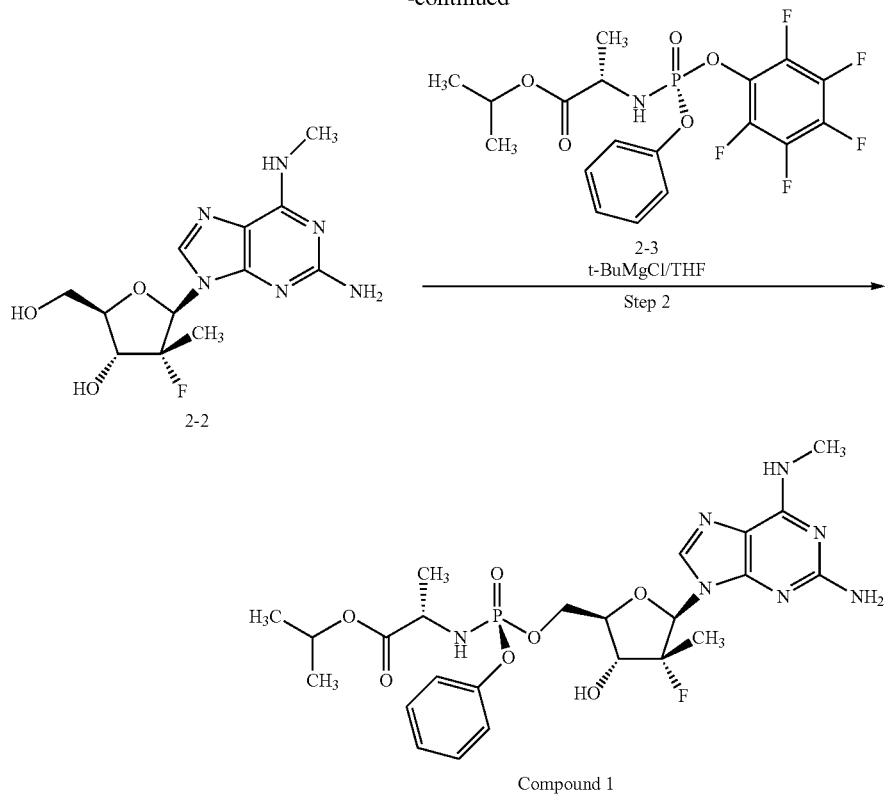

Step 1: Synthesis of (2R,3R,4R,5R)-5-(2-Amino-6-(methylamino)-9H-purin-9-yl)-4-fluoro-2-(hydroxymethyl)-4-methyltetrahydrofuran-3-ol (2-2)

A 50 L flask was charged with methanol (30 L) and stirred at 10±5° C. NH$_2$CH$_3$ (3.95 Kg) was slowly ventilated into the reactor at 10±5° C. Compound 2-1 (3.77 kg) was added in batches at 20±5° C. and stirred for 1 hour to obtain a clear solution. The reaction was stirred for an additional 6-8 hours, at which point HPLC indicated that the intermediate was less than 0.1% of the solution. The reactor was charged with solid NaOH (254 g), stirred for 30 minutes and concentrated at 50±5° C. (vacuum degree: −0.095). The resulting residue was charged with EtOH (40 L) and re-slurried for 1 hour at 60° C. The mixture was then filtered through celite and the filter cake was re-slurried with EtOH (15 L) for 1 hour at 60° C. The filtrate was filtered once more, combined with the filtrate from the previous filtration, and then concentrated at 50±5° C. (vacuum degree: −0.095). A large amount of solid was precipitated. EtOAc (6 L) was added to the solid residue and the mixture was concentrated at 50±5° C. (vacuum degree: −0.095). DCM was then added to the residue and the mixture was re-slurried at reflux for 1 hour, cooled to room temperature, filtered, and dried at 50±5° C. in a vacuum oven to afford compound 2-2 as an off-white solid (1.89 Kg, 95.3%, purity of 99.2%).

Analytic Method for Compound 2-2: The purity of compound 2-2 (15 mg) was obtained using an Agilent 1100 HPLC system with a Agilent Poroshell 120 EC-C18 4.6*150 mm 4-Micron column with the following conditions: 1 mL/min flow rate, read at 254 nm, 30° C. column temperature, 15 μL injection volume, and a 31 minute run time. The sample was dissolved in acetonitrile-water (20:80) (v/v). The gradient method is shown below.

| Time (min) | A % (0.05 TFA in water) | B % (Acetonitrile) |
|---|---|---|
| 0 | 95 | 5 |
| 8 | 80 | 20 |
| 13 | 50 | 50 |
| 23 | 5 | 95 |
| 26 | 5 | 95 |
| 26.1 | 95 | 5 |
| 31 | 95 | 5 |

Step 2: Synthesis of isopropyl(S)-(((2R,3R,4R,5R)-5-(2-Amino-6-(methylamino)-9H-purin-9-yl)-4-fluoro-3-hydroxy-4-methyltetrahydrofuran-2-yl)methoxy)(phenoxy)phosphoryl)-L-alaninate (Compound 1)

Compound 2-2 and compound 2-3 (isopropyl ((perfluorophenoxy)(phenoxy)phosphoryl)-L-alaninate) were dissolved in THF (1 L) and stirred under nitrogen. The suspension was then cooled to a temperature below −5° C. and a 1.7 M solution of t-BuMgCl solution (384 mL) was slowly added over 1.5 hours while a temperature of 5-10° C. was maintained. A solution of NH$_4$Cl (2 L) and water (8 L) was added to the suspension at room temperature followed by DCM. The mixture was stirred for 5 minutes before a 5% aqueous solution of K$_2$CO$_3$ (10 L) was added and the mixture was stirred for 5 additional minutes before filtering through diatomite (500 g). The diatomite was washed with DCM and the filtrate was separated. The organic phase was washed with a 5% aqueous K$_2$CO$_3$ solution (10 L×2), brine (10 L×3), and dried over Na$_2$SO$_4$ (500 g) for approximately 1 hour. Meanwhile, this entire process was repeated 7 times in parallel and the 8 batches were combined. The organic phases were filtered and concentrated at 45±5° C. (vacuum degree of 0.09 Mpa). EtOAc was added and the mixture was stirred for 1 hour at 60° C. and then at room temperature for 18 hours. The mixture was then filtered and washed with EtOAc (2 L) to afford crude Compound 1. The crude material was dissolved in DCM (12 L), heptane (18 L) was added at 10-20° C., and the mixture was allowed to stir for 30 minutes at this temperature. The mixture was filtered, washed with heptane (5 L), and dried at 50±5° C. to afford pure Compound 1 (1650 g, 60%).

Analytic Method for Compound 1: The purity of Compound 1 (25 mg) was obtained using an Agilent 1100 HPLC system with a Waters XTerra Phenyl 5 μm 4.6*250 mm column with the following conditions: 1 mL/min flow rate, read at 254 nm, 30° C. column temperature, 15 μL injection volume, and a 25 minute run time. The sample was dissolved in acetonitrile-water (50:50) (v/v). The gradient method is shown below.

| Time (min) | A % (0.1% $H_3PO_4$ in water) | B % (Acetonitrile) |
|---|---|---|
| 0 | 90 | 10 |
| 20 | 20 | 80 |
| 20.1 | 90 | 10 |
| 25 | 90 | 10 |

Example 2. Characterization of Amorphous and Crystalline Compound 1

Figure 1B:
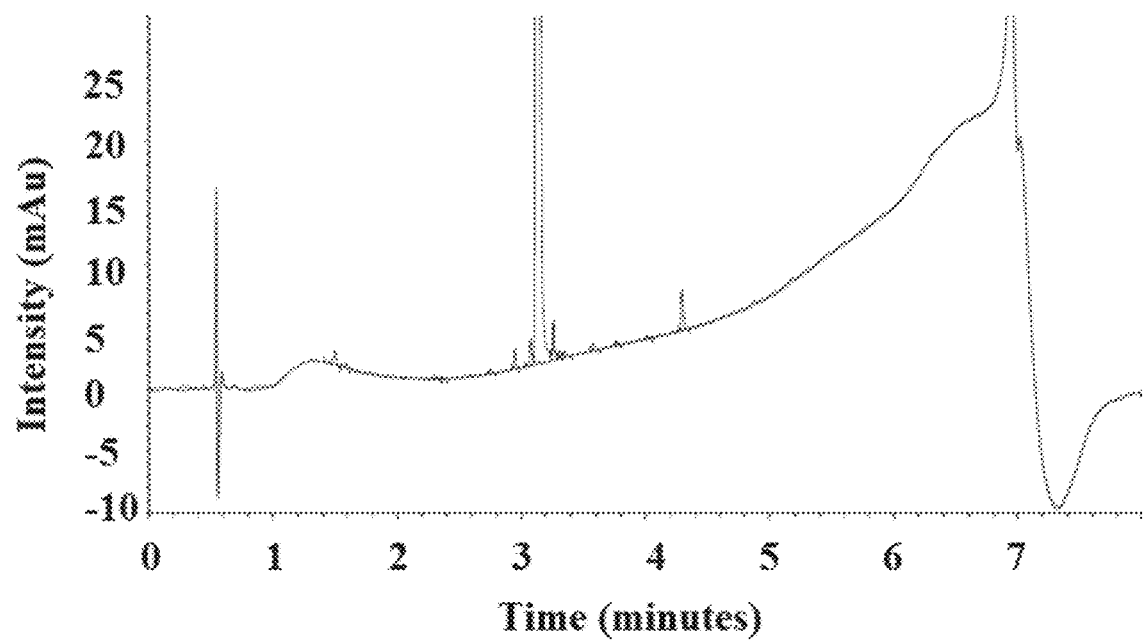
FIG. 1B is the HPLC chromatograph of amorphous Compound 1 (sample 1-1) to determine purity as described in Example 2. The purity of the sample was 98.7%. The x-axis is time measured in minutes and the y-axis is intensity measured in counts.
Figure 2A:
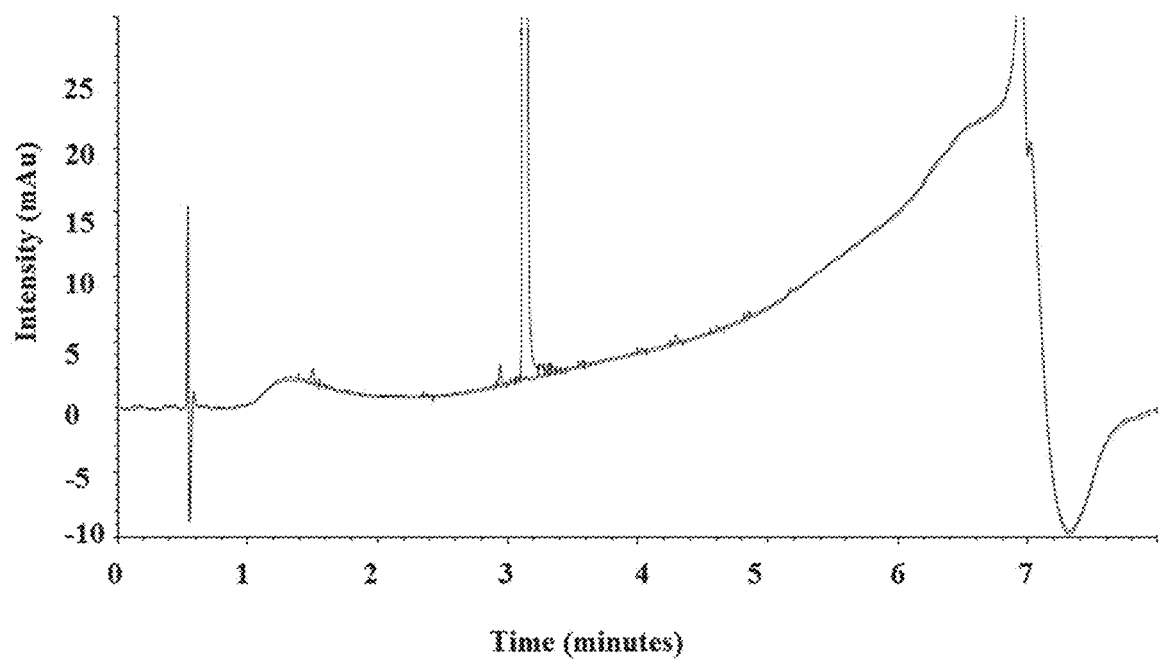
FIG. 2A is the HPLC chromatograph of crystalline Compound 1 (sample 1-2) to determine purity as described in Example 2. The purity of the sample was 99.11%. The x-axis is time measured in minutes and the y-axis is intensity measured in counts.
Figure 2B:
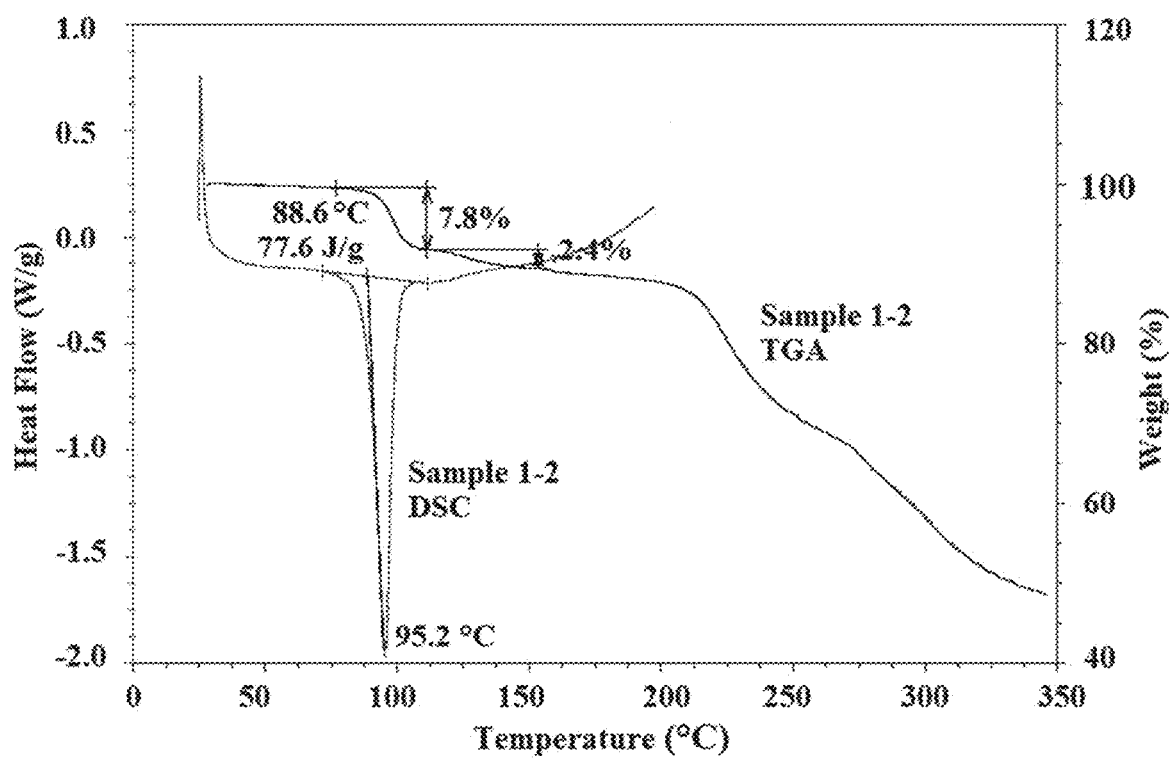
FIG. 2B is a DSC and TGA graph of crystalline Compound 1 (sample 1-2) prior to any stability studies for characterization purposes as described in Example 2. The x-axis is temperature measured in ° C., the left y-axis heat flow measured in (W/g), and the right y-axis is weight measured in percent.

Amorphous Compound 1 and crystalline Compound 1 were initially analyzed by XRPD, $^1$HNMR, and HPLC. The XRPD patterns for both compounds are shown in FIG. 1A and the HPLC traces to determine purity are shown in FIGS. 1B and 2A, respectively. Table 1 is a list of peaks from the XRPD of crystalline Compound 1 and Table 2 is a list of relative retention times (RTT) from the HPLC traces. Amorphous Compound 1 was 98.61% pure and crystalline Compound 1 was 99.11% pure. Both compounds were a white solid. FIG. 2B is the TGA and DSC graphs of crystalline Compound 1. For crystalline Compound 1, an endotherm was observed at 88.6° C. and there was a 7.8% mass loss from 80-110° C.

A sample of Compound 1 was recrystallized from EtOAc/hexane and drawn with ORTEP. The absolute structure of Compound 1 was confirmed by the recrystallization of a single crystal. FIG. 3 is the ORTEP drawing of Compound 1. Crystal data and measurement data are shown in Table 3. The absolute stereochemistry of Compound 1 based on the X-ray crystallography is shown below:

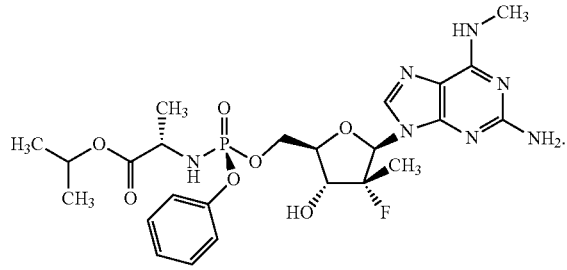

DSC data were collected on a TA Instruments Q2000 equipped with a 50 position auto-sampler. The calibration for thermal capacity was carried out using sapphire and the calibration for energy and temperature was carried out using certified indium. Typically approximately 3 mg of each sample, in a pin-holed aluminum pan, was heated at 10° C./min from 25° C. to 200° C. A purge of dry nitrogen at 50 ml/min was maintained over the sample. The instrument control software was Advantage for Q Series v2.8.0.394 and Thermal Advantage v5.5.3 and the data were analyzed using Universal Analysis v4.5A.

TGA data were collected on a TA Instruments Q500 TGA, equipped with a 16 position auto-sampler. The instrument was temperature calibrated using certified Alumel and Nickel. Typically 5-10 mg of each sample was loaded onto a pre-tared aluminum DSC pan and heated at 10° C./min from ambient temperature to 350° C. A nitrogen purge at 60 ml/min was maintained over the sample. The instrument control software was Advantage for Q Series v2.5.0.256 and Thermal Advantage v5.5.3 and the data were analyzed using Universal Analysis v4.5.

Amorphous Compound 1 (1-1)

$^1$H NMR (400 MHz, DMSO-d$_6$) δ ppm 1.01-1.15 (m, 9H), 1.21 (d, J=7.20 Hz, 3H), 2.75-3.08 (m, 3H), 3.71-3.87 (m, 1H), 4.02-4.13 (m, 1H), 4.22-4.53 (m, 3H), 4.81 (s, 1H), 5.69-5.86 (m, 1H), 6.04 (br d, J=19.33 Hz, 4H), 7.12-7.27 (m, 3H), 7.27-7.44 (m, 3H), 7.81 (s, 1H)

Crystalline Compound 1 (1-2)

$^1$H NMR (400 MHz, DMSO-d$_6$) δ ppm 0.97-1.16 (m, 16H), 1.21 (d, J=7.07 Hz, 3H), 2.87 (br s, 3H), 3.08 (s, 2H), 3.79 (br d, J=7.07 Hz, 1H), 4.08 (br d, J=7.58 Hz, 1H), 4.17-4.55 (m, 3H), 4.81 (quin, J=6.25 Hz, 1H), 5.78 (br s, 1H), 5.91-6.15 (m, 4H), 7.10-7.26 (m, 3H), 7.26-7.44 (m, 3H), 7.81 (s, 1H)

TABLE 1

Peak list for crystalline Compound 1

| Angle/°2θ | d spacing/Å | Intensity/Counts | Intensity/% |
|---|---|---|---|
| 6.03 | 14.64 | 1005 | 39.0 |
| 7.36 | 12.00 | 315 | 12.2 |
| 7.94 | 11.13 | 1724 | 66.9 |
| 9.34 | 9.47 | 2500 | 97.0 |
| 9.51 | 9.29 | 860 | 33.4 |
| 9.77 | 9.05 | 1591 | 61.8 |
| 11.08 | 7.98 | 2576 | 100.0 |
| 12.02 | 7.36 | 171 | 6.6 |
| 12.95 | 6.83 | 319 | 12.4 |
| 13.98 | 6.33 | 241 | 9.4 |
| 14.30 | 6.19 | 550 | 21.4 |
| 14.69 | 6.03 | 328 | 12.7 |
| 15.20 | 5.82 | 2176 | 84.5 |
| 15.94 | 5.56 | 1446 | 56.1 |
| 16.75 | 5.29 | 1009 | 39.2 |
| 17.29 | 5.13 | 700 | 27.2 |
| 17.72 | 5.00 | 1213 | 47.1 |
| 18.11 | 4.89 | 1565 | 60.8 |
| 18.46 | 4.80 | 302 | 11.7 |
| 18.89 | 4.69 | 385 | 14.9 |
| 19.63 | 4.52 | 636 | 24.7 |
| 20.37 | 4.36 | 1214 | 47.1 |
| 20.74 | 4.28 | 1198 | 46.5 |
| 21.24 | 4.18 | 640 | 24.8 |
| 22.31 | 3.98 | 961 | 37.3 |
| 22.88 | 3.88 | 806 | 31.3 |
| 23.43 | 3.79 | 355 | 13.8 |
| 24.08 | 3.69 | 573 | 22.2 |
| 24.49 | 3.63 | 159 | 6.2 |
| 25.00 | 3.56 | 351 | 13.6 |
| 25.36 | 3.51 | 293 | 11.4 |

TABLE 1-continued

Peak list for crystalline Compound 1

| Angle/°2θ | d spacing/Å | Intensity/Counts | Intensity/% |
|---|---|---|---|
| 26.09 | 3.41 | 235 | 9.1 |
| 26.26 | 3.39 | 301 | 11.7 |
| 26.83 | 3.32 | 696 | 27.0 |
| 27.35 | 3.26 | 436 | 16.9 |
| 27.46 | 3.25 | 363 | 14.1 |
| 28.07 | 3.18 | 200 | 7.8 |
| 28.30 | 3.15 | 195 | 7.6 |
| 28.82 | 3.10 | 599 | 23.3 |
| 29.85 | 2.99 | 217 | 8.4 |
| 30.26 | 2.95 | 186 | 7.2 |
| 30.75 | 2.91 | 333 | 12.9 |
| 31.12 | 2.87 | 149 | 5.8 |
| 31.85 | 2.81 | 238 | 9.2 |
| 33.28 | 2.69 | 261 | 10.1 |
| 34.77 | 2.58 | 171 | 6.6 |
| 35.18 | 2.55 | 175 | 6.8 |
| 36.83 | 2.44 | 327 | 12.7 |
| 37.41 | 2.40 | 172 | 6.7 |

TABLE 2

Relative Retention Times from HPLC chromatographs of Amorphous Compound 1 and Crystalline Compound 1

| Amorphous Compound 1 | | Crystalline Compound 1 | |
|---|---|---|---|
| RRT | Area % | RRT | Area % |
| 0.48 | 0.15 | 0.48 | 0.17 |
| 0.51 | 0.04 | 0.48 | 0.17 |
| 0.48 | 0.15 | 0.94 | 0.12 |
| 0.51 | 0.04 | 1.00 | 99.11 |
| 0.94 | 0.13 | 1.04 | 0.22 |
| 0.98 | 0.21 | 1.37 | 0.07 |
| 1.00 | 98.61 | | |
| 1.04 | 0.29 | | |
| 1.37 | 0.31 | | |

TABLE 3

Crystal and Data Measurement of Compound 1

| Bond Precision | C-C = 0.0297A, Wavelength = 1.54184 |
|---|---|
| Cell | a = 10.1884(3) b = 28.6482(9) c = 12.9497(5) alpha = 90 beta = 113.184(4) gamma = 90 |
| Temperature | 150K |

| | Calculated | Reported |
|---|---|---|
| Volume | 3474.5(2) | 3474.5(2) |
| Space Group | P21 | P 1 21 1 |
| Hall Group | P 2yb | P 2yb |
| Moiety Formula | C24 H34 F N7 O7 P | 2(C24 H34 F N7 O7 P) |
| Sum Formula | C24 H34 F N7 O7 P | C48 H68 F2 N14 O14 P2 |
| Mr | 582.55 | 1165.10 |
| Dx, g cm⁻¹ | 1.114 | 1.114 |
| Z | 4 | 2 |
| Mu (mm⁻¹) | 1.139 | 1.139 |
| F000 | 1228.0 | 1228.0 |
| F000' | 1233.21 | |
| h, k, l$_{max}$ | 12,34,15 | 12,34,15 |
| N$_{ref}$ | 12742 [6510] | 8259 |
| T$_{min}$, T$_{max}$ | 0.790, 0.815 | 0.808, 1.000 |
| T$_{min}$' | 0.716 | |
| Correction Method | # Reported T Limits: T$_{min}$ = 0.808 T$_{max}$ = 1.00 | |
| AbsCorr | MULTI-SCAN | |
| Data completeness | 1.27/0.65 | |
| Theta (max) | 68.244 | |

TABLE 3-continued

Crystal and Data Measurement of Compound 1

| R (reflections) | 0.2091 (7995) |
|---|---|
| wR2 (reflections) | 0.5338 (8259) |
| S | 2.875 |
| Npar | 716 |

Figure 4A:
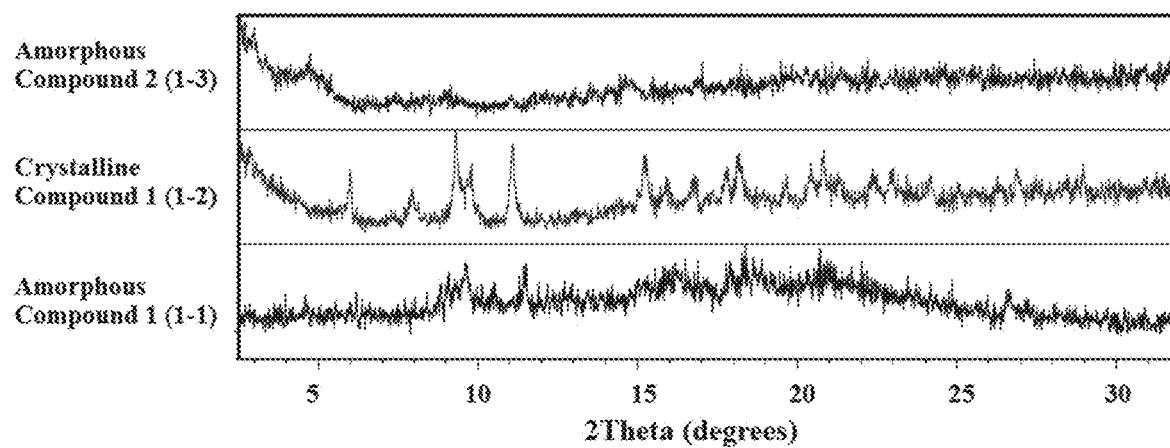
FIG. 4A is an overlay of XRPD diffractograms of samples 1-1 (amorphous Compound 1), 1-2 (crystalline Compound 1), and 1-3 (amorphous Compound 2) after storing at 25° C. and 60% relative humidity for 14 days as described in Example 2. The x-axis is 2Theta measured in degrees and the y-axis is intensity measured in counts.

This initial characterization was followed by storage at 25° C./60% relative humidity (RH) for 14 days with analysis by HPLC and XRPD after 7 and 14 days. FIG. 4A is the XRPD after 14 days at 25° C./60% (RH). Amorphous Compound 1 (sample 1-1) remained poorly crystalline, whereas crystalline Compound 1 (sample 1-2) retained its crystallinity, but both compounds were stable after 14 days at 25° C./60% (RH).

Example 3. Formation of Oxalate Salt Compound 4

Initially, the oxalate salt of Compound 1, Compound 4, was formed by mixing the oxalic salt with solvent (5 vol, 100 μL) and allowing any solution to evaporate at room temperature. Any suspension was matured (room temperature –50° C.) for 3 hours and crystallinity was accessed.

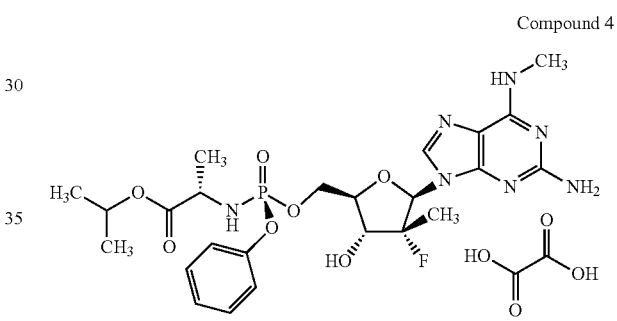

Compound 4

Table 4 shows the different solvents used in the production of Compound 4. All solvents except for two (cyclohexane and n-heptane) afforded crystalline products. Despite the high crystallinity and solubility of Compound 4, oxalate salts are not acceptable for clinical development due to the potential formation of kidney stones and other salts of compound 1 were explored.

TABLE 4

Formation of Oxalate Compound 4

| Solvent | Observation post acid addition at room temperature | Observation after maturation/evaporation |
|---|---|---|
| EtOH | Solution | OXA-Form 1 |
| IPA | Solution | OXA-Form 1 |
| Acetone | Solution | OXA-Form 1 |
| MEK | Solution | OXA-Form 1 |
| EtOAc | Suspension | OXA-Form 1 |
| iPrOAc | Suspension | OXA-Form 1 |
| THF | Solution | OXA-Form 1 |
| Toluene | Solution | OXA-Form 1 |
| MeCN | Solution | OXA-Form 1 |
| IPA:10% water | Solution | OXA-Form 1 |
| TBME | Suspension | OXA-Form 1 |
| Cyclohexane | Suspension | Amorphous |
| n-Heptane | Suspension | Amorphous |

Example 4. Salt Compounds of Amorphous Compound 1

Since the oxalate salt compound 4 (Example 3) could not be carried forward in clinical trials due to its potential to form kidney stones, amorphous salts of Compound 1 were formed with the counter ions listed in Table 5. Compound 1 was dissolved in t-butanol (20 vol, 6 ml) and the solution was treated with the acid counter-ions (1 equivalent for each sample except sample 1-9 which had 0.5 equivalent of sulfate). The samples were then frozen with the solvent removed by lyophilization. The residual solid in samples 1-4, 1-5, 1-6, 1-7, 1-8, and 1-9 was initially analyzed by XRPD and HPLC.

TABLE 5

Amorphous salt formation details

| Sample ID | Sample details | Stock solution details | Observation | NMR |
|---|---|---|---|---|
| 1-4 | HCl (1:1) | THF 1M | White solid | 3 fewer protons ~0.3 eq t-BuOH |
| 1-5 | Sulfuric (1:1) | THF 1M | White solid | 3 fewer protons ~0.3 eq t-BuOH |
| 1-6 | Fumaric (1:1) | MeOH: THF (1:1) 0.5M | Glassy solid | 1.05 eq fumaric acid 0.84 eq t-BuOH |
| 1-7 | Benzoic (1:1) | THF 1M | White solid | 1.0 eq benzoic acid 0.34 eq t-BuOH |
| 1-8 | Succinic (1:1) | MeOH 1M | Sticky white solid | ~1.1 eq succinic acid 0.37 eq t-BuOH |
| 1-9 | Sulfuric (0.5:1 acid: API) | THF 1M | White solid | 3 fewer protons ~0.3 eq t-BuOH |

$^1$HNMR spectrum were taken for all samples.

Sample 1-4, HCl (1:1) Salt $^1$H NMR (400 MHz, DMSO-d$_6$) δ ppm 0.93-1.39 (m, 16H), 2.97 (br s, 2H), 3.70-3.88 (m, 1H), 4.10 (br s, 1H), 4.18-4.49 (m, 3H), 4.70-4.88 (m, 1H), 5.71-5.94 (m, 1H), 6.07 (br d, J=19.07 Hz, 2H), 7.14-7.27 (m, 3H), 7.29-7.44 (m, 2H), 7.83-8.19 (m, 1H)

Sample 1-5, Sulfuric (1:1) Salt $^1$H NMR (400 MHz, DMSO-d$_6$) δ ppm 0.97-1.38 (m, 15H), 2.96 (br s, 2H), 4.06-4.18 (m, 1H), 4.19-4.49 (m, 3H), 4.66-4.91 (m, 1H), 5.70-5.95 (m, 1H), 5.96-6.16 (m, 2H), 7.10-7.27 (m, 3H), 7.30-7.43 (m, 2H), 7.88-8.19 (m, 1H)

Sample 1-6, Fumaric (1:1) Salt $^1$H NMR (400 MHz, DMSO-d$_6$) δ ppm 0.95-1.31 (m, 21H), 2.87 (br s, 3H), 3.79 (br d, J=7.20 Hz, 1H), 4.01-4.13 (m, 1H), 4.16-4.23 (m, 1H), 4.16-4.24 (m, 1H), 4.20 (s, 1H), 4.18-4.23 (m, 1H), 4.24-4.52 (m, 1H), 4.24-4.52 (m, 1H), 4.24-4.49 (m, 1H), 4.72-4.88 (m, 1H), 5.68-5.86 (m, 1H), 6.04 (br d, J=19.33 Hz, 4H), 6.63 (s, 1H), 6.61-6.66 (m, 1H), 7.12-7.27 (m, 3H), 7.27-7.45 (m, 3H), 7.81 (s, 1H), 13.16 (br s, 2H)

Sample 1-7, Benzoic (1:1) Salt $^1$NMR (400 MHz, DMSO-d$_6$) δ ppm 0.96-1.30 (m, 15H), 2.87 (br s, 3H), 3.79 (br d, J=7.07 Hz, 1H), 4.07 (br s, 1H), 4.20 (s, 1H), 4.25-4.52 (m, 3H), 4.81 (s, 1H), 5.71-5.85 (m, 1H), 6.04 (br d, J=19.33 Hz, 4H), 7.08-7.27 (m, 3H), 7.27-7.43 (m, 3H), 7.45-7.57 (m, 2H), 7.63 (s, 1H), 7.81 (s, 1H), 7.95 (dd, J=8.27, 1.33 Hz, 2H), 12.98 (br s, 1H)

Sample 1-8, Succinic (1:1) Salt $^1$H NMR (400 MHz, DMSO-d$_6$) δ ppm 0.98-1.28 (m, 15H), 2.42 (s, 5H), 2.87 (br s, 3H), 3.57-3.62 (m, 1H), 3.70-3.86 (m, 1H), 4.02-4.14 (m, 1H), 4.20 (s, 1H), 4.24-4.51 (m, 3H), 4.70-4.88 (m, 1H), 5.69-5.86 (m, 1H), 6.04 (br d, J=19.33 Hz, 4H), 7.12-7.27 (m, 3H), 7.27-7.44 (m, 3H), 7.81 (s, 1H), 11.95-12.58 (m, 2H)

Sample 1-9, Sulfuric (0.5:1) Salt $^1$NMR (400 MHz, DMSO-d$_6$) δ ppm 1.02-1.31 (m, 15H), 2.94 (br s, 3H), 3.79 (br d, J=7.20 Hz, 2H), 4.09 (br s, 1H), 4.22-4.48 (m, 3H), 4.72-4.90 (m, 1H), 5.71-5.92 (m, 1H), 6.07 (br d, J=19.07 Hz, 2H), 7.12-7.28 (m, 3H), 7.31-7.44 (m, 2H), 7.75-8.19 (m, 1H).

Figure 4B:
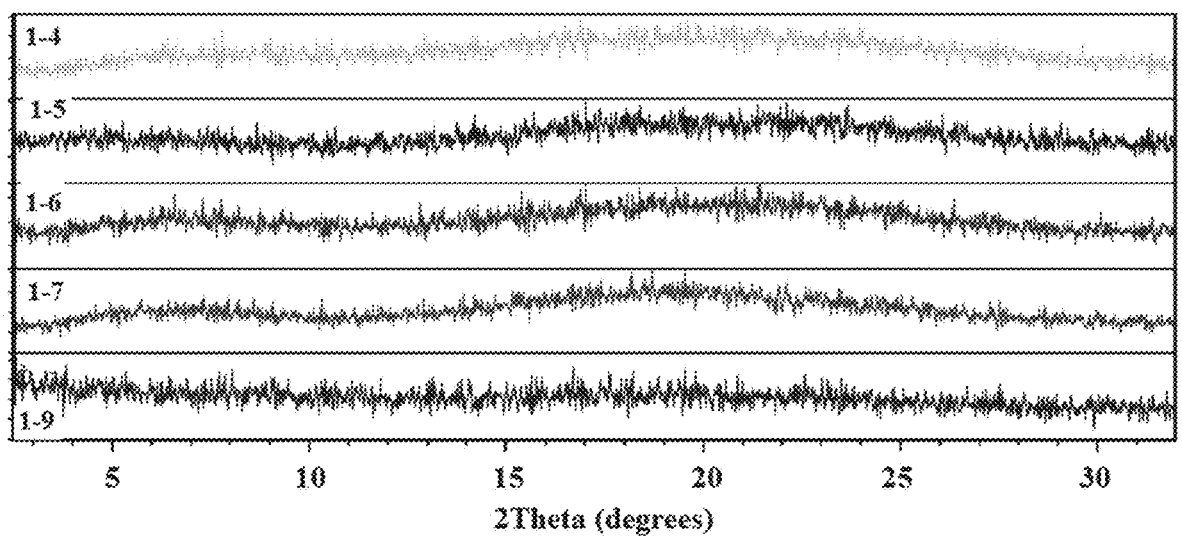
FIG. 4B is an overlay of XRPD diffractograms of samples 1-4, 1-5, 1-6, 1-7, and 1-9 after storing at 25° C. and 60% relative humidity for 7 days as described in Example 4. The x-axis is 2Theta measured in degrees and the y-axis is intensity measured in counts.
Figure 5A:
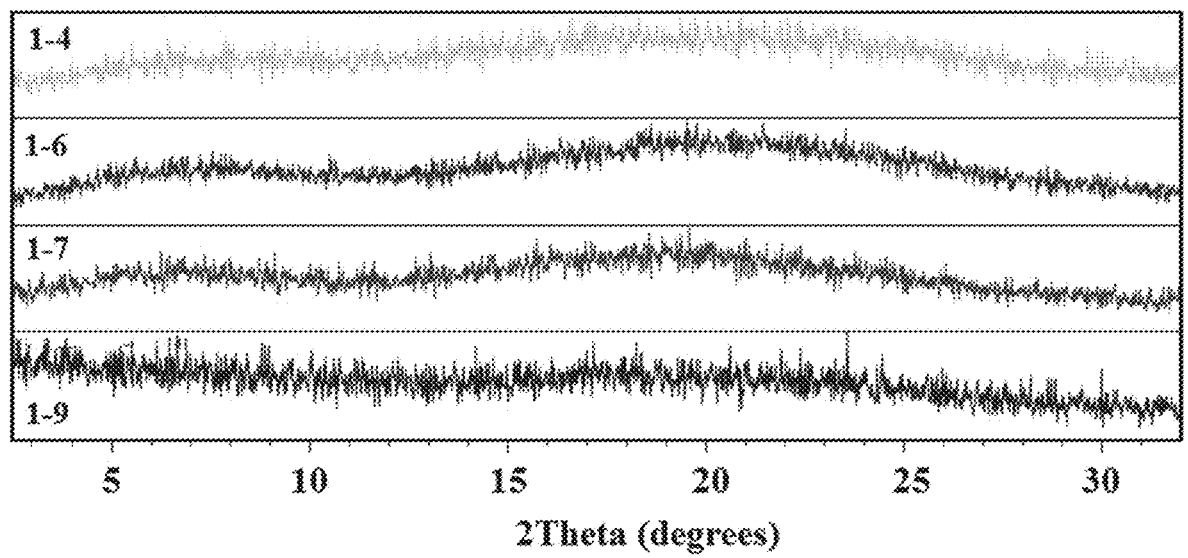
FIG. 5A is an overlay of XRPD diffractograms of samples 1-4, 1-6, 1-7, and 1-9 after storing at 25° C. and 60% relative humidity for 14 days as described in Example 4. The x-axis is 2Theta measured in degrees and the y-axis is intensity measured in counts.

The samples were then subjected to storage at 25° C./60% relative humidity (RH) for 14 days with analysis by HPLC and XRPD after 7 (FIG. 4B) and 14 days (FIG. 5A). All prepared salts remained amorphous and the observations are shown in Table 6. The mono sulfate (sample 1-5) and succinate salts (sample 1-8) were found to be physically unstable and deliquesced or became a gum during the course of the study. Both the fumarate (sample 1-6) and benzoate salts (sample 1-7) were found to be glassy solids. The HCl salt (sample 1-4) was found to retain its physical appearance. Surprisingly, the hemi-sulfate salt (sample 1-9) also retained its physical appearance as a white solid in contrast to mono-sulfate compound (sample 1-5), which was a sticky gum. Results are shown in Table 6. The mono HCl salt (sample 1-4) and the hemi-sulfate salt (sample 1-9) were found to be physically and chemically stable after 2 weeks storage at 25° C./60% relative humidity (RH). Although both salts were stable over the two weeks, the hemi-sulfate salt was superior to the HCl salt because the HCl salt was hygroscopic, rendering it less useful compared to the hemi-sulfate salt for long-term storage or use.

TABLE 6

Stability of samples after 7 and 14 days at 25° C./60% RH

| Sample ID | Time exposed to 25° C./60% RH (days) | | | | | |
|---|---|---|---|---|---|---|
| | 0 | | 7 | | 14 | |
| | HPLC | Observation | HPLC | Observation | HPLC | Observation |
| 1-1 | 98.6 | White solid | 98.7 | White solid | 98.5 | White solid |
| 1-2 | 99.1 | White solid | 99.2 | White solid | 99.0 | White solid |
| 1-3 | 99.7 | White solid | 99.6 | White solid | 99.4 | White solid |
| 1-4 | 98.7 | White solid | 98.8 | White solid | 98.6 | White solid |
| 1-5 | 98.4 | White solid | 55.7 | Sticky white solid | — | Sticky gum |
| 1-6 | 98.7 | Glassy solid | 98.6 | Clear glassy solid | 98.4 | White glassy solid |
| 1-7 | 98.8 | White solid | 98.8 | Clear glassy solid | 98.7 | Clear glassy solid |
| 1-8 | 98.7 | Sticky white solid | — | Deliquesced/ sticky oil | — | Deliquesced |
| 1-9 | 98.7 | White solid | 98.1 | White solid | 96.4 | White solid |

Example 5. Characterization of Amorphous Compound 2

Figure 5B:
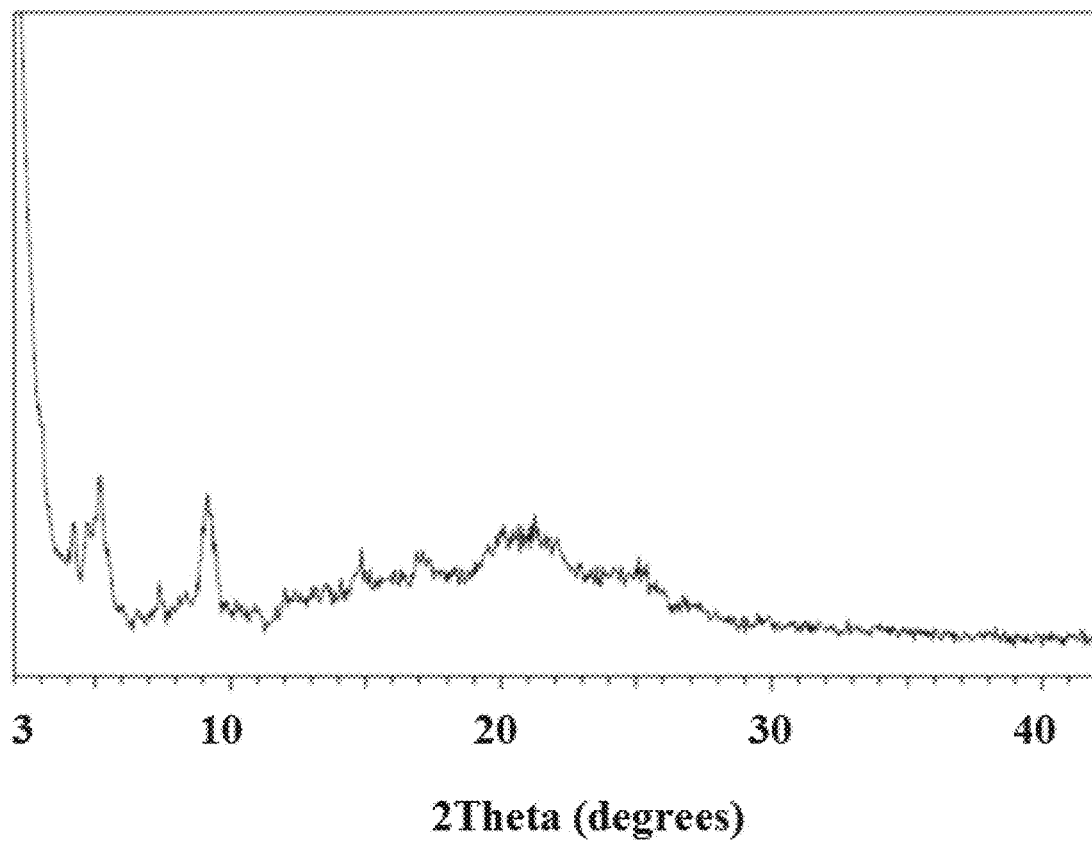
FIG. 5B is the XRPD pattern of amorphous Compound 2 (sample 1-3) as described in Example 5. The x-axis is 2Theta measured in degrees and the y-axis is intensity measured in counts.
Figure 6A:
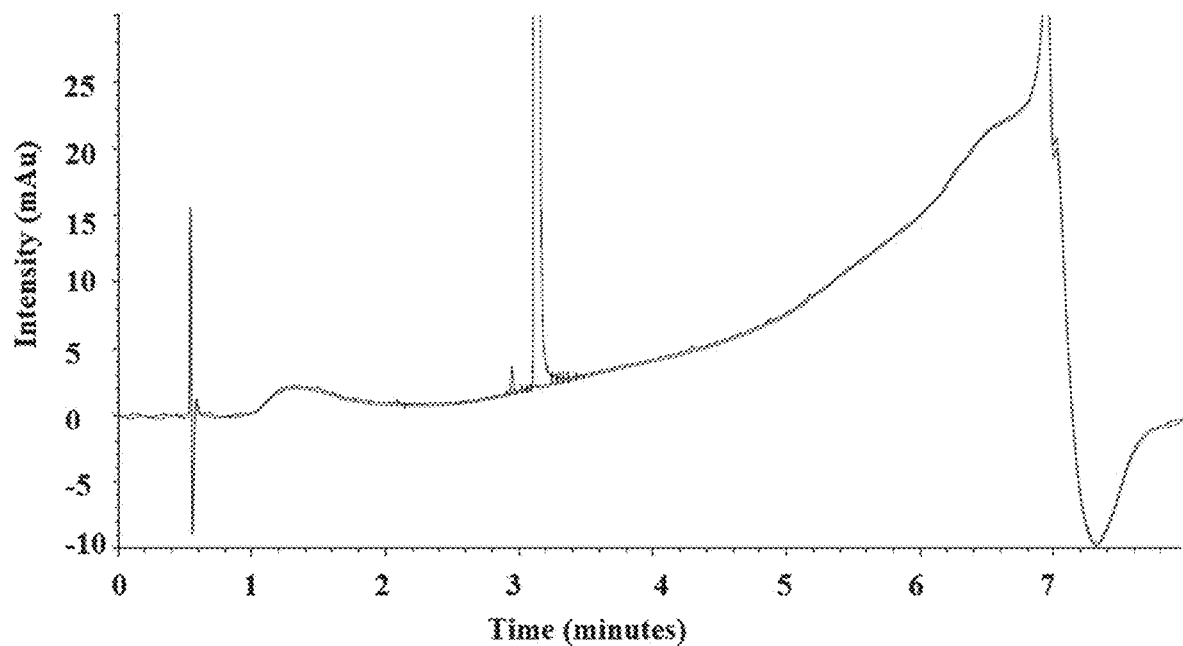
FIG. 6A is the HPLC chromatograph of amorphous Compound 2 (sample 1-3) to determine purity as described in Example 5. The purity of the sample was 99.6%. The x-axis is time measured in minutes and the y-axis is intensity measured in counts.
Figure 6B:
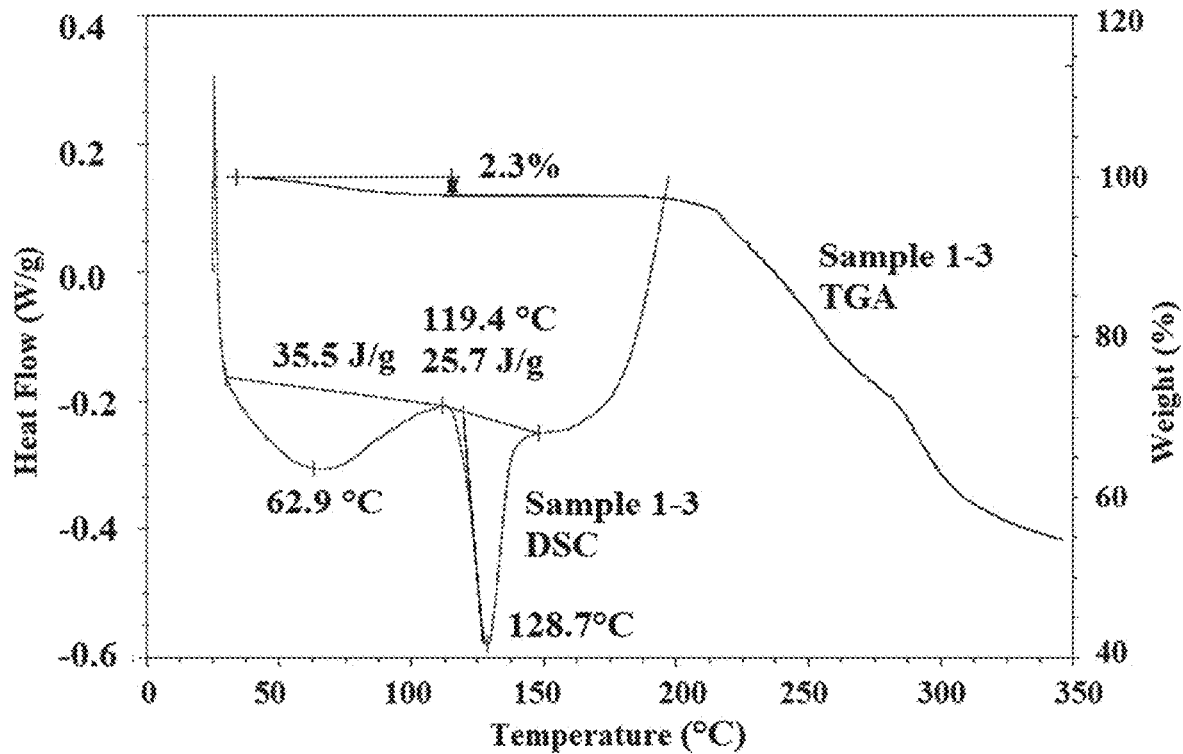
FIG. 6B is a DSC and TGA graph for amorphous Compound 2 (sample 1-3) prior to any stability studies for characterization purposes as described in Example 5. The x-axis is temperature measured in ° C., the left y-axis heat flow measured in (W/g), and the right y-axis is weight measured in percent.

Amorphous Compound 2 was initially analyzed by XRPD, $^1$HNMR, DSC, TGA, and HPLC. The XRPD pattern for amorphous Compound 2 overlaid with amorphous Compound 1 and crystalline Compound 1 is shown in FIG. 1A and the XRPD pattern of amorphous Compound 2 alone is shown in FIG. 5B. Table 7 is a peak list from the XRPD pattern shown in FIG. 5B. The HPLC trace to determine purity is shown in FIG. 6A. Table 8 is a list of relative retention times (RTT) from the HPLC trace shown in FIG. 6A. Amorphous Compound 2 was 99.68% pure. FIG. 6B is a TGA and DSC graph of amorphous Compound 2. Experimental details for the TGA and DSC experiments are given in Example 2.

TABLE 7

Peak list for Amorphous Compound 2

| Angle/°2θ | d spacing/Å | Intensity/Counts | Intensity/% |
|---|---|---|---|
| 4.20 | 21.03 | 486 | 81.8 |
| 4.67 | 18.91 | 482 | 81.0 |
| 5.16 | 17.10 | 595 | 100.0 |
| 9.13 | 9.68 | 547 | 92.0 |

TABLE 8

HPLC chromatogram of Amorphous Compound 2
Amorphous Compound 2

| RRT | Area % |
|---|---|
| 0.48 | 0.02 |
| 0.48 | 0.02 |
| 0.67 | 0.01 |
| 0.94 | 0.13 |
| 1.00 | 99.68 |
| 1.04 | 0.06 |

Amorphous Compound 2

$^1$H NMR (400 MHz, DMSO-d$_6$) δ ppm 0.93-1.29 (m, 13H), 2.94 (br s, 3H), 3.79 (td, J=10.04, 7.07 Hz, 2H), 4.05-4.19 (m, 1H), 4.19-4.50 (m, 3H), 4.81 (quin, J=6.25 Hz, 1H), 5.71-5.94 (m, 1H), 5.97-6.16 (m, 2H), 7.14-7.28 (m, 3H), 7.31-7.44 (m, 2H), 7.82-8.09 (m, 1H)

Example 6. Crystallization of Amorphous Compound 2

Figure 7A:
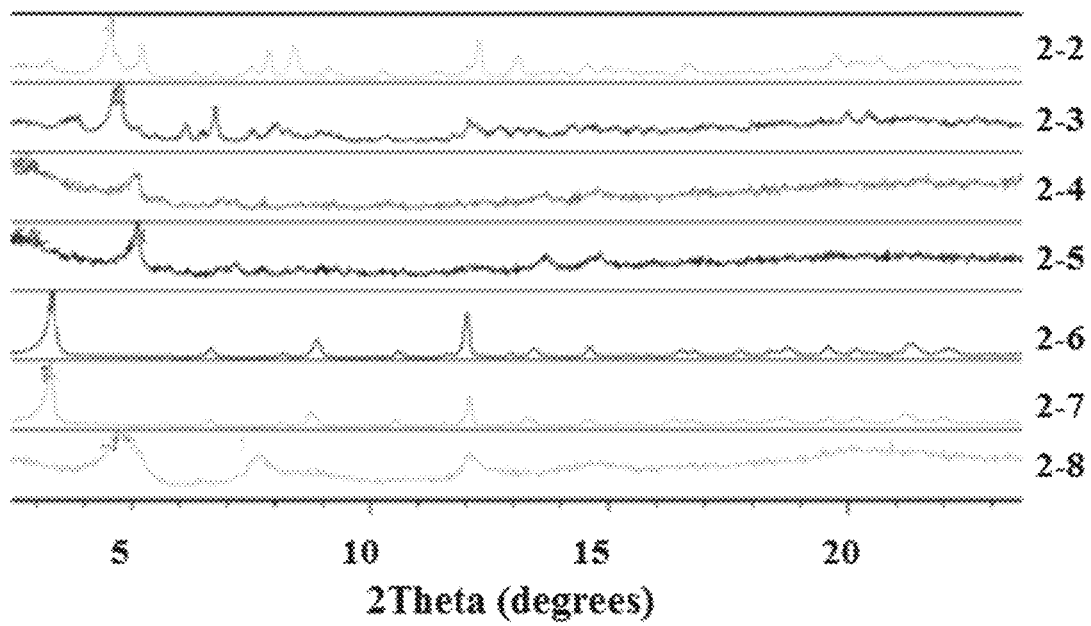
FIG. 7A is an overlay of XRPD diffractograms of crystalline samples (samples 2-2, 2-6, and 2-7) and poorly crystalline samples (samples 2-3, 2-4, 2-5, and 2-8) identified from the crystallizations of Compound 2 (Example 6). The x-axis is 2Theta measured in degrees and the y-axis intensity measured in counts.

Since the hemi-sulfate salt was found to remain as a solid after the 14 day stability study as shown in Table 6, preliminary tests studying crystallization conditions using 11 different solvents was conducted. Amorphous Compound 2 was suspended in 5 volumes of solvent at 25° C. (sample 2-1, 2-2, 2-3, 2-4, 2-5, 2-6, 2-7, 2-8, 2-9, 2-10, and 2-11). To those samples that were not free flowing (2-1, 2-2, 2-3, 2-4, 2-5, 2-6, 2-7, 2-8, and 2-10), an additional 5 volumes of solvent was added. The samples were then matured at 25-50° C. (1° C./min between temperatures and 4 hour at each temperature) for 6 days except for sample 2-1, which was observed to be a clear solution after 1 day and was allowed to evaporate under ambient conditions. The results are shown in Table 9. Crystalline patterns resulted from crystallization with isobutanol (sample 2-1), acetone (sample 2-2), EtOAc (sample 2-6), and iPrOAc (sample 2-7). Two poorly crystalline samples were also identified from crystallization with MEK (sample 2-4) and MIBK (sample 2-5). The XRPD patterns are shown in FIG. 7A.

TABLE 9

Crystallization Conditions of Compound 2

| Sample ID | Solvent | Observation after 5 volumes | Observation after 10 volumes | Observation after 1 day maturation | XRPD |
|---|---|---|---|---|---|
| 2-1 | IPA | Solid-not free flowing | Free flowing suspension | Solution, evaporated at RT yielding a gum | Gum |
| 2-2 | Isobutanol | Solid-not free flowing | Free flowing suspension | Suspension | Crystalline-Pattern 2 |
| 2-3 | Acetone | Solid-not free flowing | Free flowing suspension | Suspension | Crystalline-Pattern 3 |
| 2-4 | MEK | Solid-not free flowing | Free flowing suspension | Suspension | Poorly crystalline-Pattern 4 |
| 2-5 | MIBK | Solid-not free flowing | Free flowing suspension | Suspension | Poorly crystalline-Pattern 4 |
| 2-6 | EtOAc | Solid-not free flowing | Free flowing suspension | Suspension | Crystalline-Pattern 1 |
| 2-7 | iPrOAc | Solid-not free flowing | Free flowing suspension | Suspension | Crystalline-Pattern 1 |
| 2-8 | THF | Solid-not free flowing | Free flowing suspension | Suspension | Poorly crystalline |
| 2-9 | TBME | Free flowing suspension | — | Suspension | Amorphous |
| 2-10 | Toluene | Solid-not free flowing | Free flowing suspension | Suspension | Amorphous |
| 2-11 | Heptane | Free flowing suspension | — | Suspension | Amorphous |

Figure 7B:
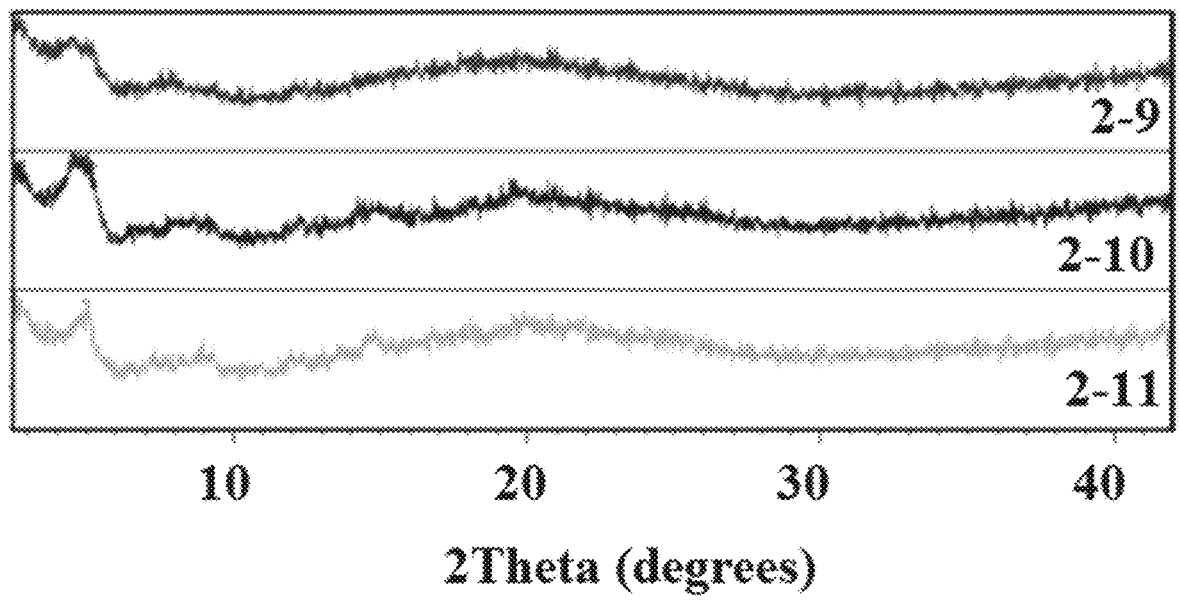
FIG. 7B is an overlay of XRPD diffractograms of amorphous samples (samples 2-9, 2-10, and 2-11) identified from the crystallizations of Compound 2 (Example 6). The x-axis is 2Theta measured in degrees and the y-axis intensity measured in counts.
Figure 8A:
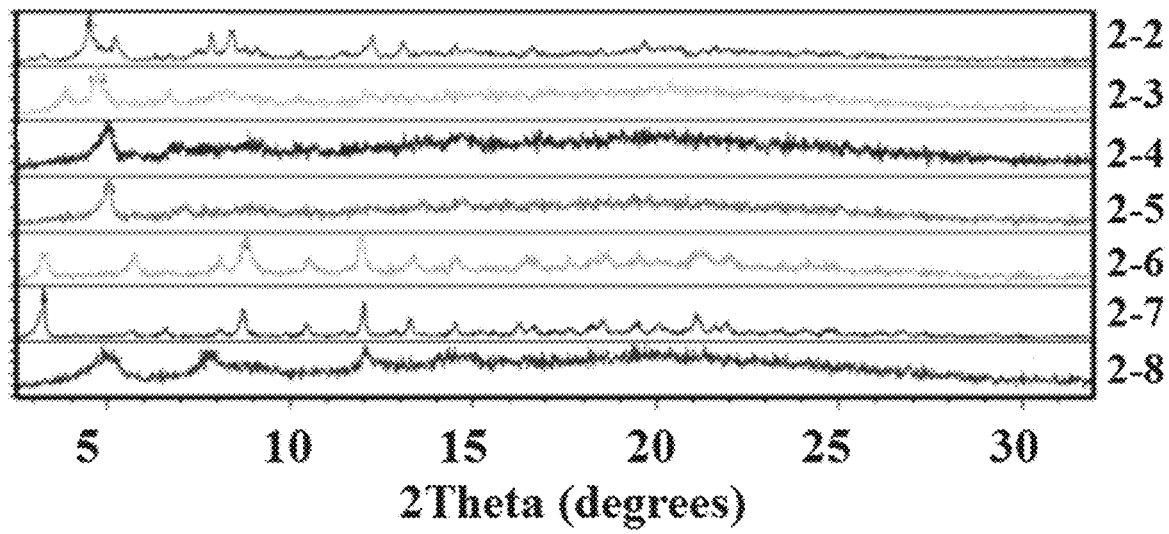
FIG. 8A is an overlay of XRPD diffractograms of samples (samples 2-2, 2-3, 2-4, 2-5, 2-6, 2-7 and 2-8) after 6 days storage at 25° C. and 60% relative humidity (Example 6). The x-axis is 2Theta measured in degrees and the y-axis intensity measured in counts.
Figure 8B:
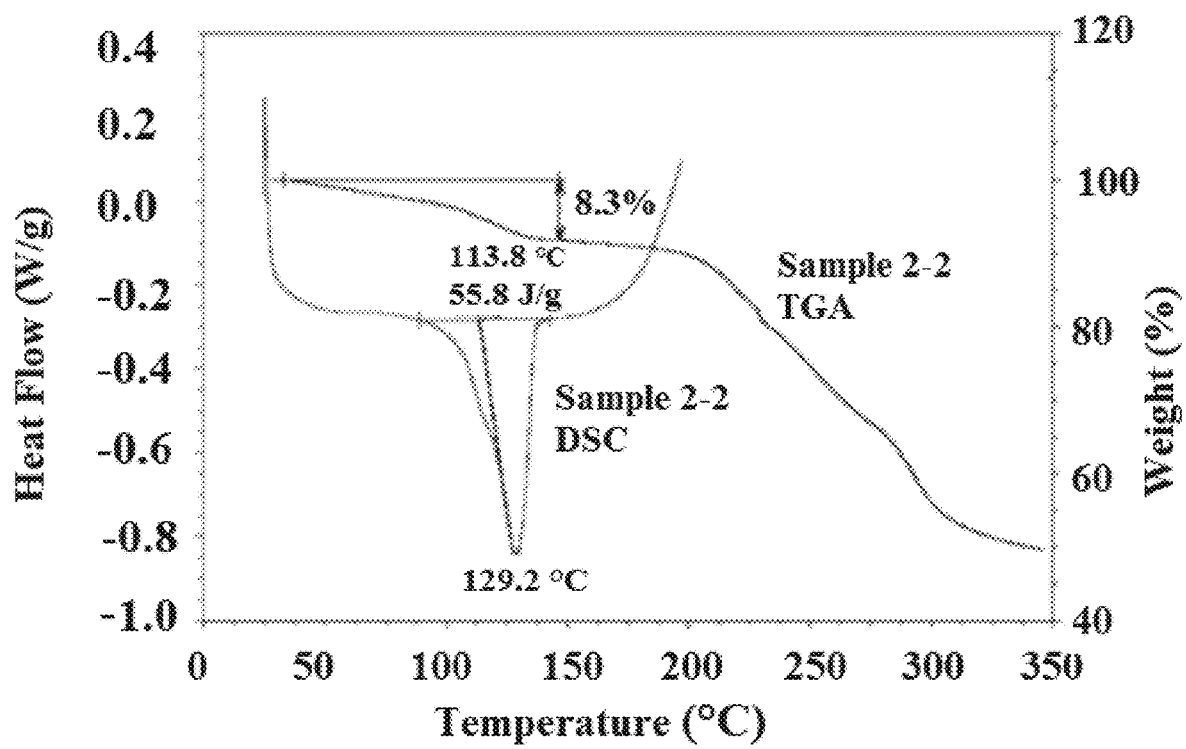
FIG. 8B is a DSC and TGA graph for sample 2-2 (Example 6). The x-axis is temperature measured in ° C., the left y-axis heat flow measured in (W/g), and the right y-axis is weight measured in percent. Experimental procedures for DSC and TGA collection are given in Example 2.
Figure 9A:
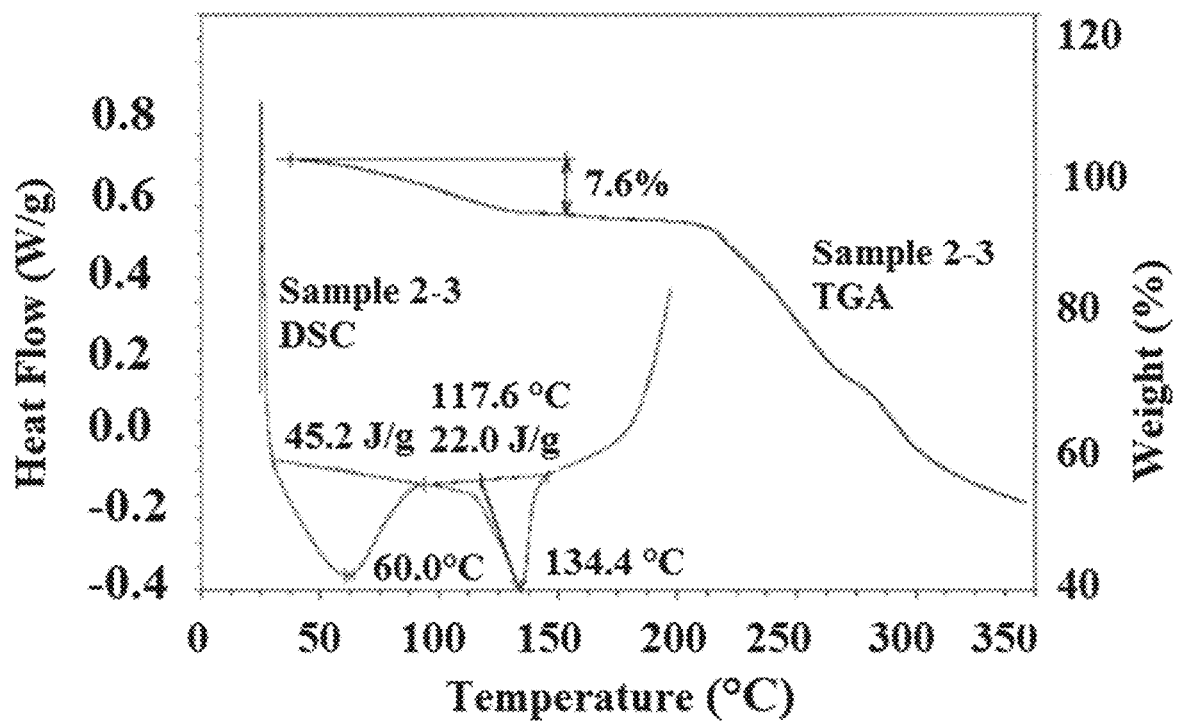
FIG. 9A is a DSC and TGA graph for sample 2-3 (Example 6). The x-axis is temperature measured in ° C., the left y-axis heat flow measured in (W/g), and the right y-axis is weight measured in percent. Experimental procedures for DSC and TGA collection are given in Example 2.
Figure 9B:
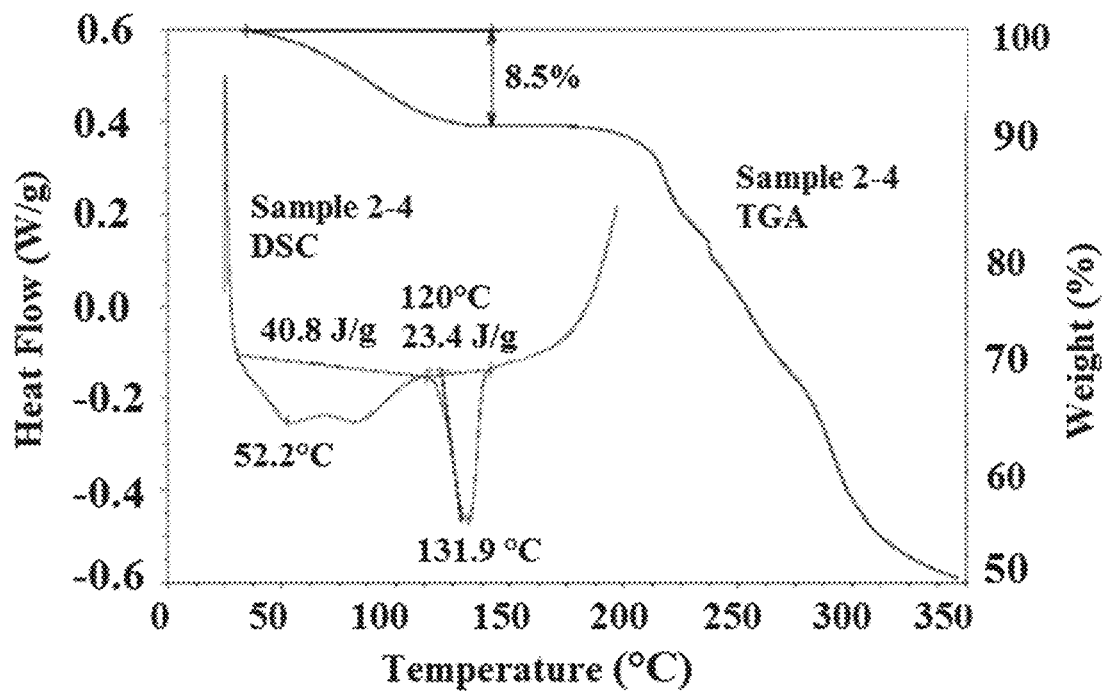
FIG. 9B is a DSC and TGA graph for sample 2-4 (Example 6). The x-axis is temperature measured in ° C., the left y-axis heat flow measured in (W/g), and the right y-axis is weight measured in percent. Experimental procedures for DSC and TGA collection are given in Example 2.
Figure 10A:
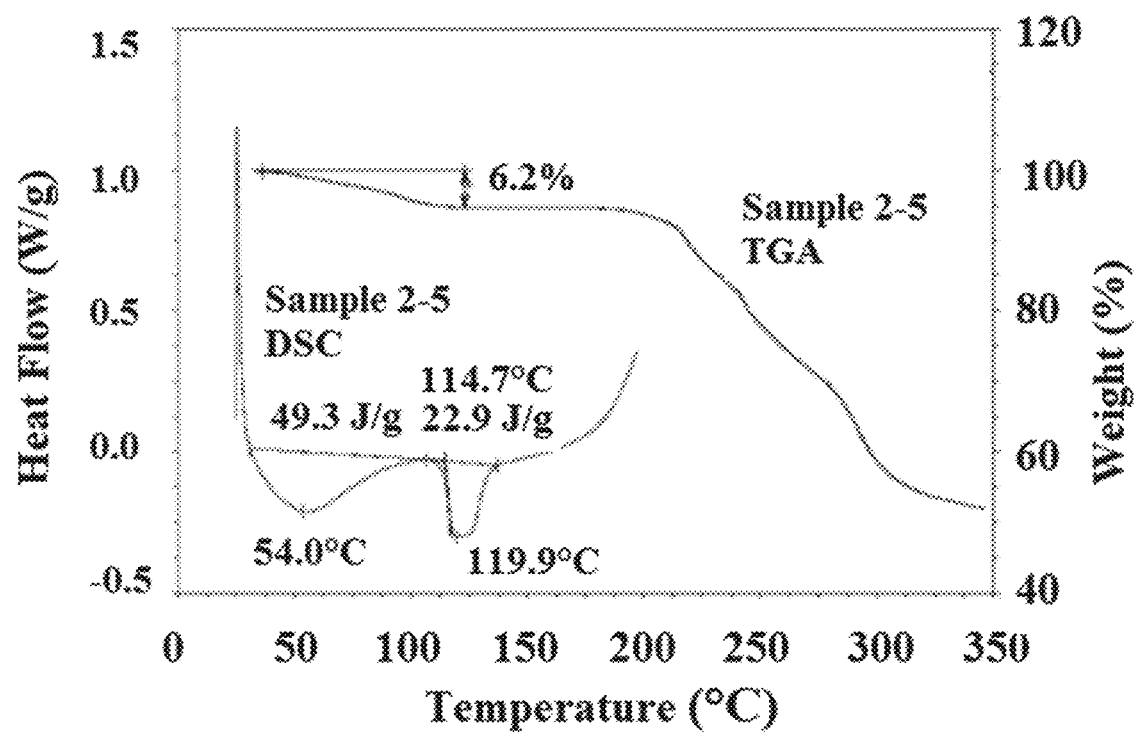
FIG. 10A is a DSC and TGA graph for sample 2-5 (Example 6). The x-axis is temperature measured in ° C., the left y-axis heat flow measured in (W/g), and the right y-axis is weight measured in percent. Experimental procedures for DSC and TGA collection are given in Example 2.
Figure 10B:
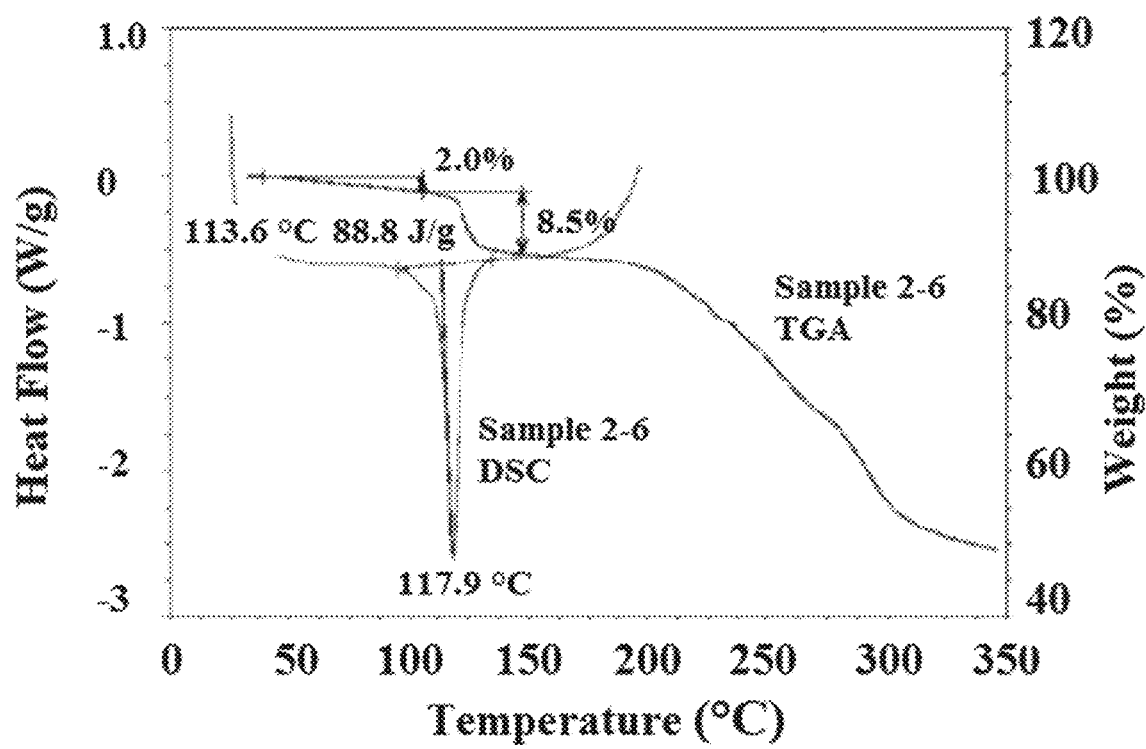
FIG. 10B is a DSC and TGA graph for sample 2-6 (Example 6). The x-axis is temperature measured in ° C., the left y-axis heat flow measured in (W/g), and the right y-axis is weight measured in percent. Experimental procedures for DSC and TGA collection are given in Example 2.
Figure 11A:
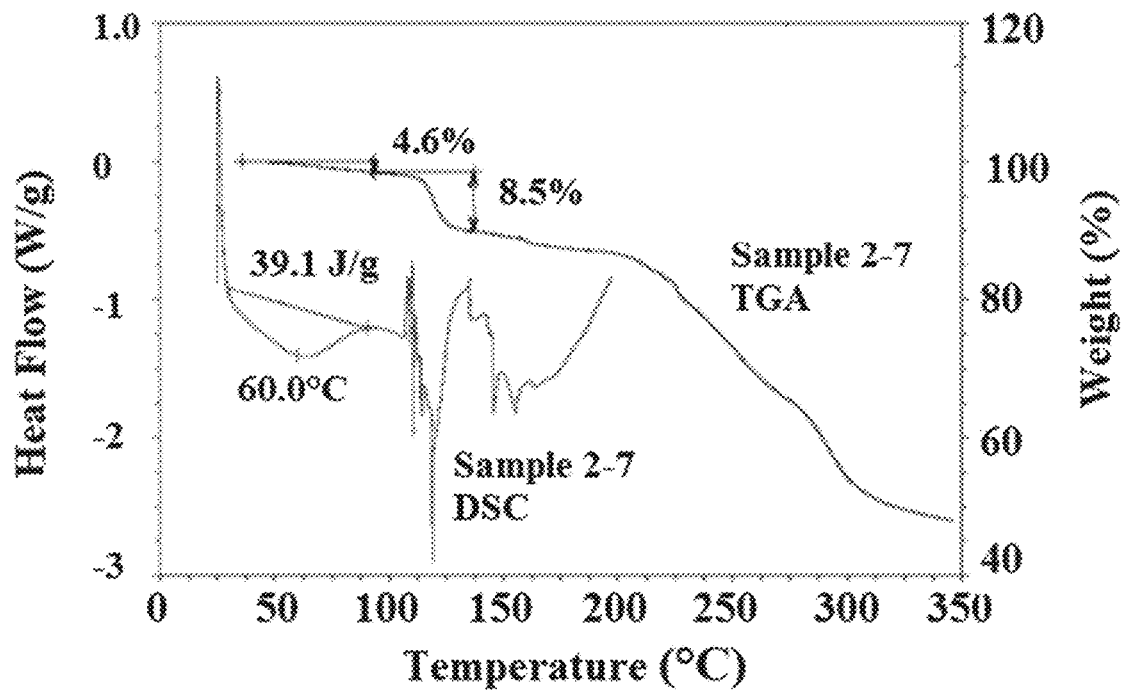
FIG. 11A is a DSC and TGA graph for sample 2-7 (Example 6). The x-axis is temperature measured in ° C., the left y-axis heat flow measured in (W/g), and the right y-axis is weight measured in percent. Experimental procedures for DSC and TGA collection are given in Example 2.
Figure 11B:
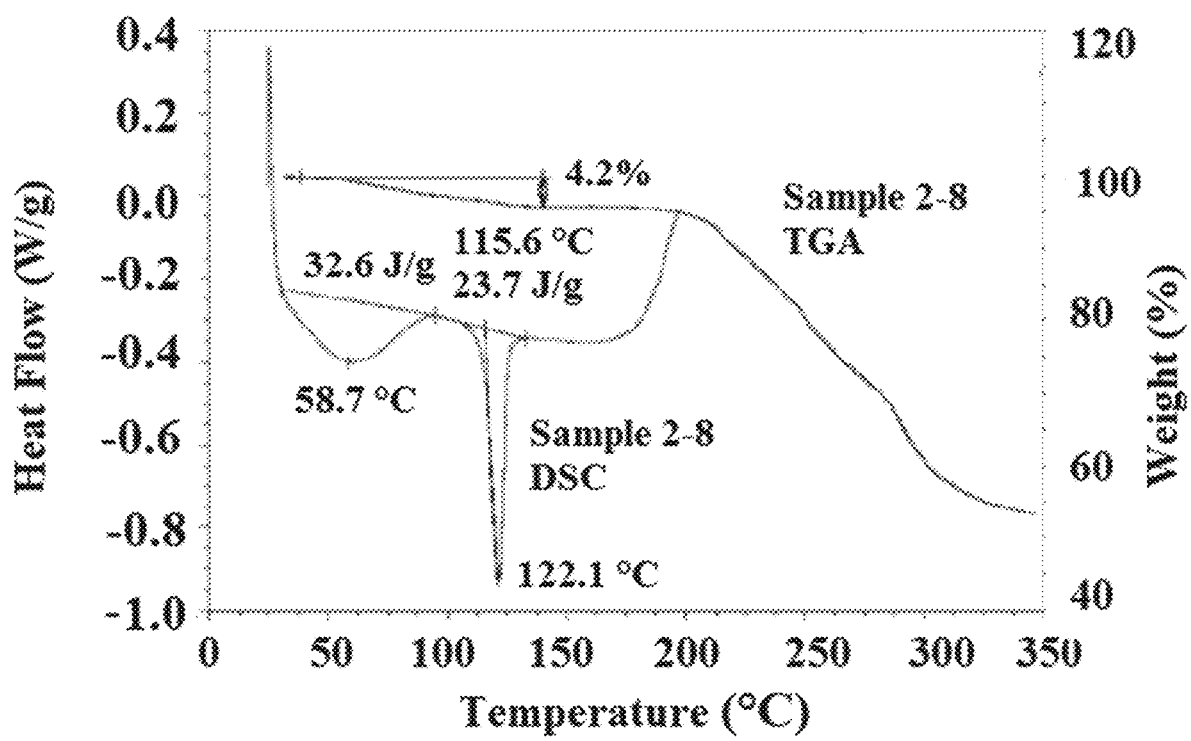
FIG. 11B is a DSC and TGA graph for sample 2-8 (Example 6). The x-axis is temperature measured in ° C., the left y-axis heat flow measured in (W/g), and the right y-axis is weight measured in percent. Experimental procedures for DSC and TGA collection are given in Example 2.

The seven samples (Samples 2-2, 2-3, 2-4, 2-5, 2-6, 2-7 and 2-8) were analyzed by DSC, TGA, $^1$H-NMR and IC (Table 10, FIG. 8A, FIG. 8B, FIG. 9A, FIG. 9B, FIG. 10A, FIG. 10B, FIG. 11A, and FIG. 11B) as well as by XRPD following 6 days storage at 25° C./60% relative humidity (RH) (all samples remained crystalline/poorly crystalline following stability). All samples retained roughly half an equivalent of sulfate, but contained a relatively large amount of residual solvent. An overlay of the X-ray diffractograms of amorphous samples 2-9, 2-10, and 2-11 is shown in FIG. 7B.

TABLE 10

Characterization of crystalline Compound 2 samples

| Sample ID | Solvent | DSC | TGA | $^1$HNMR | IC (corrected for TGA) |
|---|---|---|---|---|---|
| 2-2 | Isobutanol | Endo 113.8° C. | 8.3% ambient-140° C. | 1.1 eq isobutanol | 0.45 eq |
| 2-3 | Acetone | Endo 30-95° C. Endo 100-145° C. | 7.6% ambient-140° C. | 0.5 eq acetone | 0.46 eq |
| 2-4 | MEK | Broad complex endo 30-115° C. Endo 115-145° C. | 8.5% ambient-140° C. | 0.8 eq MEK | 0.45 eq |
| 2-5 | MIBK | Broad endo 30-105° C. Endo 114.7° C. | 5.2% ambient-110° C. | 0.2 eq MIBK | 0.46 eq |
| 2-6 | EtOAc | Sharp endo 113.6° C. | 2.0% ambient-100° C. | 0.9 eq EtOAc | 0.46 eq |
| 2-7 | iPrOAc | Endo 30-90° C. | 1.6% ambient-90° C. | 0.8 eq iPrOAc | 0.45 eq |
| 2-8 | THF | Endo 30-100° C. Sharper endo 115.6° C. | 4.2% ambient-130° C. | 0.7 eq THF | 0.45 eq |

¹HNMR spectrum were taken for all samples and listed below.

Sample 2-2

¹H NMR (400 MHz, DMSO-d$_6$) δ ppm 0.83 (d, J=6.69 Hz, 7H), 0.99-1.26 (m, 14H), 1.61 (dt, J=13.26, 6.63 Hz, 1H), 3.73-3.87 (m, 2H), 4.03-4.18 (m, 1H), 4.18-4.51 (m, 4H), 4.66-4.92 (m, 1H), 4.70-4.90 (m, 1H), 4.72-4.88 (m, 1H), 5.81 (br s, 1H), 5.93-6.11 (m, 2H), 7.10-7.26 (m, 3H), 7.14-7.26 (m, 1H), 7.30-7.41 (m, 2H), 7.94 (br s, 1H)

Sample 2-3

¹H NMR (400 MHz, DMSO-d$_6$) δ ppm 1.00-1.26 (m, 13H), 2.09 (s, 3H), 3.74-3.87 (m, 2H), 4.10 (br d, J=7.70 Hz, 1H), 4.22-4.50 (m, 3H), 4.81 (quin, J=6.28 Hz, 1H), 5.71-5.90 (m, 1H), 5.96-6.15 (m, 2H), 7.12-7.26 (m, 3H), 7.31-7.41 (m, 2H), 7.79-8.07 (m, 1H)

Sample 2-4

¹H NMR (400 MHz, DMSO-d$_6$) δ ppm 0.91 (t, J=7.33 Hz, 3H), 1.01-1.28 (m, 13H), 2.08 (s, 2H), 3.72-3.89 (m, 2H), 4.10 (br d, J=8.08 Hz, 1H), 4.23-4.47 (m, 3H), 4.81 (quin, J=6.25 Hz, 1H), 5.69-5.89 (m, 1H), 5.94-6.13 (m, 2H), 7.14-7.25 (m, 3H), 7.32-7.41 (m, 2H), 7.79-8.11 (m, 1H)

Sample 2-5

¹H NMR (400 MHz, DMSO-d$_6$) δ ppm 0.86 (d, J=6.69 Hz, 1H), 0.98-1.33 (m, 13H), 2.02-2.09 (m, 1H), 4.03-4.17 (m, 1H), 4.22-4.50 (m, 3H), 4.81 (quin, J=6.25 Hz, 1H), 5.81 (br s, 1H), 5.93-6.15 (m, 2H), 7.11-7.27 (m, 3H), 7.31-7.41 (m, 2H), 7.77-8.21 (m, 1H)

Sample 2-6

¹H NMR (400 MHz, DMSO-d$_6$) δ ppm 0.98-1.28 (m, 15H), 2.00 (s, 3H), 3.99-4.14 (m, 3H), 4.21-4.49 (m, 3H), 4.81 (quin, J=6.22 Hz, 1H), 5.82 (br s, 1H), 5.93-6.14 (m, 2H), 7.11-7.26 (m, 3H), 7.29-7.42 (m, 2H), 7.79-8.17 (m, 1H)

Sample 2-7

¹H NMR (400 MHz, DMSO-d$_6$) δ ppm 0.92-1.28 (m, 17H), 1.97 (s, 2H), 4.04-4.16 (m, 1H), 4.20-4.51 (m, 3H), 4.71-4.93 (m, 2H), 5.82 (br s, 1H), 6.14 (m, 2H), 7.11-7.28 (m, 3H), 7.31-7.43 (m, 2H), 7.75-8.21 (m, 1H)

Sample 2-8

¹H NMR (400 MHz, DMSO-d$_6$) δ ppm 0.81-1.11 (m, 13H), 1.19 (s, 1H), 1.53-1.66 (m, 1H), 3.87-4.01 (m, 1H), 4.06-4.32 (m, 3H), 4.64 (quin, J=6.25 Hz, 1H), 5.55-5.75 (m, 1H), 5.77-5.97 (m, 2H), 6.94-7.10 (m, 3H), 7.13-7.26 (m, 2H), 7.66-7.96 (m, 1H)

Example 7. Failure to Crystallize Amorphous Malonate Salt (Compound 4)

Figure 12A:
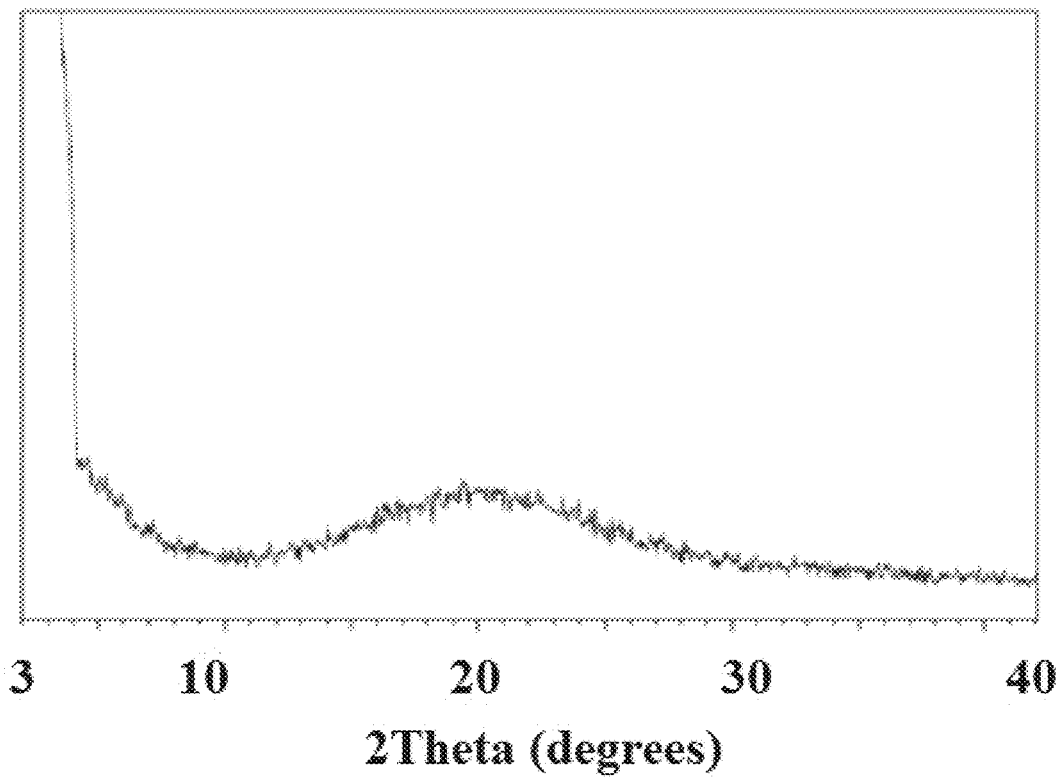
FIG. 12A is the XRPD pattern of amorphous Compound 4 (sample 3-12) as discussed in Example 7. The x-axis is 2Theta measured in degrees and the y-axis is intensity measured in counts. No crystallization of a malonate salt was observed regardless of the solvent used.
Figure 12B:
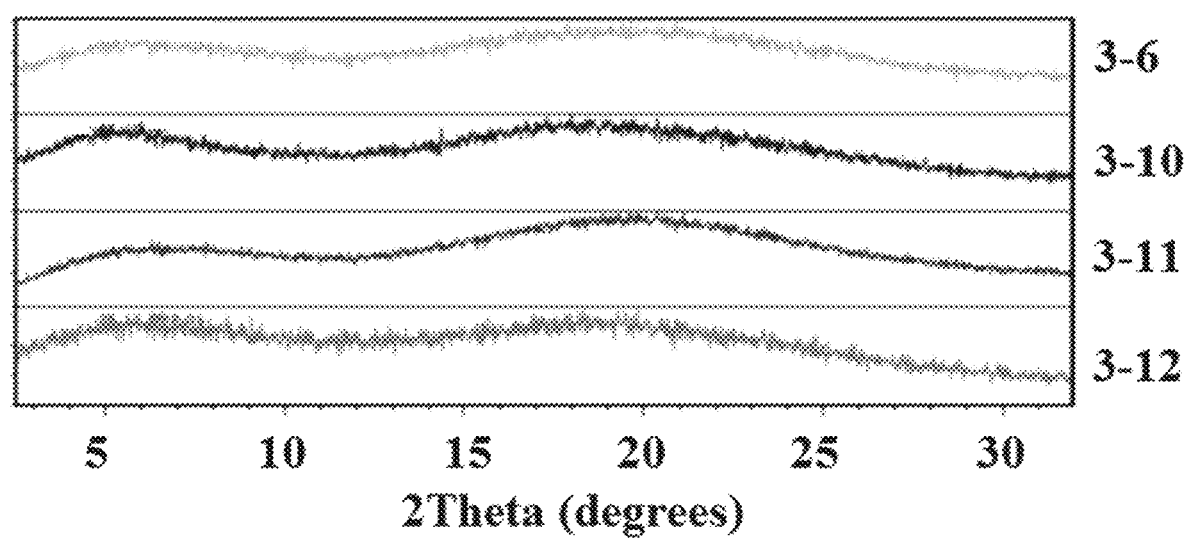
FIG. 12B is an overlay of XRPD diffractograms of amorphous samples (samples 3-6, 3-3-11, and 3-12) identified from the attempted crystallization of compound 1 with malonate salt (Example 7). The x-axis is 2Theta measured in degrees and the y-axis is intensity measured in counts.
Figure 13A:
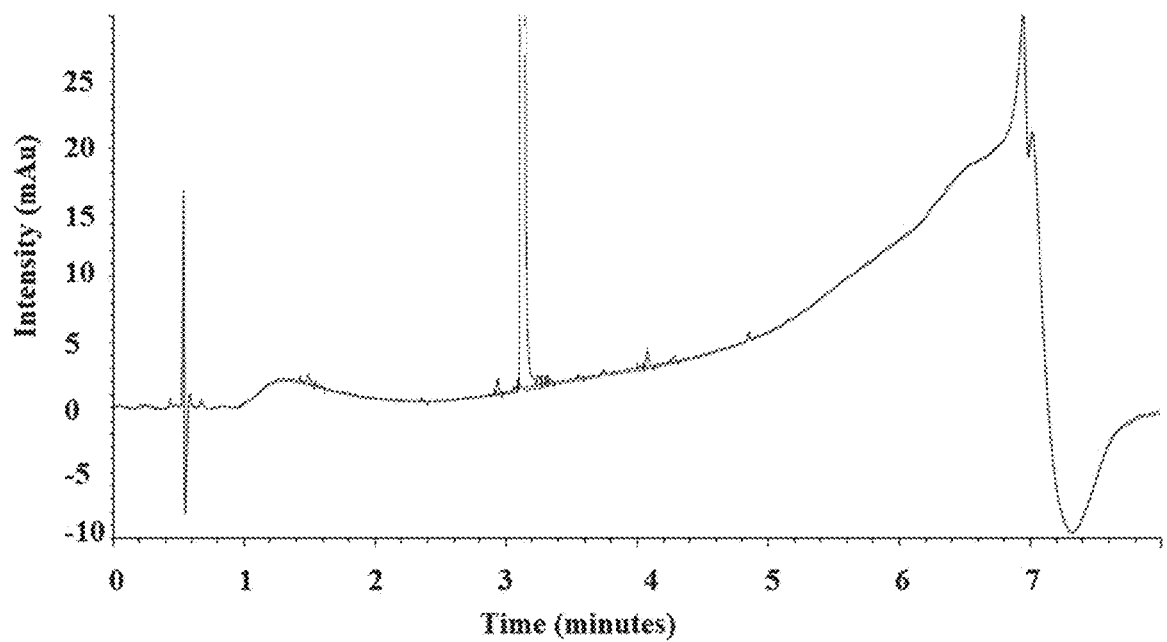
FIG. 13A is the HPLC chromatogram of sample 3-12 from the attempted crystallizations of compound 1 with malonate salt as described in Example 7. The sample was 99.2% pure. The x-axis is time measured in minutes and the y-axis is intensity measured in mAu.

As shown in Example 3, a crystalline oxalate salt was identified when determining appropriate salts for Compound 1, but oxalate salt Compound 4 could not be carried forward in clinical trials due to its potential for causing kidney stones. Therefore, crystallization of the chemically related malonate salt (Compound 5) was attempted using the same 11 solvents as for the hemi-sulfate salt. Compound 1 (12×50 mg, samples 3-1, 3-2, 3-3, 3-4, 3-5, 3-6, 3-7, 3-8, 3-9, 3-10, 3-11, and 3-12) was dissolved in t-butanol (20 vol) and the solutions were then treated with 1 equivalence of a malonic acid stock solution (1 M in THF). The samples were then frozen with the solvent removed by lyophilisation. To samples 3-1, 3-2, 3-3, 3-4, 3-5, 3-6, 3-7, 3-8, 3-9, 3-10, and 3-11, relevant solvent (5 volumes) was added at room temperature. Any resulting solutions were allowed to evaporate under ambient conditions, while gums or solids were matured at 25-50° C. (1° C./min between temperatures and 4 hour at each temperature) for 5 days. The solids were analyzed by XRPD (FIG. 12B), but all samples were found to either form a gum or were amorphous (FIG. 12B). Results are shown in Table 11. The one solid (amorphous) sample (3-12) was analyzed by ¹H-NMR and HPLC, and was found to contain around 1 equivalence of malonic acid (peaks overlap) as well as 0.6 eq. t-BuOH. The compound was 99.2% pure (FIG. 13A). FIG. 12A is an XRDP of sample 3-12 and FIG. 13A is the HPLC chromatograph of sample 3-12.

Sample 3-12

¹H NMR (400 MHz, DMSO-d$_6$) δ ppm 0.81-1.11 (m, 13H), 1.19 (s, 1H), 1.53-1.66 (m, 1H), 3.87-4.01 (m, 1H), 4.06-4.32 (m, 3H), 4.64 (quin, J=6.25 Hz, 1H), 5.55-5.75 (m, 1H), 5.77-5.97 (m, 2H), 6.94-7.10 (m, 3H), 7.13-7.26 (m, 2H), 7.66-7.96 (m, 1H)

TABLE 11

Crystallization Conditions of Amorphous Malonate Salt Compound 4

| Sample ID | Solvent | Observation after 5 volumes | Observation after 5 days maturation/ evaporation | XRPD |
|---|---|---|---|---|
| 3-1 | IPA | Clear solution* | Clear gum | — |
| 3-2 | Isobutanol | Clear solution* | Clear gum | — |
| 3-3 | Acetone | Clear solution* | Clear gum | — |
| 3-4 | MEK | Clear solution* | Clear gum | — |
| 3-5 | MIBK | Solution & some gum | Clear gum | — |
| 3-6 | EtOAc | Clear solution* | Clear gum & crystal-like appearance | Amorphous |
| 3-7 | iPrOAc | Gum | Clear gum | — |
| 3-8 | THF | Clear solution* | Clear gum | — |
| 3-9 | TBME | Thick suspension | Clear gum | — |
| 3-10 | Toluene | White gum/solid | White gum | Amorphous |
| 3-11 | Heptane | White solid (static) | White gum | Amorphous |

TABLE 11-continued

Crystallization Conditions of Amorphous Malonate Salt Compound 4

| Sample ID | Solvent | Observation after 5 volumes | Observation after 5 days maturation/ evaporation | XRPD |
|---|---|---|---|---|
| 3-12 | — | (White solid- no solvent) | (Sticky white solid-ambient conditions) | Amorphous |

*Evaporated at room temperature

Example 8. Failure of Adequate Salt Formation Using Liquid Assisted Grinding (LAG)

A liquid assisted grinding (LAG) study to determine appropriate salts other than hemi-sulfate was performed using the 14 acidic counter ions in Table 12.

TABLE 12

Counter-ion stock solutions used in LAG Crystallization

| Counter-ion | Solvent (1M) |
|---|---|
| Pamoic | DMSO |
| Malonic | THF |
| D-Glucuronic | Water |
| DL-Mandelic | THF |
| D-Gluconic | THF |
| Glycolic | THF |
| L-Lactic | THF |
| Oleic | THF |
| L-Ascorbic | Water |
| Adipic | THF (heat) |
| Caproic | THF |
| Stearic | THF |
| Palmitic | THE |
| Methanesulfonic | THF |

Figure 13B:
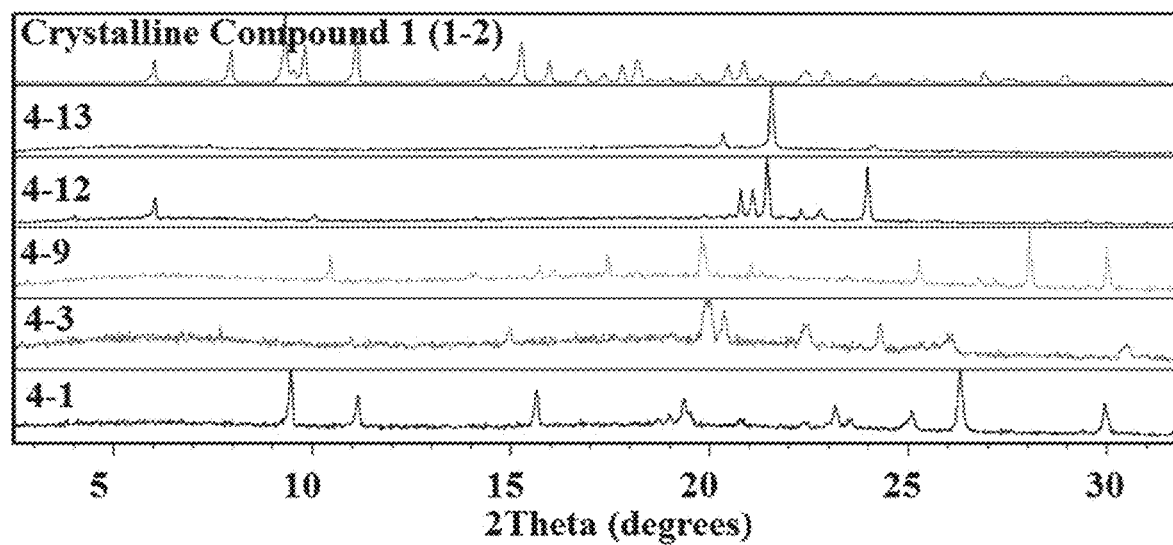
FIG. 13B is an overlay of XRPD diffractograms of solid samples obtained from the crystallization using LAG (samples 4-13, 4-12, 4-9, 4-3, and 4-1) compared to Compound 1 (sample 1-2) as described in Example 8. All the XRDP match the patterns of the crystalline acid counter ion with no additional peaks. The x-axis is 2Theta measured in degrees and the y-axis is intensity measured in counts.

Compound 1 (30 mg) was placed in HPLC vials with two 3 mm ball bearings. The materials were wetted with solvent (15 µl ethanol, sample 4-1, 4-2, 4-3, 4-4, 4-5, 4-6, 4-7, 4-8, 4-9, 4-10, 4-11, 4-12, 4-13, and 4-14) and 1 equivalence of the acid counter-ion was added. The samples were then ground for 2 hours at 650 rpm using a Fritsch milling system with an Automaxion adapter. Most of the samples after grinding were found to be clear gums and were not analyzed further (Table 13). Those that were observed to contain solid were analyzed by XRPD and, in all cases, the patterns obtained were found to match those of the crystalline acid counter ion with no additional peaks (FIG. 13B).

TABLE 13

Observations and XRPD Results from LAG of Compounds 1

| Sample ID | Acid | Observation after grinding | XRPD |
|---|---|---|---|
| 4-1 | Pamoic | Yellow gum/solid | Pamoic acid & amorphous halo |
| 4-2 | Malonic | Clear gum | — |
| 4-3 | D-Glucuronic | White gum/solid | D-Glucuronic acid & amorphous halo |
| 4-4 | DL-Mandelic | Clear gum | — |
| 4-5 | D-Gluconic | Clear gum | — |
| 4-6 | Glycolic | Clear gum | — |
| 4-7 | L-Lactic | Clear gum | — |
| 4-8 | Oleic | Clear gum | — |
| 4-9 | L-Ascorbic | White gum/solid | L-Ascorbic acid & amorphous halo |
| 4-10 | Adipic | Clear gum | — |
| 4-11 | Caproic | Clear gum | — |
| 4-12 | Stearic | White gum/solid | Stearic acid & amorphous halo |
| 4-13 | Palmitic | White gum/solid | Palmitic acid & amorphous halo |
| 4-4 | Methanesulfonic | Clear gum | — |

Example 9. Failure to Obtain Adequate Salt Formation using Methyl Ethyl Ketone (MEK)

Methyl ethyl ketone (MEK) was next utilized as a solvent to study appropriate salts other than the hemi-sulfate salt. Using the 14 acidic counter ions in Table 12, the study was performed by dissolving Compound 1 (50 mg) in MEK (20 vol) at room temperature. The solutions were treated with 1 equivalence of the selected counter-ions (Table 12). The samples were then cooled down to 5° C. at 0.1° C./min and stirred at this temperature overnight. All samples were allowed to evaporate under ambient conditions and any solids observed were analyzed by XRPD. This evaporation mainly produced gums, with the exception of the samples with steric acid (sample 4-12) and palmitic acid (sample 5-13), which afforded glassy solvents. These solids were amorphous by XRPD, but no crystalline forms of the salt were obtained. Results are shown in Table 14. (FIG. 13A).

TABLE 14

Results from dissolving Compound 1 in MEK (20 volumes)

| Sample ID | Acid | Solvent for acid at 1M | Observation upon acid addition | Observation upon cooling | Observation upon evaporation |
|---|---|---|---|---|---|
| 5-1 | Pamoic | DMSO | Yellow solution | Yellow solution | Yellow gum |
| 5-2 | Malonic | THF | Solution | Solution | Clear gum |
| 5-3 | D-Glucuronic | Water | Solution | Solution | Clear gum |
| 5-4 | DL-Mandelic | THF | Solution | Solution | Clear gum |
| 5-5 | D-Gluconic | THF | White precipitate | Turbid solution | Clear gum |

TABLE 14-continued

Results from dissolving Compound 1 in MEK (20 volumes)

| Sample ID | Acid | Solvent for acid at 1M | Observation upon acid addition | Observation upon cooling | Observation upon evaporation |
|---|---|---|---|---|---|
| 5-6 | Glycolic | THF | Solution | Solution | Clear gum |
| 5-7 | L-Lactic | THF | Solution | Solution | Clear gum |
| 5-8 | Oleic | THF | Solution | Solution | Clear gum |
| 5-9 | L-Ascorbic | Water | Solution | Solution | Yellow gum |
| 5-10 | Adipic | THF (heat) | Solution | Solution | Clear gum |
| 5-11 | Caproic | THF | Solution | Solution | Clear gum |
| 5-12 | Stearic | THF | Solution | Turbid solution | Clear glassy solid* |
| 5-13 | Palmitic | THF | Solution | Solution | Clear glassy solid* |
| 5-14 | Methanesulfonic | THF | Solution | Solution | Clear gum |

Stock solution prepared prior to acid addition
*Samples were analyzed by XRPD and gave amorphous patterns plus peaks from the acid counter ion Since all samples were amorphous, all samples were redissolved in MEK (5 vol) and cyclohexane was added (20 vol antisolvent) at room temperature followed by 1 hour of stirring at 25° C. The samples were then matured between 50-5° C. (1° C./min between temperatures, 4 hours at each temperature) for 2 days before the cycle was changed to 50-25° C. for a further 4 days. The samples were observed by eye following maturation. Results are shown in Table 15. Following the maturation, all samples except 5-1 (with pamoic acid) were found to be gums. Sample 5-1, a yellow solid, was analyzed by XRPD, and the pattern was found to match the known form of pamoic acid (FIG. 14B), and therefore no crystalline forms of the salt were obtained.

TABLE 15

Results from redissolving Compound 1 in MEK (5 volumes) and antisolvent

| Sample ID | Immediate Observation | Observation after 10 minutes | Observation after 60 minutes | Observation after Maturation |
|---|---|---|---|---|
| 5-1 | Precipitate | Gum | Gum | Yellow suspension** |
| 5-2 | Precipitate | Gum | Gum | Gum |
| 5-3 | Precipitate/gum | Gum | Gum | Gum |
| 5-4 | Precipitate | Gum | Gum | Gum |
| 5-5 | Precipitate/gum | Gum | Gum | Gum |
| 5-6 | Precipitate | Gum | Gum | Gum |
| 5-7 | Precipitate | Gum | Gum | Gum |
| 5-8 | Precipitate | Light suspension | Gum | Gum |
| 5-9 | Precipitate | Gum | Gum | Gum |
| 5-10 | Precipitate | Gum | Gum | Gum |
| 5-11 | Precipitate | Light suspension | Gum | Gum |
| 5-12 | Precipitate | Light suspension | Gum | Gum |
| 5-13 | Precipitate | Light suspension | Gum | Gum |
| 5-14 | Precipitate | Gum | Gum | Gum |

**Sample analyzed by XRPD with pattern matching known form of pamoic acid (no additional peaks

Example 10. Failure to Obtain Adequate Salt Formation using Ethyl Acetate

Figure 14A:
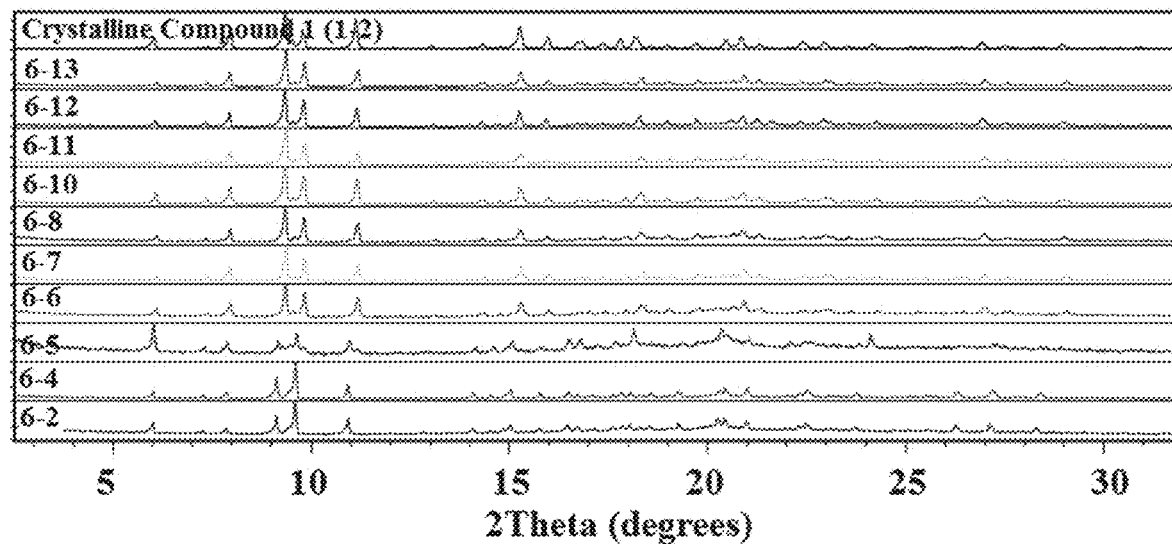
FIG. 14A is an overlay of XRPD diffractograms of samples obtained from utilizing ethyl acetate as a crystallization solvent (samples 6-13, 6-12, 6-11, 6-10, 6-8, 6-7, 6-6, 6-5, 6-4, and 6-2) compared to crystalline Compound 1 (sample 1-2) as described in Example 10. The XRPD patterns were generally found to match the Compound 1 pattern with the exception of samples 6-2, 6-4, and 6-5 that exhibit slight differences. The x-axis is 2Theta measured in degrees and the y-axis is intensity measured in counts.
Figure 14B:
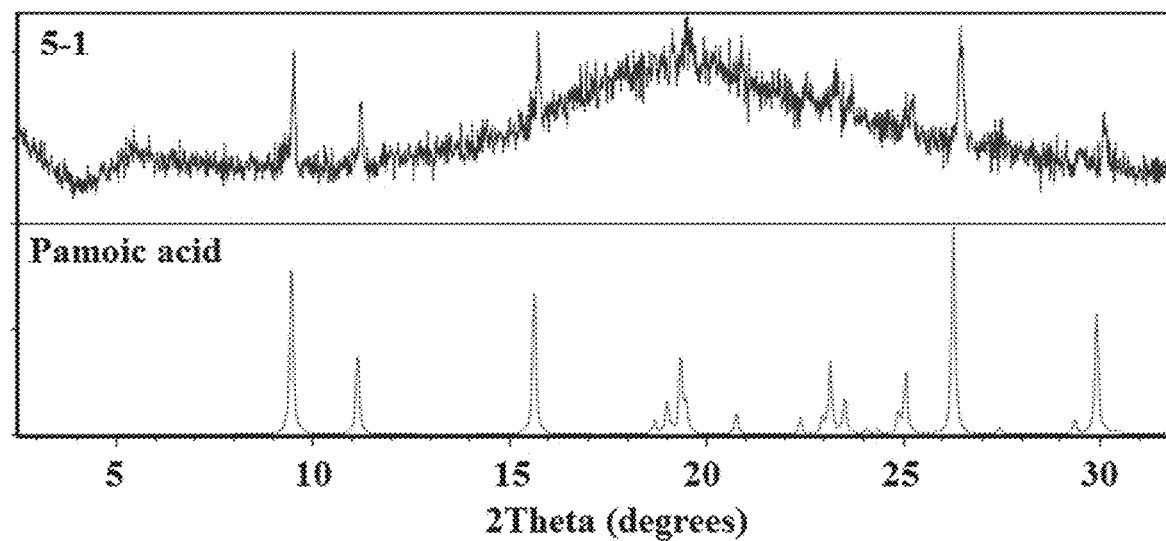
FIG. 14B is an overlay of XRPD diffractogram of sample 5-1 following a second dissolution in MEK and the addition of the antisolvent cyclohexane and pamioc acid as described in Example 9. Sample 5-1, crystallized in pamioc acid, was a solid following maturation, but the XRPD pattern matched the pattern of pamioc acid.
Figure 15A:
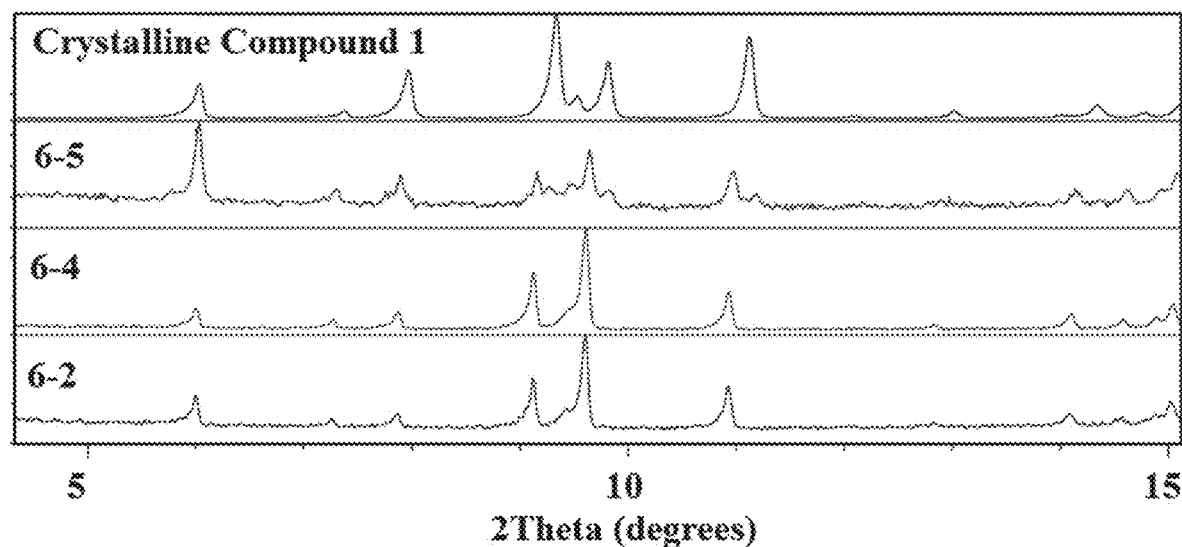
FIG. 15A is an overlay of XRPD diffractograms of samples obtained from utilizing ethyl acetate as a crystallization solvent (samples 6-5, 6-4, and 6-2) compared to crystalline Compound 1 (sample 1-2) as described in Example 10. The XRPD patterns were generally found to match the Compound 1 pattern with the exception of samples 6-2, 6-4, and 6-5 that exhibit slight differences. The x-axis is 2Theta measured in degrees and the y-axis is intensity measured in counts and labeled with the acid used in crystallization.

Ethyl acetate was next utilized to study appropriate salts other than hemi-sulfate salt. Utilizing the 14 acidic counter ions in Table 12, the study was performed by dissolving Compound 1 (50 mg) in ethyl acetate (20 vol) at 50° C. The solutions were treated with 1 equivalent of the selected counter-ions (Table 12). The samples were then cooled down to 5° C. at 0.1° C./min and stirred at this temperature for 4 days. The solutions were allowed to evaporate under ambient conditions while any solids were analyzed by XRPD. The results from the crystallizations using ethyl acetate are in Table 16. In contrast to Example 8 where MEK was the solvent, the majority of samples were observed to be suspensions following cooling of the acid:compound mixture (those that were solutions were allowed to evaporate under ambient conditions). However, the XRPD diffractograms were generally found to match crystalline Compound 1. Samples 6-2, 6-4, and 6-5 have some slight differences (FIG. 14A and FIG. 15A). No crystalline forms of the salt were obtained.

TABLE 16

Results from dissolving Compound 1 in EtOAc (20 volumes)

| Sample ID | Acid | Solvent for acid at 1M | Observation upon acid addition | Observation upon Cooling | XRPD | Observation upon Evaporation |
|---|---|---|---|---|---|---|
| 6-1 | Pamoic | DMSO | Yellow solution | Yellow solution* | — | Gum |
| 6-2 | Malonic | THF | Solution | White suspension | Slight differences to freebase | — |
| 6-3 | D-Glucuronic | Water | Solution | Solution* | — | Gum |
| 6-4 | DL-Mandelic | THF | Solution | White suspension | Slight differences to freebase | — |
| 6-5 | D-Gluconic | THF | White precipitate | Possible white gum | Slight differences to freebase | — |
| 6-6 | Glycolic | THF | Solution | White suspension | Freebase | — |
| 6-7 | L-Lactic | THF | Solution | White suspension | Freebase | — |
| 6-8 | Oleic | THF | Solution | White suspension | Freebase | — |
| 6-9 | L-Ascorbic | Water | Solution | Solution* | — | White solid on side/ yellow gum-amorphous |
| 6-10 | Adipic | THF (heat) | Solution | White suspension | Freebase | — |
| 6-11 | Caproic | THF | Solution | White suspension | Freebase | — |
| 6-12 | Stearic | THF | Solution | White suspension | Freebase | — |
| 6-13 | Palmitic | THF | Solution | White suspension | Freebase | — |
| 6-14 | Methanesulfonic | THF | White precipitate | Solution/ clear gum* | — | Clear gum |

Example 11. Chemical Purity Determination by HPLC

Purity analysis in Example 2 and Example 4 was performed on an Agilent HP1100 series system equipped with a diode array detector and using ChemStation software vB.04.03 using the method shown in Table 17.

TABLE 17

HPLC method for chemical purity determinations

| Parameter | Value |
|---|---|
| Type of method | Reverse phase with gradient elution |
| Sample Preparation | 0.5 mg/ml in acetonitrile:water 1:1 |
| Column | Supelco Ascentis Express C18, 100 × 4.6 mm, 2.7 μm |
| Column Temperature (° C.) | 25 |
| Injection (μl) | 5 |
| Wavelength, Bandwidth (nm) | 255, 90 |
| Flow Rate (ml/min) | 2 |
| Phase A | 0.1% TFA in water |
| Phase B | 0.085% TFA in acetonitrile |

| Timetable | Time (min) | % Phase A | % Phase B |
|---|---|---|---|
| | 0 | 95 | 5 |
| | 6 | 5 | 95 |
| | 6.2 | 95 | 5 |
| | 8 | 95 | 5 |

Example 12. X-Ray Powder Diffraction (XRPD) Techniques

The XRPD patterns in Examples 2, 3, 4, 5, 6, 7, 8, and 9 were collected on a PANalytical Empyrean diffractometer using Cu K☐ radiation (45 kV, 40 mA) in transmission geometry. A 0.5° slit, 4 mm mask and 0.4 rad Soller slits with a focusing mirror were used on the incident beam. A PIXcel$^{3D}$ detector, placed on the diffracted beam, was fitted with a receiving slit and 0.04 rad Soller slits. The instrument is performance checked using silicon powder on a weekly basis. The software used for data collection was X'Pert Data Collector v. 5.3 and the data were analyzed and presented using Diffrac Plus EVA v. 15.0.0.0 or Highscore Plus v. 4.5. Samples were prepared and analyzed in either a metal or Millipore 96 well-plate in transmission mode. X-ray transparent film was used between the metal sheets on the metal well-plate and powders (approximately 1-2 mg) were used as received. The Millipore plate was used to isolate and analyze solids from suspensions by adding a small amount of suspension directly to the plate before filtration under a light vacuum.

The scan mode for the metal plate used the gonio scan axis, whereas a 2θ scan was utilized for the Millipore plate. A performance check was carried out using silicon powder (metal well-plate). The details of the data collection were an angular range of 2.5 to 32.0° 2θ, a step size of 2θ, and a total collection time of 2.07 minutes.

Samples were also collected on a Bruker D8 diffractometer using Cu K☐ radiation (40 kV, mA), θ-2θ goniometer, and divergence of V4 and receiving slits, a Ge monochromator and a Lynxeye detector. The instrument is performance checked using a certified Corundum standard (NIST 1976). The software used for data collection was DiffracPlus XRD Commander v2.6.1 and the data were analyzed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection were an angular range of 2 to 42° 2θ, a step size of 0.05° 2θ, and collection time of 0.5 s/step.

Example 13. Synthesis of Amorphous Compound 2

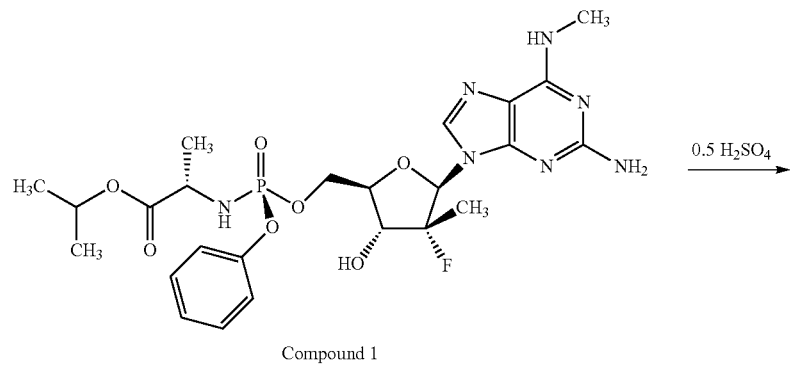

Compound 1

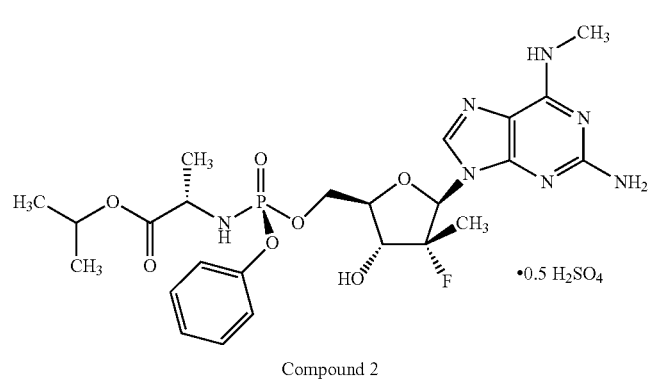

Compound 2

A 250 mL flask was charged with MeOH (151 mL) and the solution was cooled to 0-5° C. A concentrated solution of H$_2$SO$_4$ was added dropwise over 10 minutes. A separate flask was charged with Compound 1 (151 g) and acetone (910 mL), and the H$_2$SO$_4$/MeOH solution was added dropwise at 25-30° C. over 2.5 hours. A large amount of solid was precipitated. After the solution was stirred for 12-15 hours at 25-30° C., the mixture was filtered, washed with MeOH/acetone (25 mL/150 mL), and dried at 55-60° C. in vacuum to afford Compound 2 (121 g, 74%).

Analytic Method for Compound 2: The purity of Compound 2 was obtained using an Agilent 1100 HPLC system with a Waters XTerra Phenyl 5 μm 4.6*250 mm column with the following conditions: 1 mL/min flow rate, read at 254 nm, 30° C. column temperature, 10 μL injection volume, and a 30 minute run time. The sample was dissolved in ACN: water (90:10, v/v). The Gradient method for separation is shown below. $R_t$ (min) of Compound 2 was approximately 12.0 minutes.

| Time (min) | 0.1% $H_3PO_4$ in Water (A) % | Acetonitrile (B) % |
|---|---|---|
| 0 | 90 | 10 |
| 20 | 20 | 80 |
| 20.1 | 90 | 10 |
| 30 | 90 | 10 |

$^1$HNMR: (400 MHz, DMSO-$d_6$): δ 8.41 (br, 1H), 7.97 (s, 1H), 7.36 (t, J=8.0 Hz, 2H), 7.22 (d, J=8.0 Hz, 2H), 7.17 (t, J=8.0 Hz, 1H), 6.73 (s, 2H), 6.07 (d, J=8.0 Hz, 1H), 6.00 (dd, J=12.0, 8.0 Hz, 1H), 5.81 (br, 1H), 4.84-4.73 (m, 1H), 4.44-4.28 (m, 3H), 4.10 (t, J=8.0 Hz, 2H), 3.85-3.74 (m, 1H), 2.95 (s, 3H), 1.21 (s, J=4.0 Hz, 3H), 1.15-1.10 (m, 9H).

Example 14. Characterization of Compound 2

Figure 15B:
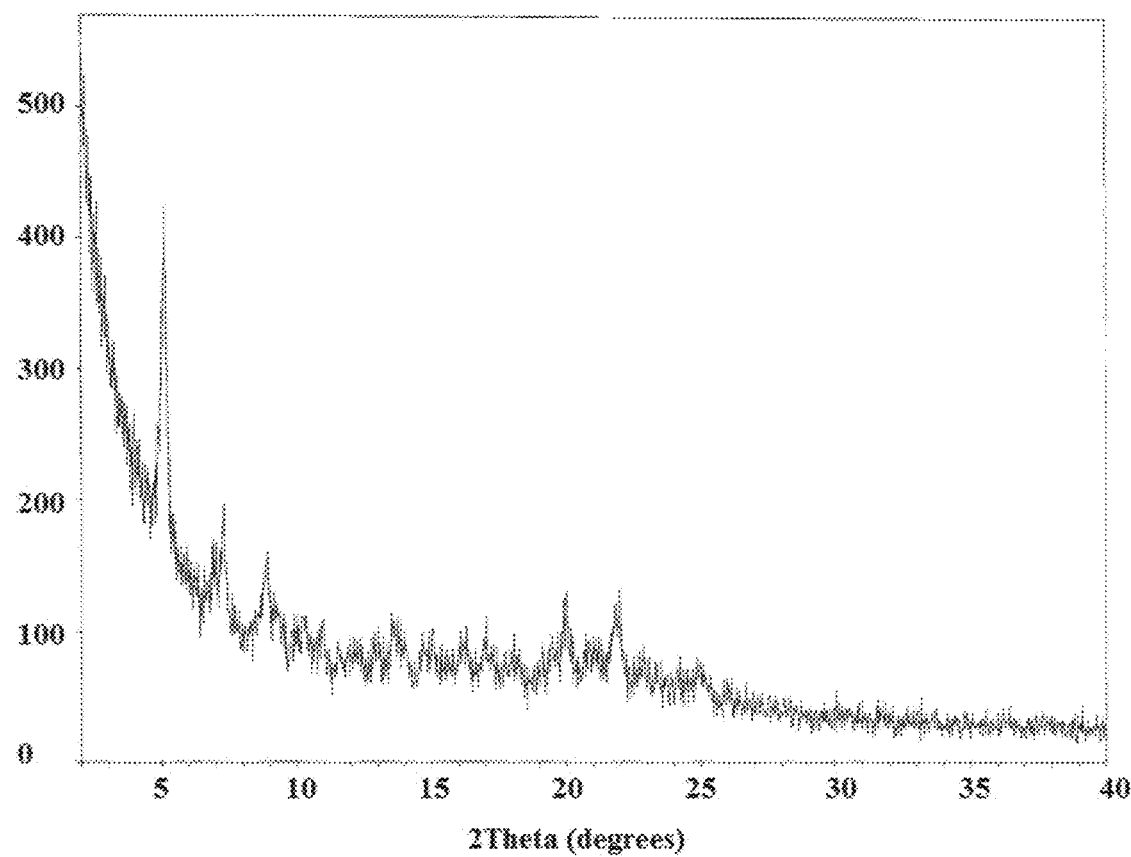
FIG. 15B is the XRPD pattern for Compound 2 as described in Example 14. The x-axis is 2Theta measured in degrees and the y-axis is intensity measured in counts.

Compound 2 was further characterized by eye, $^1$HNMR, $^{13}$CNMR, $^{19}$FNMR, MS, HPLC, and XRPD (FIG. 15B). Residual solvent was measured by GC. Water content was measured by Karl Fischer Titration, and the water content was only 0.70%. Data is summarized in Table 18.

TABLE 18

Summary of Additional Characterization Data of Compound 2

| Test | Result |
|---|---|
| Appearance | White Solid |
| NMR | $^1$HNMR peaks are listed in Example 4 |
| MS | MS(ESI + ve) [M + H]$^+$ = 582.3 - conforms to structure |
| HPLC | 99.8% by AUC at 254 nm (average of two preparations) |
| Residual Solvent by GC | Methanol - 57 ppm<br>Acetone - 752 ppm<br>Dichloromethane - 50 ppm<br>Ethyl Acetate - 176 ppm |
| Water Content | 0.70% |

Example 15. Solubility of Compound 1 and Compound 2

Compound 1 and Compound 2 were both tested for solubility in biorelevant test medias, including simulated gastric fluid (SGF), fasted-state simulated gastric fluid (FaSSIF), and fed-state gastric fluid (FeSSIF). Results for Compound 1 are shown in Table 19 and results for Compound 2 are shown in Table 20. Samples were stirred at room temperature (20-25° C.). Compound 2 was more than 40-fold more soluble than Compound 1 in water at 2 hours and more than 25-fold more soluble at 24 hours. In SGF conditions, Compound 2 had a solubility of 84.2 mg/mL at 24 hours compared to the solubility of 15.6 mg/mL of Compound 1 at the same time point. Compound 2 was also more soluble at 2 hours in the SGF conditions than Compound 1, and soluble enough to allow for testing even after 48 hours while testing at 48 hours was not done with Compound 1.

TABLE 19

Compound 1 solubility testing results

| Test Media | Solubility (in mg/mL) | | Appearance | Descriptive term |
|---|---|---|---|---|
| | 2 hours | 24 hours | | |
| Water | 1.5 | 2.5 | Clear Solution* | Slightly Soluble |
| SGF | 13.8 | 15.6 | Clear Solution with gum at the bottom | Sparingly Soluble |
| FaSSIF | 1.7 | 1.7 | Turbid | Slightly Soluble |
| FeSSIF | 2.8 | 2.9 | Turbid | Slightly Soluble |

*Sample appeared to be clear, yet a solubility of only 1.5 mg/mL was achieved. Upon further investigation, it was noted that a gummy film formed on the stir bar. The compound 1 active pharmaceutical ingredient formed a gummy ball in diluent (90% water/10% acetonitrile) during standard preparation which required a long sonication time to dissolve completely.

TABLE 20

Compound 2 solubility testing results

| Test Media | Solubility (in mg/mL salt base) | | | Appearance | Descriptive term |
|---|---|---|---|---|---|
| | 2 hours | 24 hours | 48 hours | | |
| Water | 65.3 | 68.0 | N/A | Turbid | Soluble |
| SGF | 89.0 | 84.2 | 81.3 | Turbid | Soluble |
| FaSSIF | 1.9 | 2.0 | N/A | Turbid | Slightly Soluble |
| FeSSIF | 3.3 | 3.4 | N/A | Turbid | Slightly Soluble |

Example 16. Chemical Stability of Compound 2

Compound 2 was tested for chemical stability at 25 and 40° C. over a 6 month time period by monitoring organic purity, water content, $^1$HNMR, DSC, and Ramen IR. The container closure system for the study was a combination medicinal valve bag with a pharmaceutical laminated film over the pouch and desiccant silica gel between the two layers. Compound 2 (1 g) was measured into each container. Bags were then stored at 25° C./60% RH (relative humidity) and 40° C./75% RH (relative humidity). Organic purity, water content, $^1$HNMR, DSC and Raman were measured at Time 0, Month 1, Month 2, Month 3 and Month 6.

The purity of Compound 2 was obtained using a Shimadzu LC-20AD system with a Waters XTerra Phenyl, 5 μm, 4.6×250 mm column with the following conditions: 1 mL/min flow rate, read at 254 nm, 35° C. column temperature, and 10 μL injection volume. The sample was dissolved in acetonitrile-water (90:10) (v/v). The gradient method is shown below.

| Time (min) | A % (ACN) | B % (water) |
|---|---|---|
| 0 | 90 | 10 |
| 20 | 20 | 80 |
| 20.1 | 90 | 10 |
| 30 | 90 | 10 |

The water content of Compound 2 (250 mg) was determined by a water titration apparatus using the Karl Fischer titration method.

Results are shown in Table 21 and Table 22. When Compound 2 was stored for 6 months at 25 and 40° C., the rate of degradation was minimal. At 3 months, Compound 2 was 99.75% percent pure at the 25° C. conditions and 99.58% pure at the 40° C. conditions. At 6 months, Compound 2 was still 99.74% pure at the 25° C. conditions and 99.30% pure at the 40° C. conditions. At 25° C., the percent of degradation product increased from 0.03% at Day 0 to 0.08% after 6 months. At 40° C., the percent of degradation product increased from 0.03% to 0.39%. Over the course of 6 months, the percent of water increased approximately 0.6% at 25° C. and increased approximately 0.7% at 40° C.

Characterization by $^1$HNMR, Raman, and DSC of Compound 2 at 1, 2, 3, and 6 months was the same as the characterization of Compound 2 on day 0 at both temperature conditions (Table 22), highlighting the long-term stability of Compound 2.

TABLE 21

Compound 2 rate of degradation over 6 months at 25 and 40° C.

| | Time Tested | Percent Water | Percent Purity | Percent of Degradation Product | Maximum Impurity Percent |
|---|---|---|---|---|---|
| 25° C. | Day 0 | 1.2 | 99.82 | 0.03 | 0.12 |
| | Month 1 | 1.9 | 99.77 | 0.04 | 0.12 |
| | Month 2 | 1.8 | 99.75 | 0.06 | 0.12 |
| | Month 3 | 1.8 | 99.75 | 0.06 | 0.12 |
| | Month 6 | 1.8 | 99.74 | 0.08 | 0.13 |
| 40° C. | Day 0 | 1.2 | 99.82 | 0.03 | 0.12 |
| | Month 1 | 2.0 | 99.71 | 0.09 | 0.12 |
| | Month 2 | 1.9 | 99.63 | 0.15 | 0.12 |
| | Month 3 | 1.9 | 99.58 | 0.20 | 0.12 |
| | Month 6 | 1.9 | 99.30 | 0.39 | 0.14 |

TABLE 22

Characterization of Compound 2 during degradation study

| | Time Tested | $^1$HNMR | Raman | DSC |
|---|---|---|---|---|
| 25° C. | Day 0 | Initial Test | Initial Test | Initial Test |
| | Month 1 | The same as Day 0 | The same as Day 0 | The same as Day 0 |
| | Month 2 | The same as Day 0 | The same as Day 0 | The same as Day 0 |
| | Month 3 | The same as Day 0 | The same as Day 0 | The same as Day 0 |
| | Month 6 | The same as Day 0 | The same as Day 0 | The same as Day 0 |
| 40° C. | Day 0 | Initial Test | Initial Test | Initial Test |
| | Month 1 | The same as Day 0 | The same as Day 0 | The same as Day 0 |
| | Month 2 | The same as Day 0 | The same as Day 0 | The same as Day 0 |
| | Month 3 | The same as Day 0 | The same as Day 0 | The same as Day 0 |
| | Month 6 | The same as Day 0 | The same as Day 0 | The same as Day 0 |

Additional chemical stability studies of Compound 2 were measured to determine the impurity and water levels. Three conditions were tested: accelerated stability (40±2° C./75±5% RH) over a 6-month time period, ambient stability (25±2° C./60±5% RH) over a 9-month period, and stability under refrigerator conditions (5±3° C.) over a 9-month time period. The results for accelerated stability, ambient stability, and refrigerator conditions are shown in Table 23, Table 24, and Table 25, respectively. Based on the results of these studies, Compound 2 is very chemically stable.

In the accelerated stability study (Table 23), at each time point (1$^{st}$ month, 3$^{rd}$ month, and 6$^{th}$ month) where Compound 2 was measured, the appearance of Compound 2 was always a white solid and the IR matched the reference standard. After six months, the total related substance 1 impurities was only 0.08% and there was no detection of related substance 2 and isomers.

TABLE 23

Accelerated Stability (40 ± 2° C./75 ± 5% RH) of Compound 2

| | | | | Testing time point | | | |
|---|---|---|---|---|---|---|---|
| | Items | | Specification | 0 month | 1$^{st}$ month | 3$^{rd}$ month | 6$^{th}$ month |
| | Appearance | | White or off-white solid | White solid | White solid | White solid | White solid |
| | IR | | correspond with reference standard | correspond with reference standard | / | correspond with reference standard | correspond with reference standard |
| | Water | | ≤2.0% | 0.45% | 0.21% | 0.36% | 0.41% |
| Related Substance 1 | Impurity A | | ≤0.15% | N.D. | N.D. | N.D. | N.D. |
| | Impurity B | | ≤0.15% | N.D. | N.D. | N.D. | N.D. |
| | Impurity F | | ≤0.15% | N.D. | N.D. | N.D. | 0.01% |
| | Impurity H | | ≤0.15% | N.D. | N.D. | N.D. | N.D. |
| | Any other single impurity | | ≤0.10% | 0.01% | 0.02% | 0.01% | 0.05% |
| | Total Impurities | | ≤0.2% | 0.01% | 0.02% | 0.02% | 0.08% |
| Related Substance 2 | Impurity G | | ≤0.15% | N.D. | N.D. | N.D. | N.D. |
| Isomer | Impurity C | | ≤0.15% | N.D. | / | N.D. | N.D. |
| | Impurity D | | ≤0.15% | N.D. | / | N.D. | N.D. |
| | Impurity E | | ≤0.15% | N.D. | / | N.D. | N.D. |
| | Assay | | 98.0%~102.0% | 98.8% | 101.5% | 99.6% | 99.5% |
| Microbial | TAMC | | <1000 cfu/g | <1 cfu/g | / | / | / |

TABLE 23-continued

Accelerated Stability (40 ± 2° C./75 ± 5% RH) of Compound 2

| | | | | Testing time point | | |
|---|---|---|---|---|---|---|
| Items | | Specification | 0 month | 1st month | 3rd month | 6th month |
| Testing | Mold and Yeast | <100 cfu/g | <1 cfu/g | / | / | / |
| | E.Coli | Not Detected | N.D. | / | / | / |

N.D.: Not Detected

In the ambient stability study where the appearance, IR, water and impurity levels were measured for nine months, the appearance of Compound 2 was always a white solid and the IR always corresponded with the reference sample. The results (Table 24) highlight how chemically stable Compound 2 is. After 9 months, the percentage of water in the sample was only 0.20% and the total related substance 1 impurities was only 0.02%. Similarly to the accelerated stability studies, related substance 2 and any isomers of Compound 2 were not detected.

TABLE 24

Ambient stability (25 ± 2° C./60 ± 5% RH) of Compound 2

| | | | | Testing time point | | | |
|---|---|---|---|---|---|---|---|
| Item | | Specification | 0 month | 1st month | 3rd month | 6th month | 9th month |
| Appearance | | White or off-white solid | White solid | White solid | White solid | White solid | Off-white solid |
| IR | | correspond with reference standard | correspond with reference standard | / | correspond with reference standard | correspond with reference standard | correspond with reference standard |
| Water | | ≤2.0% | 0.45% | 0.19% | 0.29% | 0.46% | 0.20% |
| Related Substance 1 | Impurity A | ≤0.15% | N.D. | N.D. | N.D. | N.D. | N.D. |
| | Impurity B | ≤0.15% | N.D. | N.D. | 0.03% | N.D. | N.D. |
| | Impurity F | ≤0.15% | N.D. | N.D. | 0.02% | 0.01% | N.D. |
| | Impurity H | ≤0.15% | N.D. | N.D. | N.D. | N.D. | N.D. |
| | Any other single impurity | ≤0.10% | 0.01% | 0.01% | 0.03% | 0.02% | 0.02% |
| | Total Impurities | ≤0.2% | 0.01% | 0.02% | 0.11% | 0.05% | 0.02% |
| Related Substance 2 | Impurity G | ≤0.15% | N.D. | N.D. | N.D. | N.D. | N.D. |
| Isomer | Impurity C | ≤0.15% | N.D. | / | N.D. | N.D. | N.D. |
| | Impurity D | ≤0.15% | N.D. | / | N.D. | N.D. | N.D. |
| | Impurity E | ≤0.15% | N.D. | / | N.D. | N.D. | N.D. |
| Assay | | 98.0%~102.0% | 98.8% | 101.1% | 99.6% | 99.7% | 100.9% |
| Microbial Testing | TAMC | ≤1000 cfu/g | ≤1 cfu/g | / | / | / | / |
| | Mold and Yeast | ≤100 cfu/g | ≤1 cfu/g | / | / | / | / |
| | E.Coli | Not Detected | N.D. | / | / | / | / |

N.D.: Not Detected

The results of measuring the stability under refrigerator conditions are shown in Table 25. The only impurities detected even after 9 months were those from related substance 1 and water. The water content after 9 months was 0.32% and the total impurities of related substance 1 were only 0.01% of the sample. Compound 2 is very chemically stable under refrigerator conditions.

TABLE 25

Stability under refrigerator conditions (5 ± 3° C.) of Compound 2

| | | | Testing time point | | | |
|---|---|---|---|---|---|---|
| Item | Specification | 0 month | 1st month | 3rd month | 6th month | 9th month |
| Appearance | White or off-white solid | White solid | White solid | White solid | White solid | Off-white solid |

TABLE 25-continued

Stability under refrigerator conditions (5 ± 3° C.) of Compound 2

| Item | | Specification | 0 month | 1st month | 3rd month | 6th month | 9th month |
|---|---|---|---|---|---|---|---|
| | IR | correspond with reference standard | correspond with reference standard | / | correspond with reference standard | correspond with reference standard | correspond with reference standard |
| | Water | ≤2.0% | 0.45% | 0.19% | 0.32% | 0.42% | 0.32% |
| Related Substance 1 | Impurity A | ≤0.15% | N.D. | N.D. | N.D. | N.D. | N.D. |
| | Impurity B | ≤0.15% | N.D. | N.D. | 0.01% | N.D. | N.D. |
| | Impurity F | ≤0.15% | N.D. | N.D. | N.D. | N.D. | N.D. |
| | Impurity H | ≤0.15% | N.D. | N.D. | N.D. | N.D. | N.D. |
| | Any other single impurity | ≤0.10% | 0.01% | 0.01% | 0.01% | 0.01% | 0.01% |
| | Total Impurities | ≤0.2% | 0.01% | 0.01% | 0.03% | 0.03% | 0.01% |
| Related Substance 2 | Impurity G | ≤0.15% | N.D. | N.D. | N.D. | N.D. | N.D. |
| Isomer | Impurity C | ≤0.15% | N.D. | / | N.D. | N.D. | N.D. |
| | Impurity D | ≤0.15% | N.D. | / | N.D. | N.D. | N.D. |
| | Impurity E | ≤0.15% | N.D. | / | N.D. | N.D. | N.D. |
| | Assay | 98.0%~102.0% | 98.8% | 101.1% | 100.2% | 98.6% | 101.4% |
| Microbial Testing | TAMC | ≤1000 cfu/g | ≤1 cfu/g | / | / | / | / |
| | Mold and Yeast | ≤100 cfu/g | ≤1 cfu/g | / | / | / | / |
| | E.Coli | Not Detected | N.D. | / | / | / | / |

N.D.: Not Detected

Example 17. Plasma Levels of Metabolites Following Single Oral Doses of Compound 2

A single oral dose of Compound 2 was administered to rats, dogs, and monkeys, and the plasma levels of certain metabolites shown in Scheme 1 were measured.

The conversion of Compound 2 to Compound 1 and metabolite 1-7 are shown in Table 26 and the results for metabolite 1-8 and metabolite 1-2 are shown in Table 27. In rats, low levels of Compound 1 exposure were observed, but high levels of metabolite 1-7, the nucleoside metabolite of the active triphosphate (metabolite 1-6), were observed. In monkeys, roughly dose-proportional exposures of Compound 1 were measured. In dogs, supra-proportional Compound 1 exposures, indicative of first-pass metabolic clearance in the liver, were measured. Throughout the study, significantly more vomiting in dogs (5/5 in high dose group) than in monkeys (1/5 in high dose group) was observed.

TABLE 26

Plasma levels of Compound 1 and metabolite 1-7 after single oral doses of Compound 2

| | | Compound 1 | | | Metabolite 1-7 | |
|---|---|---|---|---|---|---|
| Species | Dose* (mg/kg) | $C_{max}$ (ng/mL) | $T_{max}$ (hr) | $AUC_{0-last}$ (hr*ng/mL) | $C_{max}$ (ng/mL) | $AUC_{0-last}$ (hr*ng/mL) |
| Rat[a] | 500 | 70.5 | 0.25 | 60.9 | 748 | 12000 |
| Dog[b] | 30 | 1530 | 0.25-1 | 1300 | 783 | 9270 |
| | 100 | 8120 | 0.5-1 | 10200 | 2030 | 24200 |
| | 300 | 21300 | 204 | 44300 | 4260 | 60800 |
| Monkey[b] | 30 | 63.5 | 0.5-2 | 176 | 42.5 | 1620 |
| | 100 | 783 | 1-2 | 1100 | 131 | 3030 |
| | 300 | 501 | 204 | 1600 | 93.6 | 3660 |

3 males per dose per species;
*dose formulations:
[a]0.5% CMC, 0.5% Tween 80 in water;
[b]powder in capsules

TABLE 27

Plasma levels of metabolites 1-8 and 1-2
after single oral dose of Compound 2

| | | Metabolite 1-8 | | Metabolite 1-2 | |
|---|---|---|---|---|---|
| Species | Dose* (mg/kg) | $C_{max}$ (ng/ml) | $AUC_{0\text{-}last}$ (hr*ng/ml) | $C_{max}$ (ng/ml) | $AUC_{0\text{-}last}$ (hr*ng/ml) |
| Rat[a] | 500 | 5060 | 35100 | 9650 | 20300 |
| Dog[b] | 30 | 291 | 905 | 196 | 610 |
| | 100 | 1230 | 4370 | 886 | 2830 |
| | 300 | 5380 | 35300 | 2380 | 8710 |
| Monkey[b] | 30 | 209 | 5690 | 300 | 1730 |
| | 100 | 406 | 12300 | 1350 | 8160 |
| | 300 | 518 | 16800 | 1420 | 11400 |

Figure 16A:
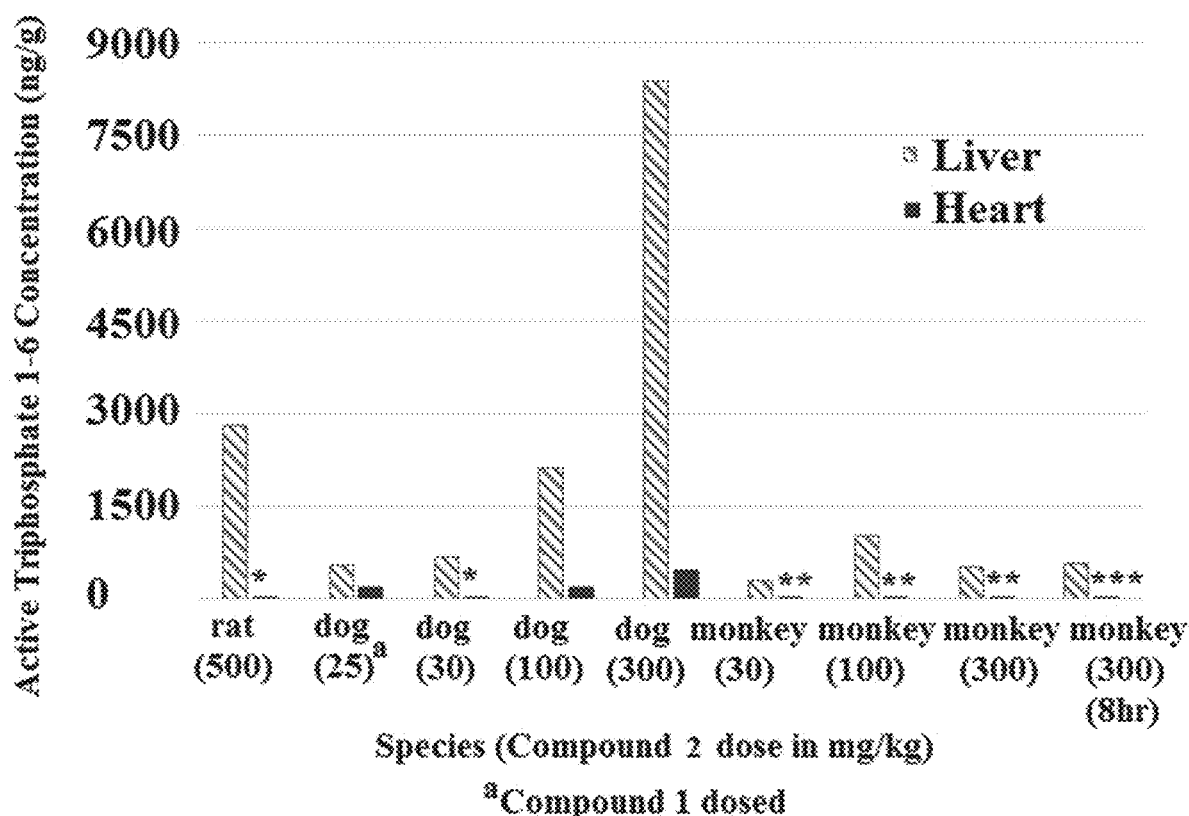
FIG. 16A is a graph of the active TP (metabolite 1-6) concentration levels in the livers and hearts of rats, dogs, and monkeys (Example 18). The x-axis is the dosage measured in mg/kg for each species and the y-axis is the active TP concentration measured in ng/g.

3 males per dose per species; *dose formulations: [a]0.5% CMC, 0.5% Tween 80 in water; [b]powder in capsules Example 18. Tissue Exposure of Active Triphosphate Following Compound 2 Oral Dose Heart and liver tissue levels of the active triphosphate (TP) of Compound 2 (metabolite 1-6) were measured 4 hours after oral doses of Compound 2. Samples of liver and heart were obtained at 4 hours after a single dose of Compound 2, flash-frozen, homogenized and analyzed by LC-MS/MS for intracellular levels of the active TP. Tissue levels were measured in rats, dogs, and monkeys as shown in FIG. 16A. High levels of the active TP were measured in the liver of all species tested. Relatively low levels of the active TP were measured in the hearts of dogs due to saturation of first-pass hepatic metabolism, and unquantifiable levels of TP were measured in rat and monkey hearts, indicative of liver-specific formation of the active TP. While not shown, compared to Compound 1 dosing, Compound 2 dosing improved TP distribution.

Example 19. Pharmacological Comparison of Compound 1 and Compound 2 in Dogs

A head-to-head comparison of dogs dosed with Compound 1 and Compound 2 was conducted. The study measured plasma levels of Compound 1 and metabolite 1-7 (from Scheme 1) out to 4 hours after dosing with Compound 1 (25 mg/kg) and Compound 2 (30 mg/kg) (Table 28), and the $AUC_{(0\text{-}4hr)}$ of metabolite 1-7 was twice as great with Compound 2 compared to Compound 1. Dose-normalized exposures to Compound 1 and Compound 2 are shown in Table 28. Values for $AUC_{(0\text{-}4hr)}$ for Compound 1, metabolite 1-7, and the sum of Compound 1+metabolite 1-7 were greater after dosing with Compound 2.

TABLE 28

Comparison of Plasma Levels following
dosing with Compound 1 and Compound 2

| | Mean Dose-normalized $AUC_{(0\text{-}4\ hr)}{}^{a}$ (µM*hr) for: | | |
|---|---|---|---|
| Dosed Compound | Compound 1 | Metabolite 1-7 | Compound 1 + Metabolite 1-7 |
| Compound 1 (25 mg/kg) | 0.2 | 1.9 | 2.1 |
| Compound 2 (30 mg/kg) | 1.0 | 4.1 | 5.1 |

[a]$AUC_{(0\text{-}4\ hr)}$ values normalized to a dose of 25 mg/kg

Liver/heart ratio triphosphate concentrations indicate that dosing with Compound 2, as compared to Compound 1, increases the selective delivery of the triphosphate to the liver, as shown in Table 29. The $AUC_{(0\text{-}4hr)}$ of the active guanine metabolite (1-6) after administration of Compound 1 measured in the heart was 174 µM*hr, while the $AUC_{(0\text{-}4hr)}$ of the active guanine metabolite (1-6) after administration of Compound 2 measured in the heart was 28 µM*hr. The liver/heart ratio for Compound 2 was 20 compared to a liver/heart ratio of 3.1 for Compound 1.

TABLE 29

Comparison of Liver and Heart Exposure following
dosing with Compound 1 and Compound 2

| | Mean Dose-normalized $AUC_{(0\text{-}4\ hr)}{}^{a}$ (µM*hr) for: | | |
|---|---|---|---|
| Dosed Compound | Liver | Heart | Liver/Heart |
| Compound 2 | 565 | 28[b] | 20 |
| Compound 1 | 537 | 174 | 3.1 |

Figure 16B:
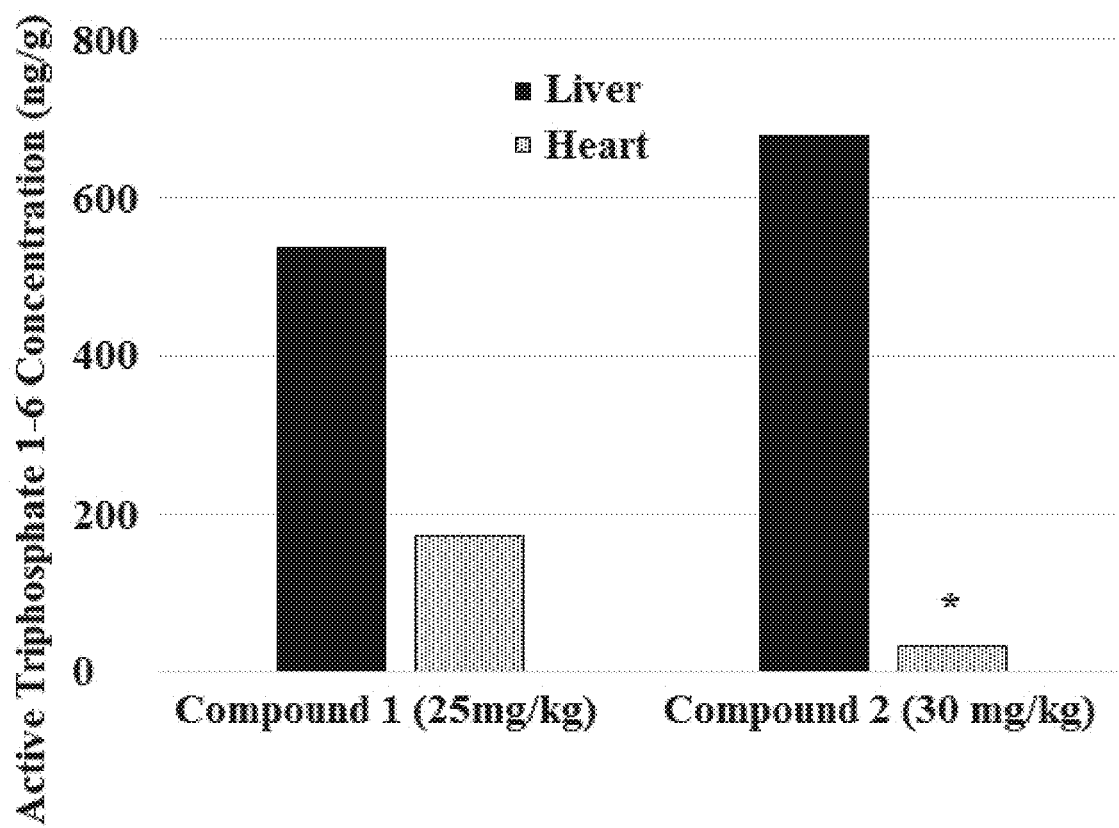
FIG. 16B is a graph of the active TP (metabolite 1-6) concentration levels in the liver and heart of dogs (n=2) measured 4 hours after a single oral dose of Compound 1 or Compound 2 (Example 19). The x-axis is the dosage of each compound measured in mg/kg and the y-axis is the active TP concentration measured in ng/g.

[a]Active TP concentrations (1-6; Scheme 1) normalized to a dose of 25 mg/kg
[b]Extrapolated below the lower limit of quantitation of the calibration curve The effect of increased selectivity for the liver over the heart when Compound 2 was administered compared to Compound 1 is also shown in FIG. 16B. The heart and liver tissue levels of the active triphosphate following a dosage of Compound 2 (30 mg/kg) were compared to the tissue levels of the active triphosphate following a dosage of Compound 1 (25 mg/kg). The concentration of the active TP was higher in the liver than the heart for both Compound 1 and Compound 2, but the active TP was more selective for the liver over the heart when Compound 2 was dosed compared to Compound 1.

Example 20. Plasma Profiles of Compound 2 Metabolites in Rats and Monkeys

Figure 17:
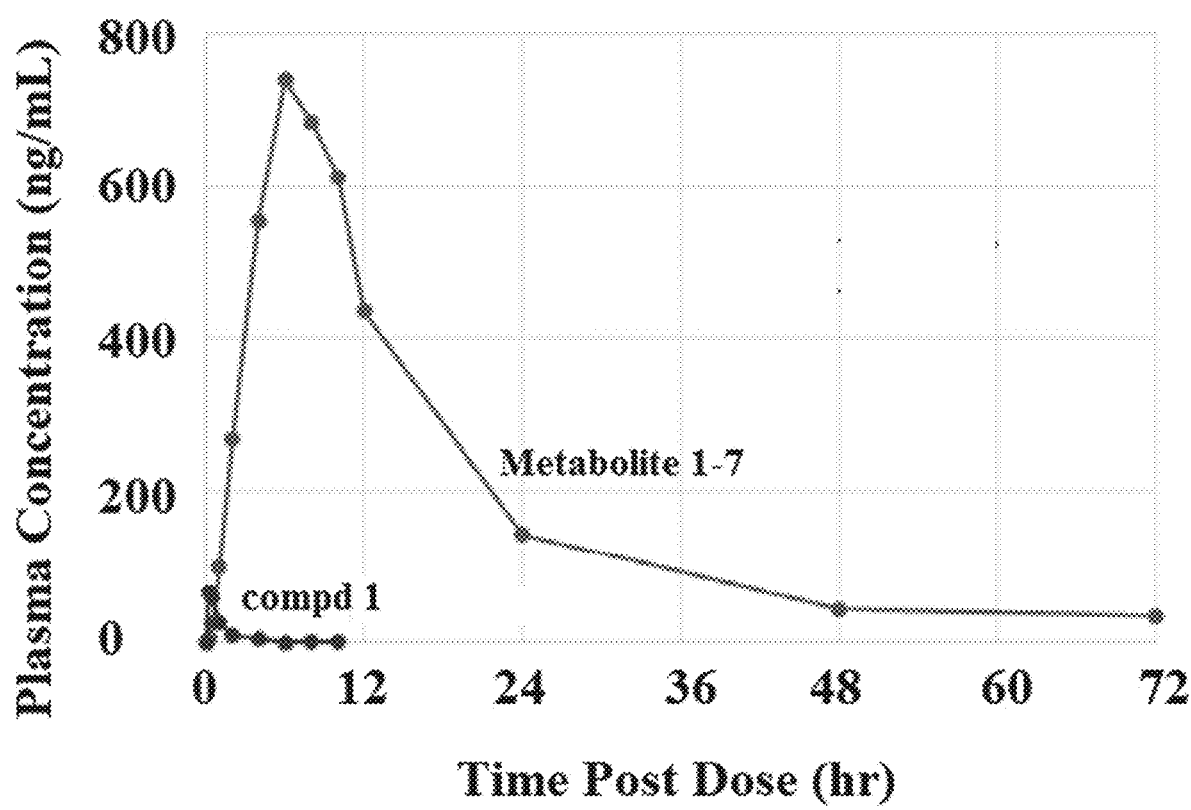
FIG. 17 is the plasma profile of Compound 1 and metabolite 1-7 in rats given a single 500 mg/kg oral dose of Compound 2 (Example 20) measured 72 hours post-dose. The x-axis is time measured in hours and the y-axis is plasma concentration measured in ng/mL.
Figure 18:
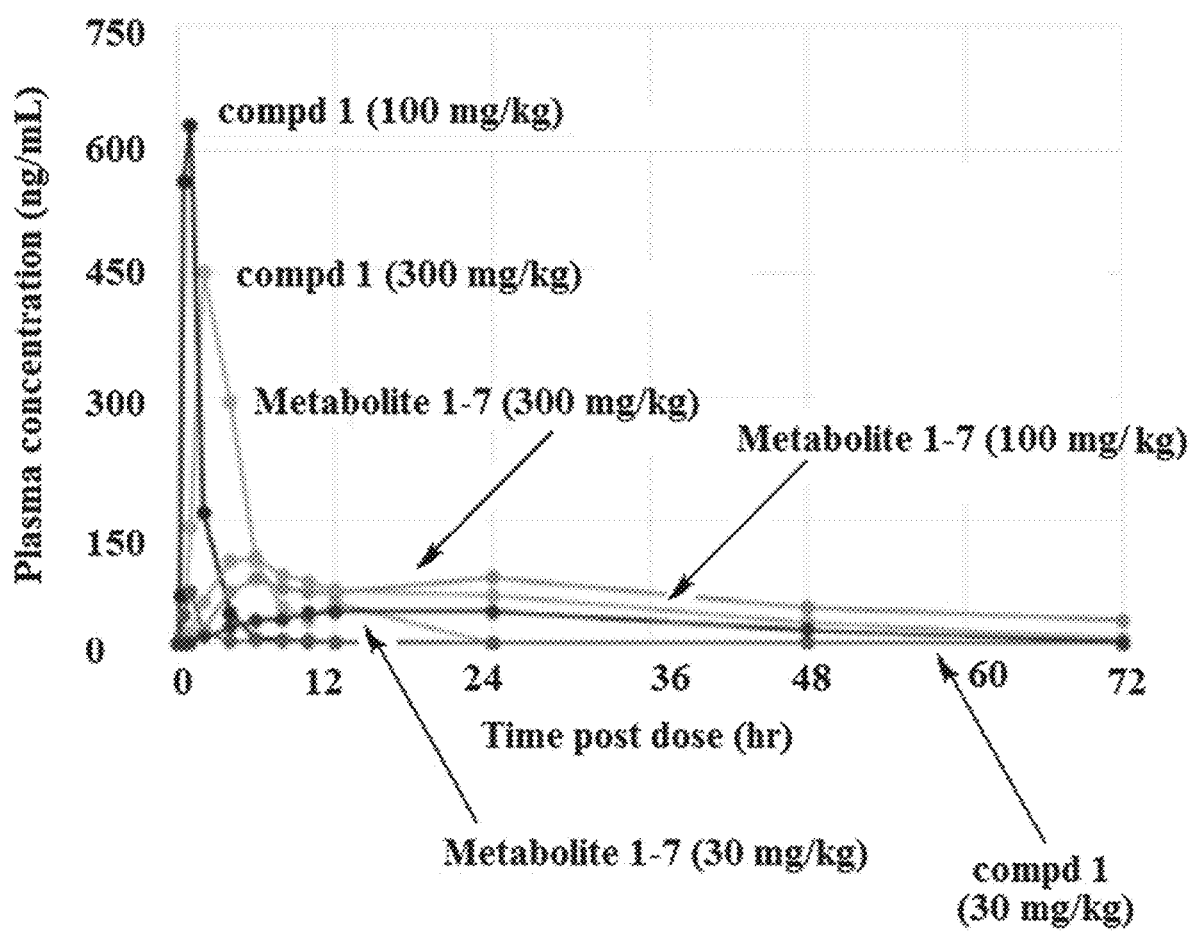
FIG. 18 is the plasma profile of Compound 1 and metabolite 1-7 in monkeys given single oral doses of 30 mg, 100 mg, or 300 mg of Compound 2 (Example 20) measured 72 hours post-dose. The x-axis is time measured in hours and the y-axis is plasma concentration measured in ng/mL.

Male Sprague-Dawley rats and cynomolgus monkeys (3 animals per dose group) were given single oral doses of Compound 2. Aliquots of plasma prepared from blood samples treated with Dichlorvos were analyzed by LC-MS/MS for concentrations of Compound 1 and metabolite 1-7 (the nucleoside metabolite of the active triphosphate of Compound 2 shown in Scheme 1), and pharmacokinetic parameters were determined using WinNonlin. The results for a single 500 mg/kg dose in rats is shown in FIG. 17 and the results for a single 30, 100, or 300 mg/kg dose in monkeys is shown in FIG. 18. The results are also summarized in Table 30.

High plasma levels of metabolite 1-7, the nucleoside metabolite of the active triphosphate (TP) of Compound 2, are indicative of formation of high levels of the TP, even in rats where very low plasma levels of parent nucleotide prodrug are observed due to the short half-life of Compound in rat blood (<2 min). Persistent plasma levels of metabolite 1-7 reflect the long half-life of the TP.

In monkeys, plasma exposures (AUC) of Compound 1 were roughly dose-proportional, while metabolite 1-7 exposures were somewhat less than dose-proportional, although AUC values for both parent drug and the nucleoside metabolite of the active TP continue to increase up to the highest dose tested (300 mg/kg).

Oral administration of Compound 2 in rats and monkeys produced high and dose-dependent plasma exposures to metabolite 1-7 (the nucleoside metabolite of the intracellular active triphosphate of Compound 2); metabolite 1-7 exposures continued to increase up to the highest dose tested, reflecting substantial formation of the active TP in these species.

TABLE 30

Plasma levels of Compounds 1 and 1-7 after single oral dose of Compound 2

| Species | | Rat[a] | Monkey[b] | | |
|---|---|---|---|---|---|
| Dose (mg/kg) | | 500 | 30 | 100 | 300 |
| Compound 1 | $C_{max}$ (ng/mL) | 60.8 | 63.5 | 783 | 501 |
| | $T_{max}$ (hr) | 0.25 | 0.5-2 | 1-2 | 204 |
| | $AUC_{0-last}$ (hr*ng/mL) | 78.2 | 176 | 1100 | 1600 |
| Metabolite 1-7 | $C_{max}$ (ng/mL) | 541 | 42.5 | 131 | 93.6 |
| | $AUC_{0-last}$ (hr*ng/mL) | 9640 | 1620 | 3030 | 3660 |
| | $T_{max}$ (hr) | 6-8 | 12-24 | 4 | 4-24 |
| | $T_{1/2}$ (hr) | 15.3 | 11.5 | 15.0 | 18.8 | dose formulations: [a] 0.5% CMC, 0.5% Tween 80 in water; [b] powder in capsules

Example 21. The Effect of the Active Triphosphate of Compound 1 and Compound 2 on Mitochondrial Integrity The relative efficiency of incorporation of the active triphosphate (TP) of Compound 1 and Compound 2, metabolite 1-6 (Scheme 1), by human mitochondrial RNA polymerase was compared to the relative efficiency of the active TP of sofosbuvir and the active TP of INX-189. Compound 1 and Compound 2 are not likely to affect mitochondrial integrity since their active triphosphate is poorly incorporated by human mitochondrial RNA polymerase with an efficiency similar to that of the triphosphate of sofosbuvir; the relative efficiency of incorporation of the triphosphate of INX-189 was up to 55-fold greater. Results are shown in Table 31. The incorporation of these analogs by human mitochondrial RNA-dependent RNA polymerase (POLRMT) were determined according to Arnold et al. (Sensitivity of Mitochondrial Transcription and Resistance of RNA Polymerase II Dependent Nuclear Transcription to Antiviral Ribonucleotides. *PLoS Pathog.*, 2012, 8, e1003030).

TABLE 31

Kinetic Parameters for Nucleotide Analogs Evaluated with Human Mitochondrial RNA Polymerase

| Nucleotide Analog | $K_{pol}$ ($s^{-1}$) | $K_{d,app}$ ($\mu M$) | $K_{pol}/K_{d,app}$ ($\mu M^{-1} s^{-1}$) | Relative Efficiency* |
|---|---|---|---|---|
| 2'-deoxy-2'-F-2'-C-methyl UTP (active TP of sofosbuvir) | 0.00034 ± 0.00005 | 590 ± 250 | $5.8 \times 10^{-7}$ ± $2.6 \times 10^{-7}$ | $1.0 \times 10^{-6}$ |
| 2'-C-methyl GTP (active TP of INX-189) | 0.051 ± 0.002 | 240 ± 26 | $2.1 \times 10^{-4}$ ± $0.2 \times 10^{-4}$ | $5.5 \times 10^{-5}$ |
| Active TP of Compound 1 and Compound 2 (metabolite 1-6) | 0.0017 ± 0.0002 | 204 ± 94 | $8.3 \times 10^{-6}$ ± $4.0 \times 10^{-6}$ | $2.2 \times 10^{-6}$ |

*Relative efficiency = $(K_{pol}/K_{d,app})_{analog\ nucleotide}/(K_{pol}/K_{d,app})_{natural\ nucleotide}$

Example 22. Activity of Compound 1 Against Replicons Containing the NS5B Sequence A panel of replicons containing the NS5B sequences from various HCV genotypes derived from 6 laboratory reference strains (GT1a, 1b, 2a, 3a, 4a and 5a) (FIG. 19) and from 8 HCV patient plasma samples (GT1a, 1b, 2a, 2b, 3a-1, 3a-2, 4a and 4d) (FIG. 20) were used to determine the potency of Compound 1 and sofosbuvir.

Figure 19:
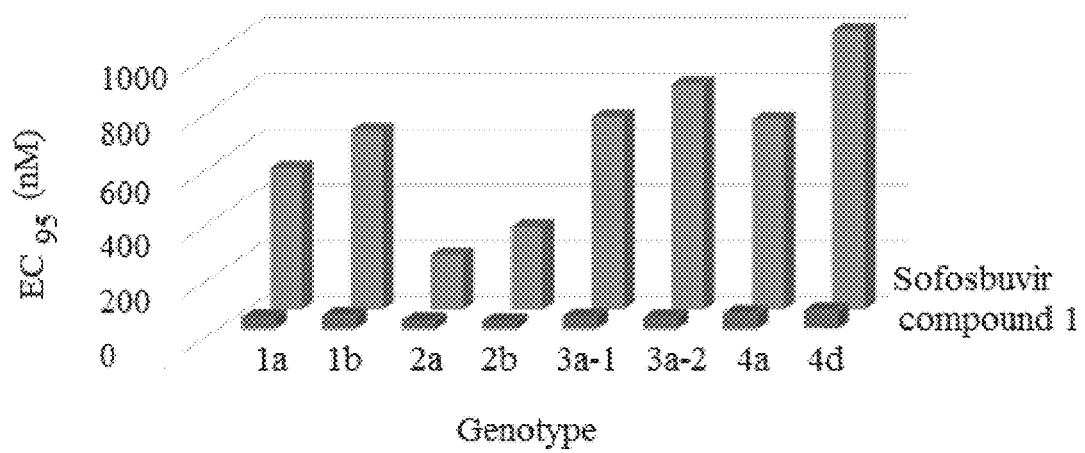
FIG. 19 is a graph of $EC_{95}$ measured in nM of sofosbuvir and Compound 1 against HCV clinical isolates. $EC_{95}$ values for Compound 1 are 7-33 times lower than sofosbuvir (Example 22). The x-axis is labeled with the genotype and the y-axis is $EC_{95}$ measured in nM.
Figure 20:
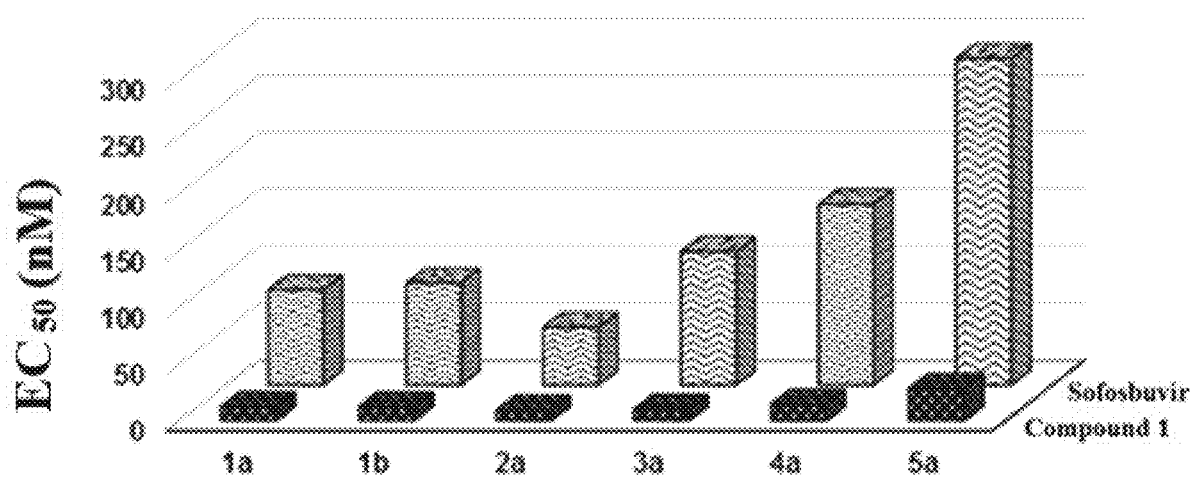
FIG. 20 is a graph of $EC_{50}$ measured in nM of sofosbuvir and Compound 1 against laboratory strains of HCV Genotypes 1a, 1b, 2a, 3a, 4a, and 5a. Compound 1 is approximately 6-11 times more potent than sofosbuvir in Genotypes 1-5 (Example 22). The x-axis is labeled with the genotype and the y-axis is $EC_{50}$ measured in nM.

Compound 1 was more potent than sofosbuvir against clinical and laboratory strains of HCV. Compound 1 showed potent pan-genotypic antiviral activity in vitro against wild-type clinical isolates with $EC_{95}$<80 nM, which is 4- to 14-fold more potent than sofosbuvir. As shown in FIG. 20, $EC_{95}$ values for Compound 1 were 7-33 times lower than sofosbuvir against clinical isolates of all HCV genotypes tested. $EC_{50}$ values for Compound 1 were 6-11 times lower than sofosbuvir against laboratory strains of HCV Genotypes 1-5 (FIG. 19).

Example 23. Single Ascending Dose (SAD) Study of Compound 2 in Healthy Volunteers (Part A) and GT1-HCV Infected Patients (Part B)

Compound 2 was tested in a single ascending dose (SAD) study to measure its safety, tolerability, and pharmacokinetic in healthy subjects (Part A). Part A was a randomized, double-blind, placebo-controlled SAD study. Healthy subjects in Part A received a single dose of Compound 2 or placebo in the fasting state. Subjects were confined to the clinic from Day −1 to Day 6.

Dosing in each cohort was staggered such that 2 subjects (1 active:1 placebo) were evaluated for 48 hours after dosing before the remainder of the cohort was dosed. Each cohort received Compound 2 in ascending order. Dosing of sequential cohorts occurred based on review of available safety data (through Day 5) and plasma pharmacokinetic data (through 24 h) of the prior cohort.

Dose escalation proceeded following satisfactory review of these data. As pharmacokinetic and safety data emerged from prior cohorts, doses evaluated in Cohorts 3a-4a were adjusted by increments no more than 100 mg. The total maximum dose evaluated in Part A did not exceed 800 mg. The dosing regimen for Part A is shown in Table 32.

TABLE 32

Dosing Regimen for Compound 2 Administration Part A of Study

| Cohort | Population | N (active:placebo) | Compound 2 (Compound 1)* |
|---|---|---|---|
| 1a | Healthy | 6:2 | 50 (45) mg × 1 day |
| 2a | Healthy | 6:2 | 100 (90) mg × 1 day |
| 3a | Healthy | 6:2 | 200 (180) mg × 1 day |
| 4a | Healthy | 6:2 | 400 (360) mg × 1 day |

*Clinical doses are expressed in terms of Compound 2, with the approximate Compound 1 base equivalent in parenthesis Healthy volunteers in the Part A portion of the study were male and female subjects between the ages of 18 and 65. Active and placebo recipients were pooled within each Part A cohort to preserve the study blind.

Compound 2 was also tested in a single ascending dose (SAD) study to measure its safety, tolerability, pharmacokinetic, and antiviral activity in GT1-HCV infected patients (Part B). Subjects in Part B received a single dose of Compound 2 in the fasting state. Patients were confined to the clinic from Day −1 to Day 6.

Part B was initiated after the safety (through Day 5) and plasma pharmacokinetic (through 24 h) data review from Cohort 3a in Part A. Available safety data (through Day 5) and pharmacokinetic data (through 24 h) was reviewed for the first cohort in Part B (Cohort 1b) before enrolling subsequent Part B cohorts. Subsequent Part B cohorts were only dosed following review of available safety and pharmacokinetic data from the respective doses in Part A as well as available safety (through Day 5) from the prior Part B cohorts.

Dose escalation up to 600 mg in HCV-infected patients proceeded following satisfactory review of these data. The dosing regimen for Part B is shown in Table 33.

TABLE 33

Dosing Regimen for Compound 2 in Part B of Study

| Cohort | Population | N (active) | Compound 2 (Compound 1)* |
|---|---|---|---|
| 1b | GT1 HCV-Infected | 3 | 100 (90) mg × 1 day |
| 2b | GT1 HCV-Infected | 3 | 300 (270) mg × 1 day |
| 3b | GT1 HCV-Infected | 3 | 400 (360) mg × 1 day |
| 4b | GT1 HCV-Infected | 3 | 600 (540) mg × 1 day |

*Clinical doses are expressed in terms of Compound 2, with the approximate Compound 1 base equivalent in parenthesis.

Patients infected with HCV were treatment-naïve, non-cirrhotic GT1-infected subjects with a viral load of ≥5 $\log_{10}$ IU/mL.

No serious adverse events were recorded and no premature discontinuations were required in either Part A or Part B. All adverse effects were mild to moderate in intensity and no dose-related patterns, including laboratory parameters, vital signs, and ECGs were evident.

Example 24. Results of the Single Ascending Dose (SAD) Study of Compound 2

Pharmacokinetic of Compound 1 and nucleoside metabolite 1-7 were measured following the single dose of Compound 2. The $C_{24}$ trough plasma concentrations ($C_{24h}$) of metabolite 1-7 in HCV-infected patients following a 600 mg dose of Compound 2 was 25.8 ng/mL, which is more than double the plasma concentration dose following a 300 mg dose of Compound 2. Metabolite 1-7 (shown in Scheme 1) can only be generated via dephosphorylation of the intracellular phosphate metabolite 1-4, metabolite 1-5, and metabolite 1-6, which is the active species. Therefore, metabolite 1-7 can be considered a surrogate of the active species. The pharmacokinetic data for all cohorts is shown in Table 34 and Table 35. Values are reported as mean±SD, except for $T_{max}$ where median (range) is reported. Pharmacokinetic parameters were comparable in healthy and HCV-infected patients.

TABLE 34

Human Pharmacokinetic of Compound 1 and Metabolite 1-7 after Administration of a single dose of Compound 2 in Healthy Volunteers

| | Dose (mg) | $C_{max}$ (ng/mL) | $T_{max}$ (h) | $AUC_{tot}$ (ng*h/mL) | $T_{1/2}$ (h) | $C_{24h}$ (ng/mL) |
|---|---|---|---|---|---|---|
| | | | Part A, Healthy Subjects | | | |
| Compd 1 | 50 | 46.4 ± 17.6 | 0.5 (0.5-0.5) | 36.4 ± 12.3 | 0.32 ± 0.02 | — |
| | 100 | 156 ± 96.3 | 0.5 (0.5-1.0) | 167 ± 110 | 0.53 ± 0.24 | — |
| | 200 | 818 ± 443 | 0.5 (0.5-3.0) | 656 ± 255 | 0.71 ± 0.16 | — |
| | 400 | 1194 ± 401 | 0.5 (0.5-1.0) | 1108 ± 326 | 0.86 ± 0.15 | — |
| Metabolite 1-7 | 50 | 27.9 ± 5.62 | 3.5 (3.0-4.0) | 285 ± 69.4 | 7.07 ± 4.59 | 2.28 ± 0.95 |
| | 100 | 56.6 ± 14.0 | 4.0 (3.0-6.0) | 663 ± 242 | 17.7 ± 14.7 | 4.45 ± 1.87 |
| | 200 | 111 ± 38.8 | 5.0 (3.0-6.0) | 1524 ± 497 | 15.9 ± 7.95 | 13.7 ± 5.09 |
| | 400 | 153 ± 49.4 | 6.0 (4.0-8.0) | 2342 ± 598 | 15.6 ± 6.37 | 23.5 ± 6.31 |

*Based on 24-hr profile.

TABLE 35

Human Pharmacokinetic of Compound 1 and Metabolite 1-7 after Administration of Compound 2 in GT1-HCV Infected Patients

| | Dose (mg) | $C_{max}$ (ng/mL) | $T_{max}$ (h) | $AUC_{tot}$ (ng*h/mL) | $T_{1/2}$ (h) | $C_{24h}$ (ng/mL) |
|---|---|---|---|---|---|---|
| Compd 1 | 100 | 212 ± 32.0 | 0.5 (0.5-1.0) | 179 ± 54.4 | 0.54 ± 0.12 | — |
| | 300 | 871 ± 590 | 0.5 (0.5-1.0) | 818 ± 475 | 0.64 ± 0.20 | — |
| | 300 | 2277 ± 893 | 0.5 (0.5-1.0) | 1856 ± 1025 | 0.84 ± 0.18 | — |
| | 400 | 2675 ± 2114 | 1.0 (1.0-2.0) | 2408 ± 1013 | 0.86 ± 0.18 | — |
| | 600 | 3543 ± 1649 | 1.0 (0.5-1.0) | 4132 ± 1127 | 0.70 ± 0.13 | — |
| Metabolite 1-7 | 100 | 50.2 ± 15.4 | 6.0 (4.0-6.0) | 538 ± 103* | 8.4 ± 4.3* | 3.60 ± 0.40 |
| | 300 | 96.9 ± 38.9 | 6.0 (3.0-6.0) | 1131 ± 273* | 8.1 ± 2.4* | 10.9 ± 3.51 |
| | 300 | 123 ± 16.6 | 4.0 (3.0-6.0) | 1420 ± 221 | — | 18.0 ± 8.83 |
| | 400 | 160 ± 36.7 | 4.0 (4.0-4.0) | 2132 ± 120 | 11.6 ± 1.21 | 22.5 ± 3.29 |
| | 600 | 198 ± 19.3 | 4.0 (4.0-6.0) | 2176 ± 116 | — | 25.8 ± 4.08 |

*Based on 24-hr profile.

Figure 21:
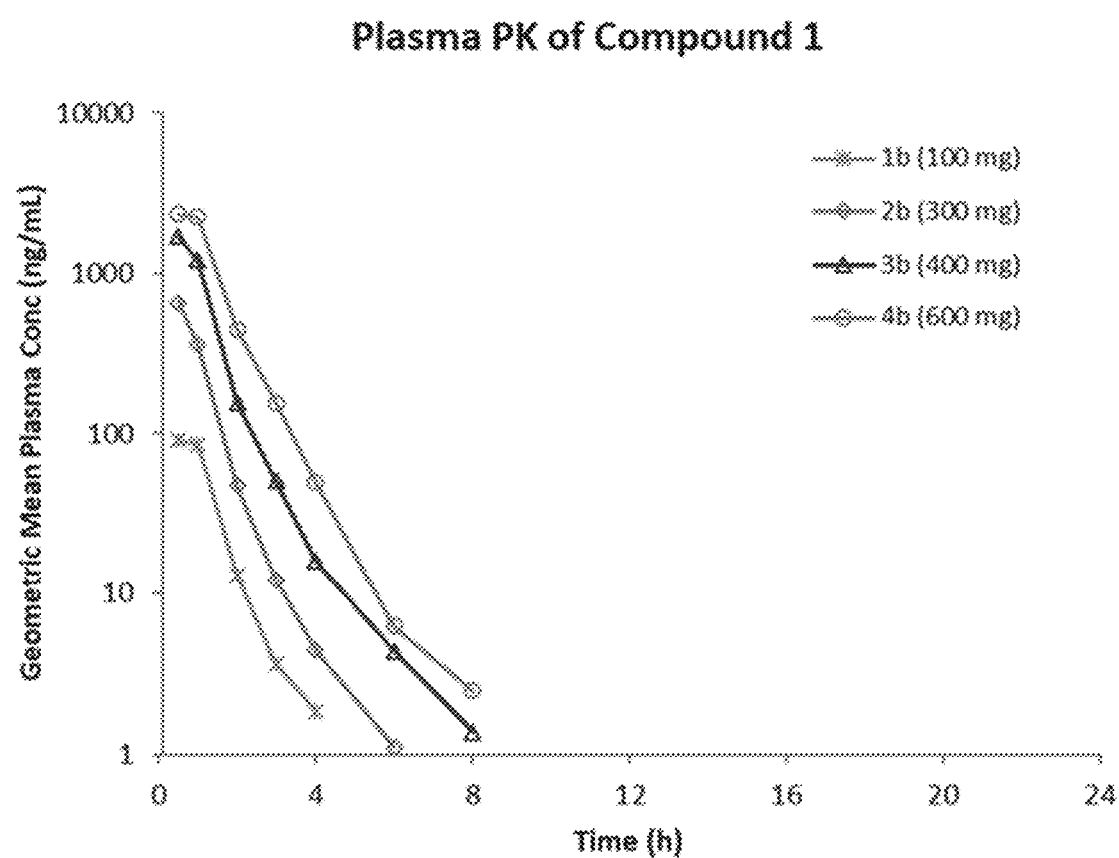
FIG. 21 is a graph of the mean plasma concentration-time profile of Compound 1 following the administration of a single dose of Compound 2 in all cohorts of Part B of the study as described in Example 24. Compound 1 was quickly absorbed and rapidly metabolized within approximately 8 hours in all cohorts from Part B. The x-axis is the time measured in hours and the y-axis is the geometric mean plasma concentration measured in ng/mL.
Figure 22:
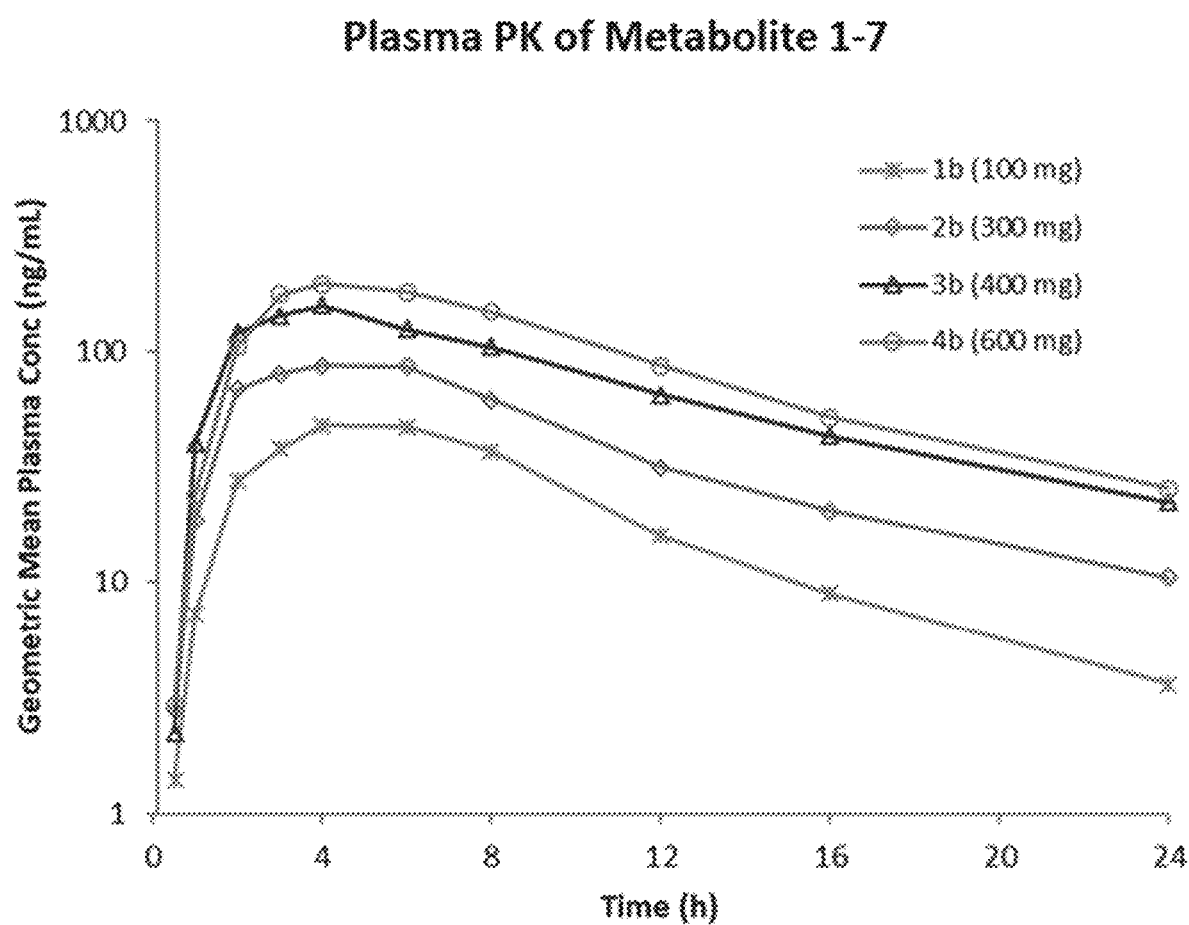
FIG. 22 is a graph of the mean plasma concentration-time profile of metabolite 1-7 following the administration of a single dose of Compound 2 in all cohorts of Part B of the study as described in Example 24. Metabolite 1-7 exhibited sustained plasma concentration in all cohorts from Part B. The x-axis is the time measured in hours and the y-axis is the geometric mean plasma concentration measured in ng/mL.
Figure 23A:
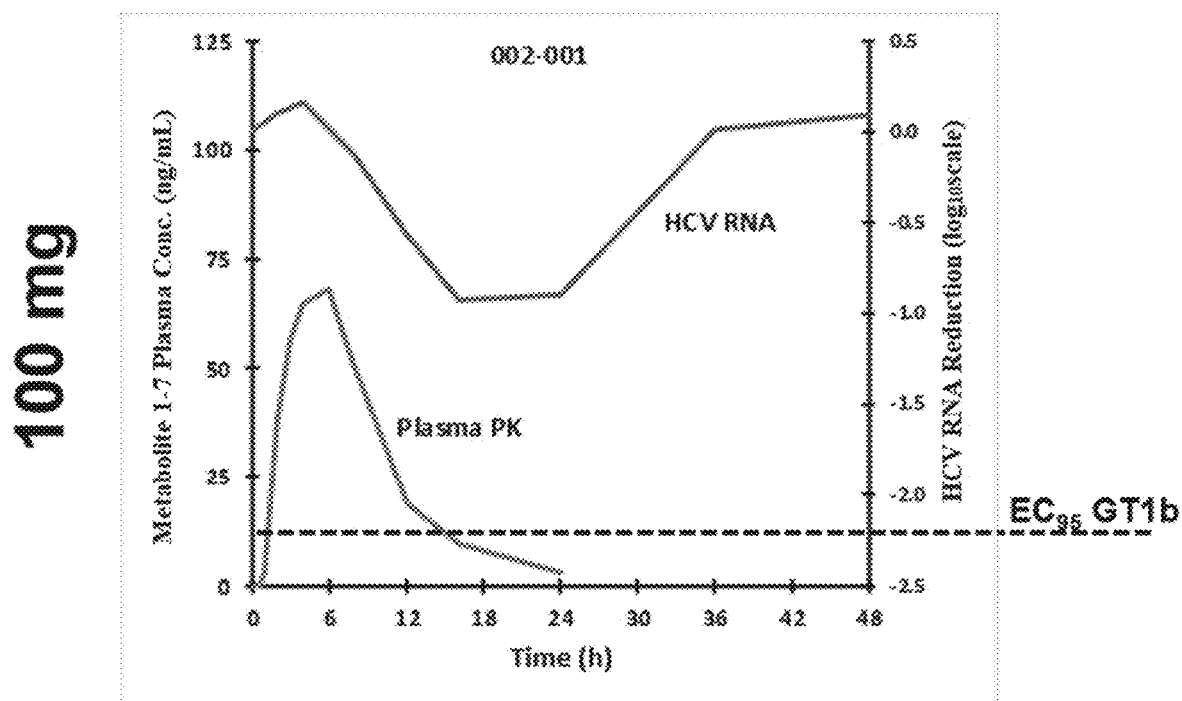
FIG. 23A is an individual pharmacokinetic/pharmacodynamic analysis of a subject enrolled in the 1b cohort as described in Example 24. The graph shows plasma metabolite 1-7 exposure and HCV RNA reduction levels. The dashed line represents the minimum concentration of metabolite 1-7 required to sustain a viral response greater than the $EC_{95}$ value against GT1b. The x-axis is time measured in hours. The left y-axis is metabolite 1-7 plasma concentration measured in ng/mL and the right y-axis is the HCV RNA reduction measured in $\log_{10}$ IU/mL.
Figure 23B:
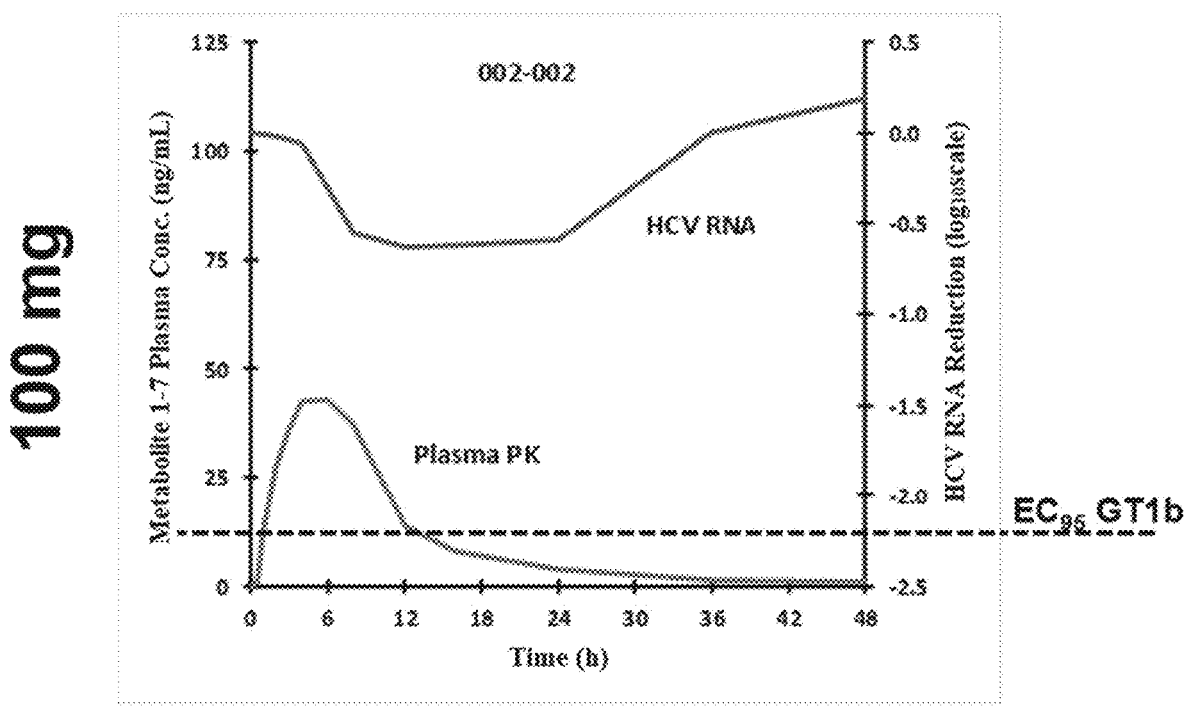
FIG. 23B is an individual pharmacokinetic/pharmacodynamic analysis of a subject enrolled in the 1b cohort as described in Example 24. The graph shows plasma metabolite 1-7 exposure and HCV RNA reduction levels. The dashed line represents the minimum concentration of metabolite 1-7 required to sustain a viral response greater than the $EC_{95}$ value against GT1b. The x-axis is time measured in hours. The left y-axis is metabolite 1-7 plasma concentration measured in ng/mL and the right y-axis is the HCV RNA reduction measured in $\log_{10}$ IU/mL.
Figure 23C:
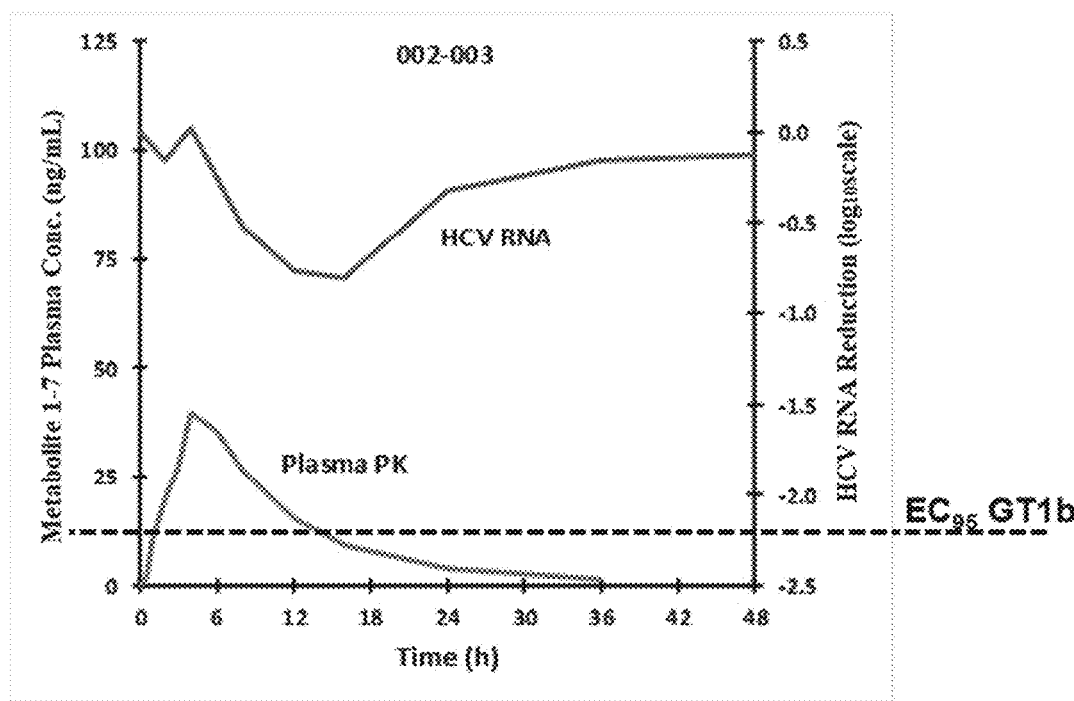
FIG. 23C is an individual pharmacokinetic/pharmacodynamic analysis of a subject enrolled in the 1b cohort as described in Example 24. The graph shows plasma metabolite 1-7 exposure and HCV RNA reduction levels. The dashed line represents the minimum concentration of metabolite 1-7 required to sustain a viral response greater than the $EC_{95}$ value against GT1b. The x-axis is time measured in hours. The left y-axis is metabolite 1-7 plasma concentration measured in ng/mL and the right y-axis is the HCV RNA reduction measured in $\log_{10}$ IU/mL.
Figure 23D:
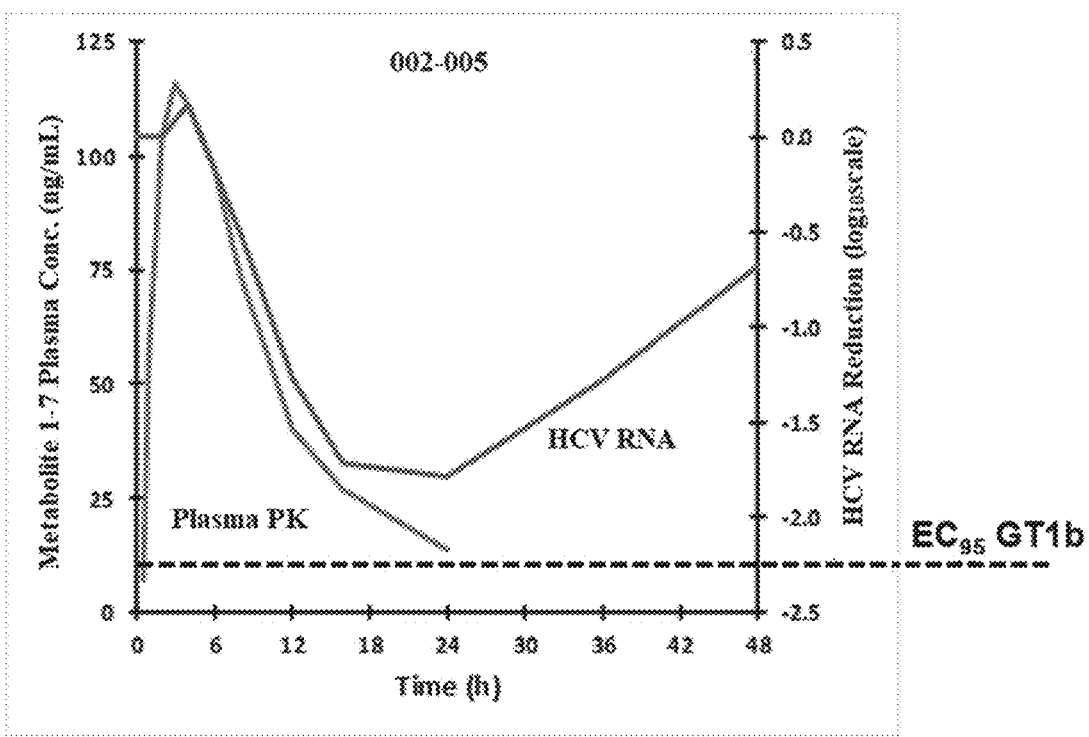
FIG. 23D is an individual pharmacokinetic/pharmacodynamic analysis of a subject enrolled in the 3b cohort as described in Example 24. Each graph shows plasma metabolite 1-7 exposure and HCV RNA reduction levels. The dashed line represents the minimum concentration of metabolite 1-7 required to sustain a viral response greater than the $EC_{95}$ value against GT1b. The x-axis is time measured in hours. The left y-axis is metabolite 1-7 plasma concentration measured in ng/mL and the right y-axis is the HCV RNA reduction measured in $\log_{10}$ IU/mL.
Figure 23E:
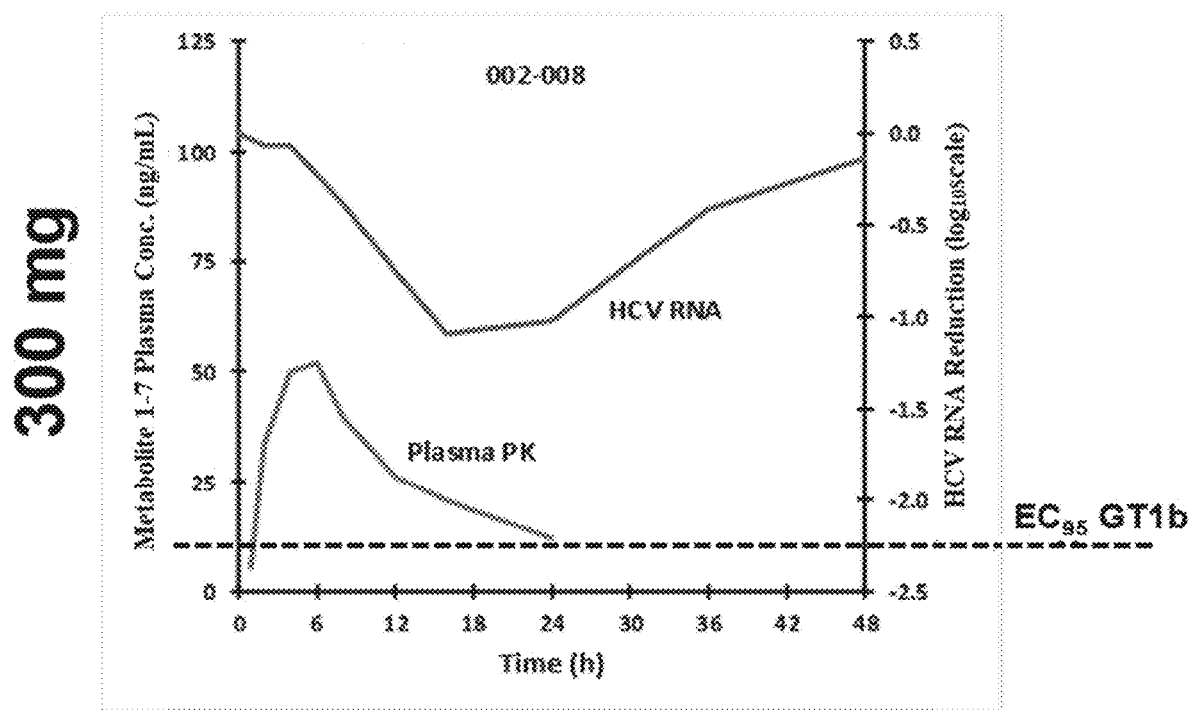
FIG. 23E is an individual pharmacokinetic/pharmacodynamic analysis of a subject enrolled in the 3b cohort as described in Example 24. Each graph shows plasma metabolite 1-7 exposure and HCV RNA reduction levels. The dashed line represents the minimum concentration of metabolite 1-7 required to sustain a viral response greater than the $EC_{95}$ value against GT1b. The x-axis is time measured in hours. The left y-axis is metabolite 1-7 plasma concentration measured in ng/mL and the right y-axis is the HCV RNA reduction measured in $\log_{10}$ IU/mL.
Figure 23F:
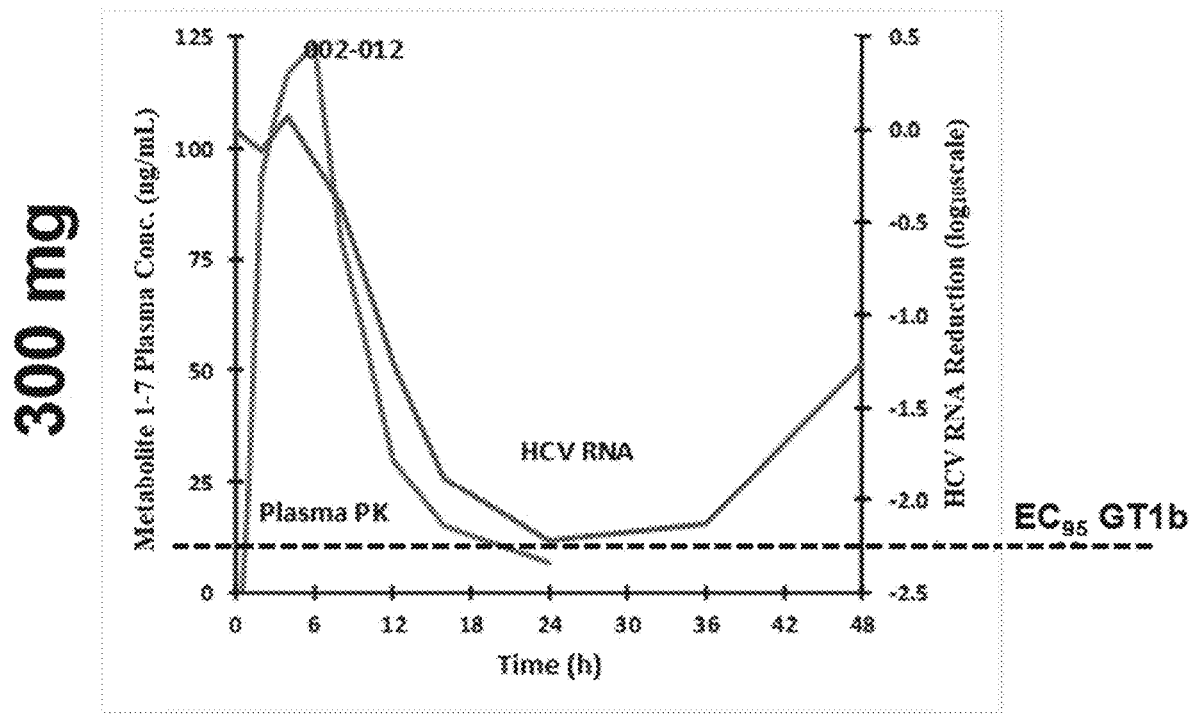
FIG. 23F is an individual pharmacokinetic/pharmacodynamic analysis of a subject enrolled in the 3b cohort as described in Example 24. Each graph shows plasma metabolite 1-7 exposure and HCV RNA reduction levels. The dashed line represents the minimum concentration of metabolite 1-7 required to sustain a viral response greater than the $EC_{95}$ value against GT1b. The x-axis is time measured in hours. The left y-axis is metabolite 1-7 plasma concentration measured in ng/mL and the right y-axis is the HCV RNA reduction measured in $\log_{10}$ IU/mL.

The mean plasma concentration-time profiles of Compound 1 and metabolite 1-7 were also calculated for all cohorts of Part A and Part B of the study. FIG. 21 is the mean plasma-concentration of Compound 1 following a single dose of Compound 2 and FIG. 22 is the mean plasma-concentration of metabolite 1-7 following a single dose of Compound 2. As shown in FIG. 21, Compound 1 was quickly absorbed and rapidly/extensively metabolized in all cohorts from Part B. As shown in FIG. 22, metabolite 1-7 was a major metabolite and exhibited sustained plasma concentrations. Plasma exposure of Compound 1 was dose-related while exposure of metabolite 1-7 was dose-proportional.

For the HCV-infected subjects of Part B, measurements of HCV RNA quantitation were performed before, during, and after administration of Compound 2. Plasma HCV RNA determinations were performed through the use of a validated commercial assay. Baseline was defined as the mean of Day −1 and Day 1 (pre-dose). A single 300 mg dose of Compound 2 (equivalent to 270 mg of Compound 1) resulted in significant antiviral activity in GT1b-HCV infected subjects. The mean maximum HCV RNA reduction 24 hours post-dose following a single 300 mg dose was 1.7 $\log_{10}$ IU/mL and this compares to a −2 log 10 IU/mL reduction after 1 day of 400 mg of sofosbuvir monotherapy in GT1a HCV-infected subjects. The mean maximum HCV RNA reduction 24 hours post-dose following a single 100 mg dose was 0.8 $\log_{10}$ IU/mL. The mean maximum HCV RNA reduction was 2.2 $\log_{10}$ IU/mL following a single 400 mg dose. Individual pharmacokinetic/pharmacodynamic analyses for the individual subjects from Part B of the study are shown in FIGS. 23A-23F. Metabolite 1-7 concentration is plotted against HCV RNA reduction concentration, and as shown in FIGS. 23A-23F, plasma HCV RNA reduction correlates with plasma metabolite 1-7 exposure. Viral response is sustained with metabolite 1-7 plasma concentrations that are greater than the $EC_{95}$ value against GT1b. The correlation between plasma concentration and HCV RNA reduction levels indicates that a more profound response will be achievable with higher doses of Compound 2.

Example 25. Predicted Steady-State Trough Levels of Metabolite 1-7 Exceed Compound 1 $EC_{95}$ Values Against Clinical Isolates of HCV GT 1-4

As shown in FIG. 24, the steady-state trough plasma levels ($C_{24,ss}$) of metabolite 1-7 following Compound 2 dosing in humans (600 mg QD (550 mg free base equivalent) and 450 mg QD (400 mg free base equivalent)) was predicted and compared to the $EC_{95}$ of Compound 1 in vitro across all tested clinical isolates to determine if the steady state plasma concentration is consistently higher than the $EC_{95}$, which would result in high efficacy against any or all tested clinical isolates in vivo. The $EC_{95}$ for Compound 1 is the same as the $EC_{95}$ of Compound 2. For Compound 2 to be effective, the steady-state trough plasma level of metabolite 1-7 should exceed the $EC_{95}$.

As shown in FIG. 24, the $EC_{95}$ of Compound 2 against all tested clinical isolates ranged from approximately 18 to 24 nM.

As shown in FIG. 24, Compound 2 at a dose of 450 mg QD (400 mg free base equivalent) in humans of provides a predicted steady state trough plasma concentration ($C_{24,ss}$) of approximately 40 ng/mL. Compound 2 at a dose of 600 mg QD (550 mg free base equivalent) in humans of provides a predicted steady state trough plasma concentration ($C_{24,ss}$) of approximately Therefore, the predicted steady state plasma concentration of surrogate metabolite 1-7 is almost double the $EC_{95}$ against all tested clinical isolates (even the hard to treat GT3a), which indicates superior performance.

In contrast, the $EC_{95}$ of the standard of care nucleotide sofosbuvir ranges from 50 to 265 nM across all tested HCV clinical isolates, with an $EC_{95}$ less than the predicted steady state concentration at the commercial dosage of 400 mg for only two isolates, GT2a and GT2b. The $EC_{95}$ for the commercial dosage of 400 mg of sofosbuvir is greater than the predicted steady state concentration for other clinical isolates, GT1a, GT1b, GT3a, GT4a, and GT4d.

The Compound 2 450 mg steady state trough plasma concentration ($C_{24,ss}$) was predicted using the 300 mg steady state trough plasma concentration ($C_{24,ss}$). The mean steady state trough plasma concentration ($C_{24,ss}$) at 300 mg was 26.4 ng/mL, and therefore the calculation was 26.4*450/300=39.6 ng/mL.

The 600 mg steady state trough plasma concentration ($C_{24,ss}$) was predicted using three approaches: 1) the 600 mg Day 1 $C_{24}$ mean was 25.8 ng/mL and a 60% increase was assumed for reaching steady state. Therefore the calculation was 25.8*1.6=41.3 ng/mL; 2) the 400 mg day 1 $C_{24}$ mean was 22.5 ng/mL and a 60% increase was assumed for reaching steady state. Taking dose proportional PK into account, the calculation was 22.5*1.6*600/400=54 ng/mL; and 3) the 300 mg steady state trough plasma concentration ($C_{24,ss}$) was 26.4 ng/mL and a proportional PK was assumed. Therefore the calculation was 26.4*2=52.8 ng/mL. The 600 mg steady state trough plasma concentration ($C_{24,ss}$) is the average of the 3 data points ((41.3±54±52.8)/3=49.3 ng/mL). There is generally about a 60% increase in $C_{24}$ at steady state compared to $C_{24}$ following a single dose.

The data comparing the efficacy and pharmacokinetic steady state parameters in FIG. 24 clearly demonstrates the unexpected therapeutic importance of Compound 2 for the treatment of hepatitis C. In fact, the predicted steady-state plasma level after administration of Compound 2 is predicted to be at least 2-fold higher than the $EC_{95}$ for all genotypes tested, and is 3- to 5-fold more potent against GT2. This data indicates that Compound 2 has potent pan-genotypic antiviral activity in humans. As shown in FIG. 24, the $EC_{95}$ of sofosbuvir at GT1, GT3, and GT4 is greater than 100 ng/mL. Thus surprisingly, Compound 2 is active against HCV at a dosage form that delivers a lower steady-state trough concentration (40-50 ng/mL) than the steady-state tough concentration (approximately 100 ng/mL) achieved by a similar dosage form of sofosbuvir.

Example 26. Formulation Description and Manufacturing of Compound 2

Figure 25:
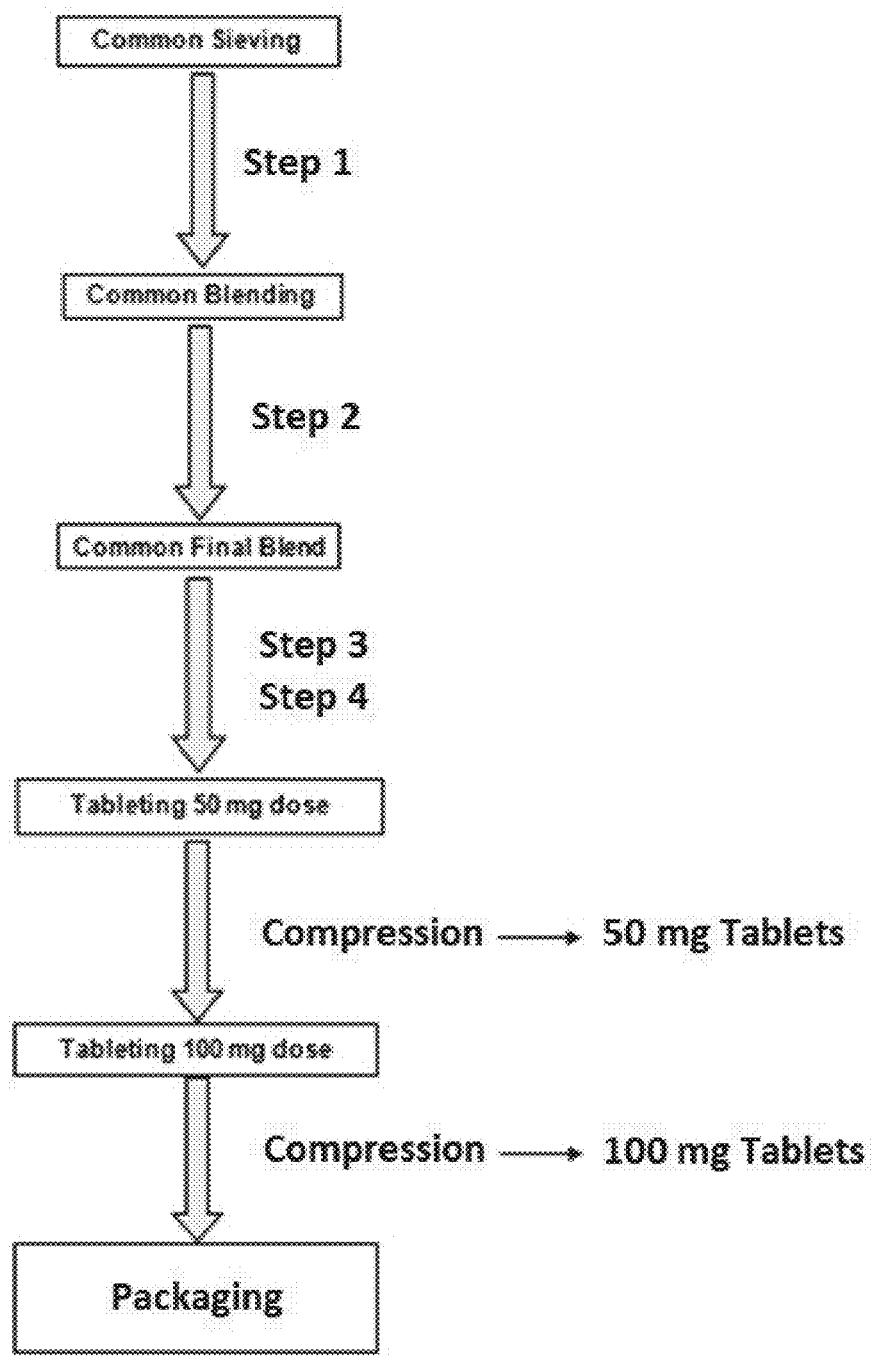
FIG. 25 is a flow diagram showing the manufacturing process of 50 mg and 100 mg tablets of Compound 2 as described in Example 26. In step 1, microcrystalline cellulose, Compound 2, lactose monohydrate, and croscarmellose sodium are filtered through a 600 µM screen. In step 2, the contents from step 1 are loaded into a V-blender and mixed for 5 minutes at 25 rpm. In step 3, magnesium stearate is filtered through a 600 µM screen. In step 4, magnesium stearate is loaded into the V-blender containing the contents from step 2 (microcrystalline cellulose, Compound 2, lactose monohydrate, and croscarmellose sodium) and mixed for 2 minutes at 25 rpm. The common blend is then divided for the production of 50 mg tablets and 100 mg tablets. To produce mg tablets, the blend from step 4 is compressed with 6 mm round standard concave tooling. To produce 100 mg tablets, the blend from step 4 is compressed with 8 mm round standard concave tooling. The tablets are then packaged into HDPE bottles induction-sealed with PP caps with desiccant.
Figure 26:
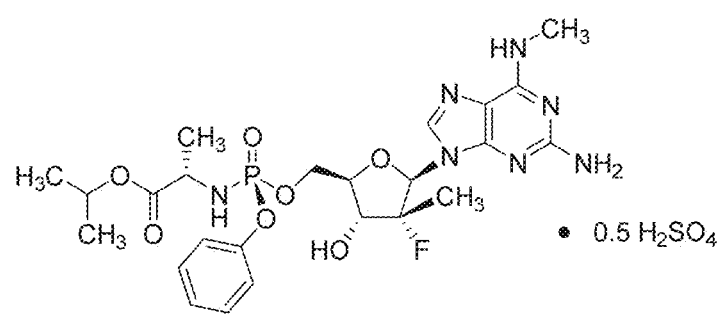
FIG. 26 is the hemi-sulfate salt that exhibits advantageous pharmacological properties over its corresponding free base for the treatment of an HCV virus.

A representative non-limiting batch formula for Compound 2 tablets (50 mg and 100 mg) is presented in Table 36. The tablets were produced from a common blend using a direct compression process as shown in FIG. 25. The active pharmaceutical ingredient (API) is adjusted based on the as-is assay, with the adjustment made in the percentage of microcrystalline cellulose. The API and excipients (microcrystalline cellulose, lactose monohydrate, and croscarmellose sodium) were screened, placed into a V-blender (PK Blendmaster, 0.5 L bowl) and mixed for 5 minutes at 25 rpm. Magnesium Stearate was then screened, added and the blend was mixed for an additional 2 minutes. The common blend was divided for use in producing 50 mg and 100 mg tablets. The lubricated blend was then compressed at a speed of 10 tablets/minutes using a single punch research tablet press (Korsch XP1) and a gravity powder feeder. The 50 tablets were produced using round standard concave 6 mm tooling and 3.5 kN forces. The 100 mg tablets were produced using 8 mm round standard concave tooling and 3.9-4.2 kN forces.

TABLE 36

Formulation of 50 mg and 100 mg Compound 2 Tablets

| Raw Material | % w/w | g/ batch | Mg/unit 50 mg Tablet | Mg/unit 100 mg Tablet |
|---|---|---|---|---|
| Compound 2 | 50.0 | 180.0 | 50.0 | 100.0 |
| Microcrystalline Cellulose, USP/NF, EP | 20.0 | 72.0 | 20.0 | 40.0 |
| Lactose Monohydrate, USP/NF, BP, EP, JP | 24.0 | 86.4 | 24.0 | 48.0 |
| Croscarmellose Sodium, USP/NF, EP | 5.0 | 18.0 | 5.0 | 10.0 |
| Magnesium Stearate, USP/NF, BP, EP JP | 1.0 | 3.6 | 1.0 | 2.0 |
| Total | | | 100.0 | 200.0 |

Compound 2 was adjusted based on the as-is assay, with the adjustment made in the percentage of microcrystalline cellulose. Compound 2 and excipients (microcrystalline cellulose, lactose monohydrate, and croscarmellose sodium) were screened, placed into a V-blender (PK Blendmaster, 0.5 L bowl) and mixed for 5 minutes at 25 rpm. Magnesium stearate was then screened, added and the blend was mixed for an additional 2 minutes. The common blend was divided for use in producing 50 mg and 100 mg tablets. The lubricated blend was then compressed at a speed of 10 tablets/minutes using a single punch research tablet press (Korsch XP1) and a gravity powder feeder. The 50 mg tablets were produced using round standard concave 6 mm tooling and 3.5 kN forces. The 100 mg tablets were produced using 8 mm round standard concave tooling and 3.9-4.2 kN forces. The specifications of the 50 mg and 100 mg tablets are shown in Table 37.

TABLE 37

Specifications of 50 mg and 100 mg Tablets of Compound 2

| | 50 mg Tablets | 100 mg Tablets |
|---|---|---|
| Average Weight (n = 10) | 100 ± 5 mg | 200 ± 10 mg |
| Individual Weight | 100 ± 10 mg | 200 ± 20 mg |
| Hardness | 5.3 kp | 8.3 kp |
| Disintegration | <15 minutes | <15 minutes |
| Friability | NMT 0.5% | NMT 0.5% |

The 50 mg and 100 mg tablets produced as described above were subjected to 6 month stability studies under three conditions: 5° C. (refrigeration), 25° C./60% RH (ambient), and RH (accelerated). Both the 50 mg and 100 mg tablets were chemically stable under all three conditions tested.

Under refrigeration conditions (5° C.), both the 50 mg and 100 mg tablets remained white solids that did not change in appearance from T=0 to T=6 months. Throughout the 6-month study, no impurities were reported that were greater than 0.05% for either the 50 mg tablets or the 100 mg tablets. The water content after 6 months was also less than 3.0% w/w for both tablets. Similar results were reported when the tablets were subjected to ambient conditions (25° C./60% RH); no impurities that were greater than 0.05% were reported throughout the 6 months for both tablets and the water content did not exceed 3.0% w/w at the 6-month mark. When the tablets were subjected to accelerated conditions (40° C./75% RH), the appearance of the 50 mg and 100 mg tablets did not change from a white, round tablet. One impurity was reported after 3 months, but the impurity was only 0.09%. A second impurity was reported after 6 months, but the total impurity percentage was only 0.21% for both the 50 mg and 100 mg tablets. Water content was 3.4% w/w at 6 months for the 50 mg tablets and 3.2% w/w for the 100 mg tablets.

In a separate study, the stability of 50 mg and 100 mg tablets of Compound 2 at ambient conditions (25° C./60% RH) was measured over 9 months. The appearance of the 50 mg and 100 mg tablet did not change from a white round tablet over the course of 9 months. Impurities in the 50 mg tablet were less than 0.10% after 9 months and impurities in the 100 mg tablet were less than 0.05%. The water content of the 50 mg tablet and the 100 mg tablet after 9 months was only 2.7% w/w and 2.6% w/w, respectively.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

What is claimed is:

1. A process for preparing Compound 2 comprising the steps of:
(a) dissolving Compound 1 in an organic solvent;

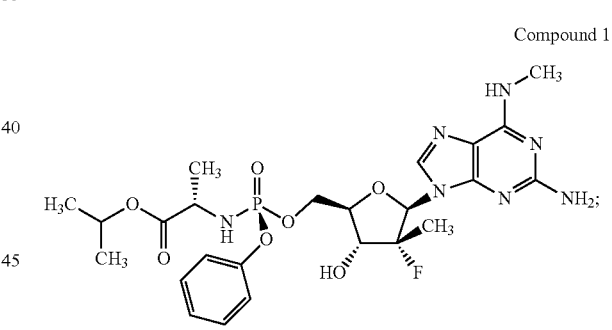

(b) adding a sufficient amount of $H_2SO_4$/solvent mixture to the solution of Compound 1 from step (a) to form a hemisulfate salt (Compound 2);

(c) stirring the reaction until Compound 2 precipitates; and (d) filtering the Compound 2 precipitate and washing with an organic solvent or a mixture of organic solvents.

2. The process of claim 1, wherein the ratio of $H_2SO_4$ to Compound 1 is about 0.5 to 1.

3. The process of claim 2, further comprising step (e) wherein Compound 2 is dried in a vacuum.

4. The process of claim 2, wherein the organic solvent from step (a) is selected from the group consisting of acetone, ethyl acetate, methanol, acetonitrile, and ether.

5. The process of claim 2, wherein the organic solvent from step (a) is selected from the group consisting of 3-methyl-2-pentanone, ethyl isopropyl ketone, methyl propionate, and ethyl butyrate.

6. The process of claim 4, wherein the organic solvent in step (a) is acetone.

7. The process of claim 4, wherein the organic solvent in step (a) is ethyl acetate.

8. The process of claim 2, wherein the $H_2SO_4$/solvent mixture of step (b) is selected from the group consisting of $H_2SO_4$/methanol, $H_2SO_4$/isopropanol, $H_2SO_4$/ethanol, and $H_2SO_4$/n-butanol.

9. The process of claim 8, wherein the $H_2SO_4$/solvent mixture of step (b) is $H_2SO_4$/methanol.

10. The process of claim 9, wherein the $H_2SO_4$/methanol mixture of step (b) is cooled to about 0-10° C. before addition to the solution of Compound 1.

11. The process of claim 2, wherein the Compound 2 precipitate of step (d) is washed with a mixture of organic solvents selected from ethanol/acetone, isopropanol/acetone, and n-butanol/acetone.

12. The process of claim 11, wherein the Compound 2 precipitate is washed with methanol/acetone in step (d).

13. The process of claim 2, wherein Compound 2 is dried in a vacuum at a temperature from about 55° C. to about 60° C. in step (e).

14. The process of claim 2, wherein the organic solvent of step (a) is acetone, the $H_2SO_4$/solvent mixture of step (b) is $H_2SO_4$/methanol, and the mixture of solvents of step (d) is methanol/acetone.

15. The process of claim 14, further comprising step (e) wherein Compound 2 is dried in a vacuum.

* * * * *